United States Patent
Freyne et al.

(10) Patent No.: US 6,583,141 B1
(45) Date of Patent: Jun. 24, 2003

(54) 4,5-DIHYDRO-ISOXAZOLE DERIVATIVES AND THEIR PHARMACEUTICAL USE

(75) Inventors: Eddy Jean Edgard Freyne, Rumst (BE); José Ignacio Andrés-Gil, Drongen (ES); Frederik Dirk Deroose, Boom (BE); Davy Petrus Franciscus Maria Petit, Beerse (BE); Maria Encarnacion Matesanz-Ballesteros, Toledo (ES); Rosa Maria Alvarez Escobar, Toledo (ES)

(73) Assignee: Janssen Pharmaceutica, N.V. (BE)

( * ) Notice: Subject to any disclaimer, the term of this patent is extended or adjusted under 35 U.S.C. 154(b) by 0 days.

(21) Appl. No.: 09/807,149

(22) PCT Filed: Oct. 7, 1999

(86) PCT No.: PCT/EP99/07803

§ 371 (c)(1),
(2), (4) Date: Apr. 6, 2001

(87) PCT Pub. No.: WO00/21959

PCT Pub. Date: Apr. 20, 2000

(30) Foreign Application Priority Data

Oct. 9, 1998 (EP) .............................. 98203394

(51) Int. Cl.[7] .................... C07D 413/04; C07D 261/04; C07D 413/14; A61K 31/42; A61K 31/4427

(52) U.S. Cl. ............................. 514/236.8; 546/272.1; 546/256; 546/270.7; 546/146; 546/269.1; 514/340; 514/333; 514/342; 514/307; 514/253.1; 514/256; 514/378; 544/131; 544/364; 544/333; 548/240

(58) Field of Search .................. 546/272.1, 256, 546/270.7, 146, 269.1; 514/340, 333, 342, 307, 236.8, 253.1, 256, 378; 544/131, 364, 333; 548/240

(56) References Cited

U.S. PATENT DOCUMENTS 5,814,627 A    9/1998  Schwab et al.

FOREIGN PATENT DOCUMENTS

| DE | 44 08 084 A1 | 9/1995 |
|---|---|---|
| WO | WO 93/1906 A1 | 9/1993 |
| WO | WO 95/14680 A1 | 6/1995 |
| WO | WO 95/24398 A1 | 9/1995 |
| WO | WO 96/38426 A1 | 12/1996 |

OTHER PUBLICATIONS

Kleinman, E. F. et al., Striking Effect of Hydroxamic Acid Substitution on the Phosphodiesterase Type 4 (PDE4) and TNFα Inhibitory Activity of Two Series of Rolipram Analogues: Implications for a New Active Site Model of PDE4, J. Med. Chem., 1998, 41, 266–270.

Primary Examiner—John M. Ford
Assistant Examiner—Hong Liu

(57) ABSTRACT

The present invention is concerned with the compounds of formula

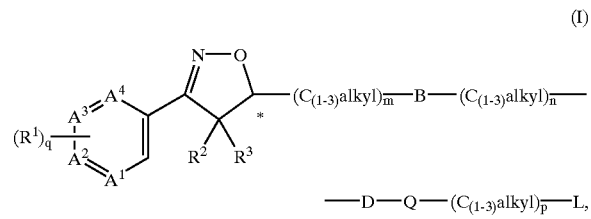

(I)

wherein m, n and p are each independently 0 or 1 and q is 0, 1, 2, 3, 4 or 5; —$A^1$=$A^2$—$A^3$=$A^4$— is a pyridinylidene, pyridazinylidene, pyrimidinylidene, pyrazinylidene or phenylidene; B represents an amide, ketone or oxadiazole; D represents Ar or Het; Q represents a covalent direct bond or a ketone, —N—, —O—, —$CR^5R^6$—, amide ethenyl, imine, sulfonyl, sulfinyl, 3-oxobutenyl, pyrazole, isoxazole or thiazole; L represents Ar or Het; $R^1$ represents hydrogen, halo, hydroxy, $C_{(2-6)}$alkenyl, $C_{(2-6)}$alkynyl, $C_{(3-6)}$cycloalkyl, $C_{(3-6)}$cycloalkenyl, cyano, guanidine, nitro, $NR^{17}R^{18}$, an optionally substituted $C_{(1-6)}$alkyl or $C_{(1-6)}$alkyloxy; $R^2$ and $R^3$ each independently represent hydrogen, halo, $C_{(1-6)}$alkyloxy or an optionally substituted $C_{(1-6)}$alkyl; $R^5$ and $R^6$ each independently represent hydrogen, hydroxy, halo, an optionally substituted $C_{(1-6)}$alkyl, $C_{(2-6)}$alkenyl, $C_{(2-6)}$alkynyl, $C_{(3-6)}$cycloalkyl, $C_{(3-6)}$cycloalkenyl, $C_{(1-6)}$alkyloxy, cyano, (C=O)$R^{25}$, (C=O)O$R^{16}$, (SO$_2$)$R^{16}$, aminocarbonyloxy, amino$C_{(1-6)}$alkyl, $NR^{17}R^{18}$, $N_3$, Ar or Het; or $R^5$ and $R^6$ together with the carbon atom to which they are attached, form an Ar or Het; Ar represents an optionally substituted $C_{(6-14)}$aryl; Het represents an optionally substituted $C_{(1-14)}$heterocycle; or a N-oxide, pharmaceutically acceptable addition salt, quaternary amine or stereochemically isomeric form thereof; the processes for their preparation and compositions comprising them. It further relates to their use as a medicine.

15 Claims, No Drawings

4,5-DIHYDRO-ISOXAZOLE DERIVATIVES AND THEIR PHARMACEUTICAL USE

CROSS REFERENCE TO RELATED APPLICATIONS

This application is the national stage filing of PCT Application No. PCT/EP99/07803, filed Oct. 7, 1999 which application claims priority from EPO application No. 98203394.6, filed Oct. 9, 1998.

The present invention is directed to novel isoxazole compounds, methods for their preparation, pharmaceutical compositions comprising these compounds, and their use in therapy, particularly in the prevention and/or treatment of disease states associated with immune cell activation and proliferation.

Higher organisms are characterized by an immune system which protects them against foreign pathogens and endogenous diseases such as tumors and genetic defects. The immune system has developed a series of pathways to protect the host. The primary cells of the immune system are lymphocytes. One class of lymphocytes, T lymphocytes, affects and regulates the cell mediated response of the immune system. They consist of a heterogeneous population of cells with several distinct functional subsets called helper cells, suppressor cells and killer cells.

T lymphocytes are derived from the thymus and circulate through the blood and lymphatic vessels of the body where they can detect and interact with foreign invaders i.e. viruses, allergens, tumors and autoantigens. Upon specific interaction with invading pathogens, T lymphocytes are activated, resulting in the development of enlarged cells—T cell blasts—which subsequently turn on the machinery for cytokine synthesis, cytokine receptor expression and proliferation. This initiates a cascade of host defense actions involving other lymphocyte subsets.

While the normal immune system is closely regulated, aberrations in the immune response are not uncommon. Many signs and symptoms of infectious, inflammatory and neoplastic diseases evolve as a result of abnormalities in the immune system, especially in T lymphocyte-mediated immunity. Even if these immunocompetent cells are not involved in the initial stage, abnormal regulation of otherwise normal appropriate cellular immune reactions may lead to acute and chronic diseases. These diseases are often of unknown etiology and include systemic rheumatic diseases, organ specific endocrine diseases, inflammatory disease of the gut and skin. The treatments available in relation to said diseases are usually symptomatic or palliative, i.e. most of the drugs prescribed in connection with said diseases are directed at allaying the symptoms and have no curative effect. Thus, a long-felt need exists for an effective means of curing or ameliorating T lymphocyte-mediated pathologies. Such a treatment should ideally control the inappropriate T cell response, rather than merely reducing the symptoms.

Current treatments of immunoinflammatory and proliferative diseases involve the administration of drugs which suppress the immune response. Examples of such drugs include methotrexate, cyclophosphamide, azathioprine, rapamicine, cyclosporin A, FK-506 and leflunomide. The use of these drugs is limited due to the cytotoxic effect (gastrointestinal symptoms, nefro- and hepatotoxicity) on the host and also because they induce global immunosuppression. For example, prolonged treatment with these drugs can lead to infections and malignancies. Steroid compounds like corticosteroids (prednisolone, deflazacort) are also employed in many instances. Although some efficacy of corticosteroids in immunoinflammatory diseases was demonstrated, their long term adverse effects, particularly osteoporosis, have remained a substantial obstacle limiting their routine use.

A more selective therapeutic approach involves the use of antibodies or soluble receptors directed to T cell markers (e.g. CD4, CD8, B7, T cell receptor) or to cytokines involved in the disease (e.g. IL-1, IL-2, TNF-α) or their receptors. These alternatives are associated with high production costs. Another proposed therapy involves the induction of tolerance by the oral administration of the antigen which is related to the cause of the disease. However, use of this therapeutic modality is limited due to the difficulty in identifying and purifying the antigen(s) responsible for the autoimmune disease afflicting the patient.

Thus, new compounds with improved therapeutic activity and reduced side effects are needed.

Accordingly, the present invention provides certain isoxazole derivatives having the formula

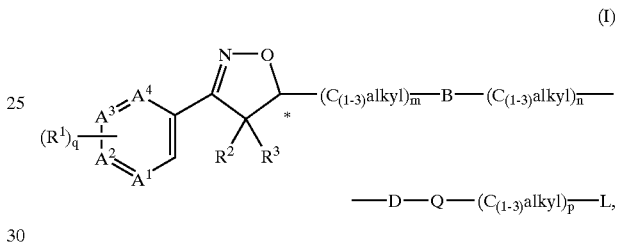

wherein m, n and p are each independently 0 or 1 and q is 0, 1, 2, 3, 4 or 5; —$A^1$=$A^2$—$A^3$=$A^4$— is a bivalent radical of formula

 (a-1)

 (a-2)

 (a-3)

 (a-4)

 (a-5)

 (a-6)

 (a-7)

B is a bivalent radical of formula

 (b-1)

 (b-2)

 (b-3)

 (b-4)

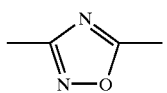
(b-5)

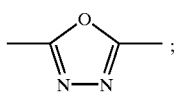
(b-6)

D is $Ar^1$ or $Het^1$;

Q is a direct covalent bond or a bivalent radical of formula

(c-1)

(c-2)

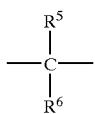
(c-3)

(c-4)

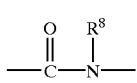
(c-5)

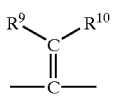
(c-6)

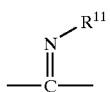
(c-7)

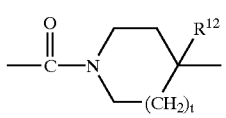
(c-8)

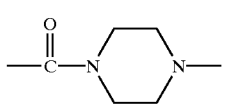
(c-9)

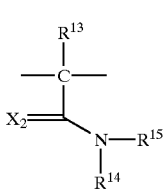
(c-10)

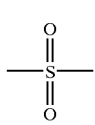
(c-11)

(c-12)

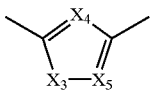
(c-13)

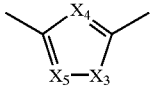
(c-14)

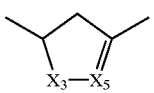
(c-15)

(c-16)

(c-17)

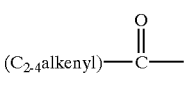
(c-18)

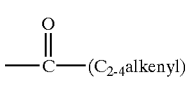
(c-19)

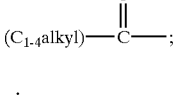

wherein
$X_1$ and $X_2$ are each independently S or O, t is 0, 1 or 2;
$X_3$ is independently S, O or $NR^{26}$; $X_4$ and $X_5$ are each independently N or CH.
L is $Ar^1$ or $Het^1$;
$R^1$ is selected from hydrogen, halo, hydroxy, $C_{(1-6)}$alkyl, $C_{(2-6)}$alkenyl, $C_{(2-6)}$alkynyl, $C_{(3-6)}$cycloalkyl, $C_{(3-6)}$cycloalkenyl, $C_{(1-6)}$alkyloxy, $C_{(3-6)}$cycloalkenyl$C_{(1-6)}$alkyl, $C_{(3-6)}$cycloalkyloxy, halo$C_{(1-6)}$alkyl, cyano, guanidine, nitro and $NR^{17}R^{18}$;
$R^2$ and $R^3$ are each independently selected from hydrogen, halo, $C_{(1-6)}$alkyloxy and $C_{(1-6)}$alkyl where the alkyl moiety may be optionally substituted by one or more hydroxy [for example 1, 2 or 3];
$R^4$ is selected from hydrogen, $C_{(1-6)}$alkyl, $C_{(2-6)}$alkenyl, $C_{(2-6)}$alkynyl, $C_{(3-6)}$cycloalkyl and $C_{(3-6)}$cycloalkenyl;
$R^5$, $R^6$, $R^9$ and $R^{10}$ are each independently selected from hydrogen, hydroxy, halo, $C_{(1-6)}$alkyl, [where the alkyl moiety may be optionally substituted by one or more substituents independently selected from hydroxy, halo, $C_{(1-6)}$alkyloxy, $NR^{17}R^{18}$, $(SO_2)R^{16}$, $(C=O)R^{16}$, $Ar^1$ and $Het^1$], $C_{(2-6)}$alkenyl, $C_{(2-6)}$alkynyl, $C_{(3-6)}$cycloalkyl, $C_{(3-6)}$cycloalkenyl, $C_{(1-6)}$alkyloxy [where the alkenyl, alkynyl, cycloalkyl, cycloalkenyl and alkyloxy moiety may be optionally substituted by one or more substituents independently selected from hydroxy, halo $C_{(1-6)}$alkyloxy, $(=O)$, $NR^{17}R^{18}$, $(SO_2)R^{16}$, $(C=O)R^{16}$, $Ar^1$ and $Het^1$], cyano, $(C=O)R^{25}$, $(C=O)OR^{16}$, $(SO_2)R^{16}$, aminocarbonyloxy, amino$C_{(1-6)}$alkyl, $NR^{17}R^{18}$, $N_3$, $Ar^1$ and $Het^1$;
or
$R^5$ and $R^6$ and $R^{10}$ together with the carbon atom to which they are attached, form a $Het^1$ or a $C_{(2-14)}$ carbocyclic radical optionally substituted by 1,2 or 3 substituents independently selected from halo, hydroxy, $C_{(1-6)}$alkyl, $C_{(2-6)}$alkenyl, $C_{(2-6)}$alkynyl, $C_{(3-6)}$cycloalkyl, $C_{(3-6)}$cycloalkenyl, $C_{(1-6)}$alkyloxy [where the alkyl, alkenyl, alkynyl, cycloalkyl, cycloalkenyl and alkyloxy moiety may be optionally substituted by one or more substituents independently selected from hydroxy, halo, $C_{(1-6)}$ alkyloxy, $NR^{23}R^{24}$, $(C=O)R^{22}$, $C_{(6-14)}$aryl and $C_{(1-14)}$ heterocycle], cyano, (=O), (=NH), $(C=O)R^{22}$, $(SO_2)R^{22}$, $NH(C=O)R^{22}$, $NR^{23}R^{24}$, $C_{(6-14)}$aryl, $C_{(6-14)}$arylthio, $C_{(6-14)}$aryloxy [where the aryloxy moiety may be optionally substituted by halo] and $C_{(1-14)}$heterocycle;

$R^7$ and $R^8$ are each independently selected from hydrogen, hydroxy, $C_{(1-6)}$alkyl, $C_{(2-6)}$alkenyl, $C_{(2-6)}$alkynyl, $C_{(3-6)}$cycloalkyl, $C_{(3-6)}$cycloalkenyl, hydroxy$C_{(1-6)}$alkyl and $C_{(1-6)}$alkyloxy;

$R^{11}$ is selected from hydrogen, hydroxy and $C_{(1-6)}$alkyloxy [where the alkyloxy moiety may be optionally substituted by $(C=O)R^{16}$];

$R^{12}$ is selected from hydrogen and hydroxy;

$R^{13}$ is selected from hydrogen, hydroxy, halo, $C_{(1-6)}$alkyl, $C_{(2-6)}$alkenyl, $C_{(2-6)}$alkynyl, $C_{(3-6)}$cycloalkyl, $C_{(3-6)}$cycloalkenyl, $C_{(1-6)}$alkyloxy [where the alkyl, alkenyl, alkynyl, cycloalkyl, cycloalkenyl and alkyloxy moiety may be optionally substituted by one or more substituents independently selected from hydroxy, halo, (=O), $NR^{17}R^{18}$, $(SO_2)R^{16}$, $(C=O)R^{16}$, $Ar^1$ and $Het^1$], aminocarbonyloxy, amino($C_{(1-6)}$alkyl, $NR^{17}R^{18}$, $N_3$, $Ar^1$ and $Het^1$;

$R^{14}$ and $R^{15}$ are each independently selected from hydrogen, $C_{(1-6)}$alkyl, $C_{(2-6)}$alkenyl, $C_{(2-6)}$alkynyl, $C_{(3-6)}$cycloalkyl, $C_{(3-6)}$cycloalkenyl, $C_{(1-6)}$alkyloxy [where the alkyl, alkenyl, alkynyl, cycloalkyl, cycloalkenyl and alkyloxy moiety may be optionally substituted by one or more substituents independently selected from hydroxy, $C_{(3-6)}$ cycloalkyl, $C_{(1-6)}$alkyloxy, cyano, $(C=O)R^{16}$, $Ar^1$ and $Het^1$], $C_{(6-14)}$aryl$C_{(1-6)}$alkyl, $(C=)R^{16}$, $(C=O)OR^{16}$, $(C=S)R^{16}$, $(SO_2)R^{16}$, $Ar^1$ and $Het^1$; or $R^{14}$ and $R^{15}$ together with the N atom to which they are attached, form a $C_{(1-14)}$heterocycle optionally substituted by 1, 2 or 3 substituents independently selected from halo, hydroxy, $C_{(1-6)}$alkyl, $C_{(2-6)}$alkenyl, $C_{(2-6)}$alkynyl, $C_{(3-6)}$ cycloalkyl, $C_{(3-6)}$cycloalkenyl and $C_{(1-6)}$alkyloxy [where the alkyl, alkenyl, alkynyl, cycloalkyl, cycloalkenyl and alkyloxy moiety may be optionally substituted by one or more substituents independently selected from halo, $C_{(1-6)}$alkyloxy, $(C=))R^{16}$, $Ar^1$ and $Het^1$], $C_{(6-14)}$arylthio, $C_{(6-14)}$aryloxy, cyano, $(C=O)R^{16}$, $(C=O)OR^{16}$, $(SO_2)R^{16}$, $NR^{17}R^{18}$, $Ar^1$ and $Het^1$;

$R^{16}$ is selected from hydrogen, hydroxy, $C_{(1-6)}$alkyl, $C_{(2-6)}$ alkenyl, $C_{(2-6)}$alkynyl, $C_{(3-6)}$cycloalkyl, $C_{(3-6)}$ cycloalkenyl, $C_{(1-6)}$alkyloxy [where the alkyl, alkenyl, alkynyl, cycloalkyl, cycloalkenyl and alkyloxy moiety may be optionally substituted by one or more substituents independently selected from halo, $C_{(1-6)}$ alkyloxycarbonyl, $NR^{17}R^{18}$, $Ar^1$ and $Het^1$], $NR^{17}R^{18}$, $C_{(6-14)}$aryloxy, $Ar^1$ or $Het^1$;

$R^{17}$ and $R^{18}$ are each independently selected from hydrogen, hydroxy, $C_{(1-6)}$alkyl, $C_{(2-6)}$alkenyl, $C_{(2-6)}$alkynyl, $C_{(3-6)}$ cycloalkyl, $C_{(3-6)}$cycloalkenyl, $C_{(1-6)}$alkyloxy [where the alkyl, alkenyl, alkynyl, cycloalkyl, cycloalkenyl and alkyloxy moiety may be optionally substituted by one or more substituents independently selected from hydroxy, $C_{(3-6)}$ cycloalkyl, $C_{(1-6)}$alkyloxy, $(C=O)R^{19}$, $Ar^1$ and $Het^1$], $(C=O)R^{19}$, $(SO_2)R^{19}$, $Ar^1$ and $Het^1$; or $R^{17}$ and $R^{18}$ together with the N atom to which they are attached, form a $C_{(1-14)}$heterocycle optionally substituted by 1,2 or 3 substituents independently selected from hydroxy, $C_{(1-6)}$alkyl, $C_{(2-6)}$alkenyl, $C_{(2-6)}$alkynyl, $C_{(3-6)}$ cycloalkenyl, $C_{(1-6)}$alkyloxy [where the alkyl, alkenyl, alkynyl, cycloalkyl, cycloalkenyl and alkyloxy moiety may be optionally substituted by one or more substituents independently selected from hydroxy, $C_{(1-6)}$alkyloxy, $(C=O)R^{19}$, $Ar^1$ and $Het^1$], $NR^{20}R^{21}$, $(C=O)R^{19}$, (=NH), S—$Ar^1$, $Ar^1$ and $Het^1$;

$R^{19}$ is selected from $C_{(1-6)}$alkyl, $C_{(2-6)}$alkenyl, $C_{(2-6)}$alkynyl, $C_{(3-6)}$cycloalkyl, $C_{(3-6)}$cycloalkenyl, $C_{(1-6)}$alkyloxy [where the alkyl, alkenyl, alkynyl, cycloalkyl, cycloalkenyl and alkyloxy moiety may be optionally substituted by one or more substituents independently selected from halo, $(C=O)R^{22}$, $NR^{20}R^{21}$, $Ar^1$ and $Het^1$], phenyloxy, $NR^{20}R^{21}$, $Ar^1$ and $Het^1$;

$R^{20}$ is selected from hydrogen, $C_{(1-6)}$alkyl, $C_{(2-6)}$alkenyl, $C_{(2-6)}$alkynyl, $C_{(3-6)}$cycloalkyl, $C_{(3-6)}$cycloalkenyl, $NH(C=O)R^{22}$ and $C_{(1-6)}$alkyloxy;

$R^{21}$ is selected from hydrogen, hydrogen, $C_{(1-6)}$alkyl, $C_{(2-6)}$alkenyl, $C_{(2-6)}$alkynyl, $C_{(3-6)}$cycloalkyl, $C_{(3-6)}$ cycloalkenyl, $C_{(1-6)}$alkyloxy, $C_{(1-6)}$alkyloxycarbonyl, $Ar^1$ and $Het^1$;

$Ar^1$ is a $C_{(1-14)}$aryl (or $C_{(6-14)}$arylidene when D is $Ar^1$) optionally substituted by one or more substituents independently selected from halo, hydroxy, $C_{(1-6)}$alkyl, $C_{(2-6)}$ alkenyl, $C_{(2-6)}$alkynyl, $C_{(3-6)}$cycloalkyl, $C_{(3-6)}$ cycloalkenyl, $C_{(1-6)}$alkyloxy [where the alkyl, alkenyl, alkynyl, cycloalkyl, cycloalkenyl and alkyloxy moiety may be optionally substituted by one or more substituents independently selected from hydroxy, halo, $C_{(1-6)}$ alkyloxy, $NR^{23}R^{24}$, $(C=O)R^{22}$, $C_{(6-14)}$aryl and $C_{(1-14)}$ heterocycle], cyano, (=O), (=NH), $(C=O)R^{22}$, $(SO_2)R^{22}$, $NH(C=O)R^{22}$, $NR^{23}R^{24}$, $C_{(6-14)}$aryl, $C_{(6-14)}$arylthio, $C_{(6-14)}$aryloxy [where the aryloxy moiety may be optionally substituted by halo] and $C_{(1-14)}$heterocycle;

$Het^1$ is a $C_{(1-14)}$heterocycle (or $C_{(1-14)}$heterocyclidene when D is $Het^1$) optionally substituted by one or more substituents independently selected from halo, hydroxy, $C_{(1-6)}$ alkyl, $C_{(2-6)}$alkenyl, $C_{(2-6)}$alkynyl, $C_{(3-6)}$cycloalkyl, $C_{(3-6)}$ cycloalkenyl, $C_{(1-6)}$alkyloxy [where the alkyl, alkenyl, alkynyl, cycloalkyl, cycloalkenyl and alkyloxy moiety may be optionally substituted by one or more substituents independently selected from hydroxy, halo, $C_{(1-6)}$ alkyloxy, $NR^{23}R^{24}$, $(C=O)R^{22}$, $C_{(6-14)}$aryl and $C_{(1-14)}$ heterocycle], cyano, (=O), (=NH), $(C=O)R^{22}$, $(SO_2)R^{22}$, $NH(C=O)R^{22}$, $NR^{23}R^{24}$, $C_{(6-14)}$aryl, $C_{(6-14)}$arylthio, $C_{(6-14)}$aryloxy [where the aryloxy moiety may be optionally substituted by halo] and $C_{(1-14)}$heterocycle;

$R^{22}$ is selected from hydrogen, hydroxy, $C_{(1-6)}$alkyl, $C_{(1-6)}$ alkyloxy, halo$C_{(1-6)}$alkyl, $NR^{23}R^{24}$ and

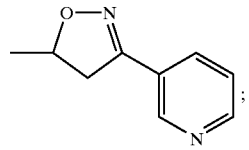

$R^{23}$ and $R^{24}$ are each independently selected from hydrogen, $C_{(1-6)}$alkyl and

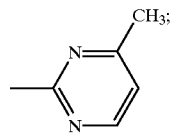

$R^{25}$ is selected from hydrogen, hydroxy, $C_{(1-6)}$alkyl, $C_{(2-6)}$ alkenyl, $C_{(2-6)}$alkynyl, $C_{(3-6)}$cycloalkyl, $C_{(3-6)}$ cycloalkenyl, $C_{(1-6)}$alkyloxy [where the alkyl, alkenyl, alkynyl, cycloalkyl, cycloalkenyl and alkyloxy moiety may be optionally substituted by one or more substituents independently selected from halo, $C_{(1-6)}$alkyloxycarbonyl, $NR^{17}R^{18}$, $Ar^1$ and $Het^1$], $C_{(6-14)}$aryloxy, $Ar^1$ and $Het^1$;

$R^{26}$ is selected from hydrogen, $C_{(1-6)}$alkyl and phenyl;

or a N-oxide, addition salt, quaternary amine or stereochemically isomeric form thereof;

A special group of compounds are those compounds of formula (I) wherein Q is a bivalent radical of formula (c-1), (c-2), (c-3), (c-4), (c-5), (c-6), (c-7), (c-8), (c-9), (c-10), (c-11) or (c-12).

Further, suitable compounds of formula (I) include those wherein —$A^1$=$A^2$—$A^3$=$A^4$— is a radical of formula (a-1), (a-2), (a-3), (a-4), (a-5) or (a-6).

According to a further aspect the present invention provides compounds of formula (I) wherein:

m is 0 or 1;
n is 0;
p is 0 or 1;
q is 0, 1, 2 or 3;
—$A^1$=$A^2$—$A^3$=$A^4$— is a radical of the formula (a-1), (a-2), (a-3), (a-4), (a-5), (s-6) or (a-7), preferably (a-1), (a-2), (a-3), (a-4), (a-5) or (a-6);
D is selected from pyridinylidene and phenylidene [where the phenylidene moiety is optionally substituted by one or more substituents independently selected from halo, $C_{(1-6)}$alkyl, $C_{(1-6)}$alkyloxy, phenyl$C_{(1-3)}$alkyloxy, halo$C_{(1-6)}$alkyl and (C=O)$R^{16}$];
L is selected from phenyl [where the phenyl moiety is optionally substituted by one or more substituents independently selected from halo, $C_{(1-6)}$alkyl, amino$C_{(1-6)}$alkyl, halo$C_{(1-6)}$alkyl, $C_{(1-6)}$alkyloxy, $NR^{17}R^{18}$, $(SO_2)R^{19}$ and $NH(C=O)R^{22}$], phenylcarbonyl, naphthyl and $C_{(1-14)}$heterocycle [where the heterocycle moiety is optionally substituted by one or more substituents independently selected from $C_{(1-6)}$alkyl, $C_{(1-6)}$alkyloxy, $C_{(1-6)}$alkyloxycarbonyl and $NR^{23}R^{24}$];
$R^1$ is selected from hydrogen, halo, $C_{(1-6)}$alkyl, $C_{(1-6)}$alkyloxy, $C_{(3-6)}$cycloalkyloxy, halo$C_{(1-6)}$alkyl, cyano, nitro and hydroxy;
$R^2$ is selected from hydrogen and $C_{(1-6)}$alkyloxy;
$R^3$ is hydrogen;
$R^4$ is selected from hydrogen and $C_{(1-6)}$alkyl [where the alkyl moiety may be optionally substituted by hydroxy];
$R^5$ is selected from hydrogen, hydroxy, $C_{(1-6)}$alkyl and cyano;
$R^6$ is selected from hydrogen, hydroxy, $C_{(1-6)}$alkyl [where the alkyl moiety may be optionally substituted by one or more substituents independently selected from $NR^{17}R^{18}$ and $C_{(1-14)}$heterocycle (where the heterocycle moiety is optionally substituted by $C_{(1-6)}$alkyl)], $C_{(2-6)}$alkynyl, $C_{(1-6)}$alkyloxy [where the alkyloxy moiety may be optionally substituted by $C_{(1-6)}$alkyloxy], (C=O)$R^{16}$, aminocarbonyloxy, $N_3$, phenyl [where the phenyl moiety may be optionally substituted by halo] and $C_{(1-14)}$heterocycle [where the heterocycle moiety is optionally substituted by one or more substituents independently selected from $NR^{23}R^{24}$ and phenyl];
or
$R^5$ and $R^6$ together can form 1,3-dioxolanyl;
$R^7$, $R^9$ and $R^{10}$ are hydrogen;
$R^8$ and $R^{13}$ are each independently selected from hydrogen and $C_{(1-6)}$alkyl;
$R^{11}$ is selected from hydroxy and $C_{(1-6)}$alkyloxy [where the alkyloxy moiety may be optionally substituted by (C=O)$NR^{17}R^{18}$];

$R^{12}$ is selected from hydrogen and hydroxy;
$R^{14}$ is selected from hydrogen and $C_{(1-6)}$alkyl;
$R^{15}$ is selected from hydrogen, $C_{(1-6)}$alkyl [where the alkyl moiety may optionally be substituted by one or more substituents independently selected from $C_{(1-6)}$alkyloxy, $C_{(3-6)}$cycloalkyl and $C_{(1-14)}$heterocycle], $C_{(1-6)}$alkyloxy, phenyl and $C_{(1-14)}$heterocycle [where the heterocycle moiety is optionally substituted by one or more substituents independently selected from hydroxy, $C_{(1-6)}$alkyl, $C_{(1-6)}$alkyloxy, $C_{(1-6)}$alkyloxycarbonyl, $(SO_2)R^{19}$ and $C_{(1-14)}$heterocycle];
or
$R^{14}$ and $R^{15}$ together with the N atom to which they are attached form a 3, 4, 5 or 6 membered heterocyclic ring optionally substituted by 1,2 or 3 substituents independently selected from phenyl, phenyl$C_{(1-6)}$alkyl and (C=O)$R^{16}$;
$R^{16}$ is selected from hydrogen, hydroxy, $C_{(1-6)}$alkyl [where the alkyl moiety may be optionally substituted by one or more substituents independently selected from halo, $NR^{17}R^{18}$, phenyl and $Het^1$], $C_{(1-6)}$alkenyl, phenyl$C_{(2-6)}$alkenyl, $C_{(1-6)}$alkyloxy, fluorene$C_{(1-6)}$alkyloxy, phenyloxy, $NR^{17}R^{18}$, $Ar^1$ and $Het^1$;
$R^{17}$ is selected from hydrogen, hydroxy, $C_{(1-6)}$alkyl, $C_{(3-6)}$cycloalkyl, $C_{(1-6)}$alkyloxy-$C_{(1-6)}$alkyl, aminocarbonyl$C_{(1-6)}$alkyl and (C=O)$R^{19}$;
$R^{18}$ is selected from hydrogen, $C_{(1-6)}$alkyl [where the alkyl moiety may be optionally substituted by one or more substituents independently selected from $C_{(3-6)}$cycloalkyl, (C=O)$R^{19}$, $Ar^1$ and $Het^1$], $C_{(2-6)}$alkynyl [where the alkynyl moiety may be optionally substituted by phenyl], $C_{(3-6)}$cycloalkyl, (C=O)$R^{19}$, $(SO_2)R^{19}$, $Ar^1$ and $Ht^1$;
or
$R^{17}$ and $R^{18}$ together with the N atom to which they are attached form a 3, 4, 5 or 6 membered heterocyclic ring optionally substituted by 1, 2 or 3 substituents independently selected from hydroxy, $C_{(1-6)}$alkyl [where the alkyl moiety may be optionally substituted by one or more substituents independently selected from hydroxy, $C_{(1-6)}$alkyloxy, (C=O)$R^{19}$, $Ar^1$ and $Het^1$], $C_{(3-6)}$cycloalkyl, amino, (C=O)$R^{19}$, S—$Ar^1$, $Ar^1$ and $Het^1$;
$R^{19}$ is selected from $C_{(1-6)}$alkyl [where the alkyl moiety may be optionally substituted by one or more substituents independently selected from halo, phenyl, $C_{(1-6)}$alkyloxycarbonyl, $NR^{20}R^{21}$ and $Het^1$], $C_{(2-6)}$alkynyl [where the alkynyl moiety may be optionally substituted by phenyl], $C_{(1-6)}$alkyloxy, fluorene$C_{(1-6)}$alkyloxy, phenyloxy, amino, $Ar^1$ and $Het^1$;
$R^{20}$ is selected from hydrogen and $C_{(1-6)}$alkyl;
$R^{21}$ is a selected from hydrogen, $C_{(1-6)}$alkyl, $C_{(3-6)}$cycloalkyl, $C_{(1-6)}$alkyloxycarbonyl, phenyl and $Het^1$;
$Ar^1$ is a $C_{(6-14)}$aryl substituted by one or more substituents independently selected from halo, cyano, $C_{(1-6)}$alkyl, $C_{(1-6)}$alkyloxy, phenyl$C_{(1-6)}$alkyloxy, phenyloxy, halophenyloxy, halo$C_{(1-6)}$alkyl and (C=O)$R^{22}$, $(SO_2)R^{22}$, $NH(C=O)R^{22}$ and $NR^{23}R^{24}$;
$Het^1$ is a $C_{(1-14)}$heterocycle substituted by one or more substituents independently selected from hydroxy, $C_{(1-6)}$alkyl, phenyl$C_{(1-6)}$alkyl, amino$C_{(1-6)}$alkyl, $C_{(1-6)}$alkylamino$C_{(1-6)}$alkyl, (=O), (=NH), $NH(C=O)R^{22}$, $NR^{23}R^{24}$ and phenyl;
$R^{22}$ is selected from hydrogen, hydroxy, $C_{(1-6)}$alkyl, $C_{(1-6)}$alkyloxy, halo$C_{(1-6)}$alkyl, $NR^{23}R^{24}$ and

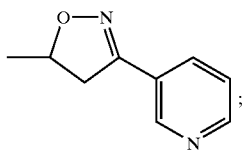

$R^{23}$ and $R^{24}$ are each independently selected from hydrogen, $C_{(1-6)}$alkyl and

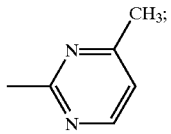

or a N-oxide, addition salt, quaternary amine or stereochemically isomeric form thereof;

As used herein $C_{(1-3)}$alkyl as a group or part of a group defines straight or branched chain saturated hydrocarbon radicals having from 1 to 3 carbon atoms such as methyl, ethyl, propyl, 1-methylethyl, and the like; $C_{(1-4)}$alkyl as a group or part of a group defines straight or branched chain saturated hydrocarbon radicals having from 1 to 4 carbon atoms such as the groups defined for $C_{(1-3)}$alkyl, butyl, isopropyl and the like, $C_{(1-6)}$alkyl as a group or part of a group defines straight or branched chain saturated hydrocarbon radicals having from 1 to 6 carbon atoms such as the groups defined for $C_{(1-4)}$alkyl and pentyl, hexyl, 2-methylpropyl, 2-methylbutyl and the like; $C_{(3-6)}$cycloalkyl is generic to cyclo-propyl, cyclobutyl, cyclopentyl and cyclohexyl; $C_{(2-3)}$alkenyl defines straight and branched chain hydrocarbon radicals having from 2 to 3 carbon atoms containing a double bond, such as ethenyl or propenyl; $C_{(2-4)}$alkenyl defines straight and branched chain hydrocarbon radicals having from 2 to 4 carbon atoms containing a double bond, such as the groups defined for $C_{(2-3)}$alkenyl and butenyl, $C_{(2-6)}$alkenyl defines straight and branched chain hydrocarbon radicals having from 2 to 6 carbon atoms containing a double bond such as the groups defined for $C_{(2-4)}$alkenyl and pentenyl or hexenyl, $C_{(3-6)}$cycloalkenyl is generic to cyclopropenyl, cyclobutenyl, cyclopentenyl and cyclohexenyl. As used herein the term $C_{(2-3)}$alkynyl defines straight and branched chain hydrocarbon radicals having 2 to 3 atoms containing a triple bond, such as ethynyl or propynyl; $C_{(2-6)}$alkynyl defines straight and branched chain hydrocarbon radicals having from 2 to 6 carbon atoms containing a triple bond such as the groups defined for $C_{(2-3)}$alkynyl and butynyl, pentynyl or hexynyl. The term $C_{(1-3)}$alkyloxy defines straight or branched chain saturated hydrocarbon radicals such as methoxy, ethoxy, or propyloxy. $C_{(1-6)}$alkyloxy defines straight or branched chain saturated hydrocarbon radicals such as the groups defined for $C_{(1-3)}$ alkyloxy and butyloxy, pentyloxy, hexyloxy, 1-methylethyloxy, 2-methylpropyloxy, 2-methylbutyloxy and the like; $C_{(3-6)}$cycloalkyloxy is generic to cyclopropyloxy, cyclobutyloxy, cyclopentyloxy and cyclohexyloxy.

As used herein before, the term (=)) forms a carbonyl moiety with the carbon atom to which it is attached. The term (=NH) forms a imino moiety with the carbon atom to which it is attached.

The term halo is generic to fluoro, chloro, bromo and iodo. As used in the foregoing and hereinafter, halo$C_{(1-6)}$ alkyl is defined as mono- or polyhalosubstituted $C_{(1-6)}$alkyl, in particular $C_{(1-6)}$alkyl substituted with one or more fluor atoms, for example trifluoromethyl.

The term $C_{(6-14)}$aryl as a group or part of a group defines carbocyclic radicals containing one or more rings which may be independently saturated, partially saturated or unsaturated. The term covers fused ring systems as well as systems which are connected through a linking group, e.g. —N—, —C—, —O—, —S—, or a bond. Examples of such groups are phenyl, biphenyl, fluorenyl or naphthyl. $C_{(6-14)}$ arylidene is a bivalent $C_{(6-14)}$aryl radical as described supra.

The term $C_{(2-14)}$carbocyclic radical as a group or part of a group defines carbocyclic radicals containing one or more rings (including 3, 4, 5 or 6 membered carbocyclic rings) which may be independently saturated, partially saturated, unsaturated, including aromatic. The term covers fused ring systems as well as systems which are connected through a linking group, e.g. —N—, —C—, —O—, —S—, or a bond.

The term $C_{(1-14)}$heterocycle defines one or more rings (including 3, 4, 5 or 6 membered heterocyclic rings) which may be independently saturated, partially saturated, unsaturated, including aromatic, containing one or more (for example 1, 2, 3 or 4) heteroatoms selected from N, O and S. Examples of such groups include indanyl, pyridinyl, tetrahydropyridinyl isothiazolyl, pyrrolyl, triazolylphenyl, piperidinyl, thiazolyl, piperazinyl, isoxazolyl, pyrazolyl, morpholinyl, imidazolyl, oxadiazolyl, dioxolanyl, pyrimidinyl, dihyropyrimidinyl, oxazolidinyl, benzimidazolyl, benzothiazolyl, benzodioxolanyl, benzopyridinyl, benzopyranyl, furanyl, thionyl, triazospirodecanyl, isoquinolinyl or tetrazolyl. $C_{(1-14)}$ heterocylidene is a bivalent $C_{(1-14)}$heterocyclic radical as described supra.

As used herein before, the term "one or more" covers the possibility of all the available C-atoms, where appropriate, to be substituted, preferably 1, 2 or 3.

Het[1] is meant to include all the possible isomeric forms of the heterocycles mentioned in the definition of Het[1] for instance, pyrrolyl also includes 2H-pyrrolyl, pyranyl includes 2H-pyranyl and 4H-pyranyl.

The $C_{(1-14)}$heterocycle represented by Het[1] may be attached to the remainder of the molecule of formula (I) through any ring carbon or heteroatom as appropriate. Thus, for example, when the heterocycle is imidazolyl, it may be a 1-imidazolyl, 2-imidazolyl, 4-imidazolyl and 5-imidazolyl; when it is thiazolyl, it may be 2-thiazolyl, 4-thiazolyl and 5-thiazolyl; when it is triazolyl, it may be 1,2,4-triazol-1-yl, 1,2,4-triazol-3-yl, 1,2,4-traizol-5-yl, 1,3, 4-triazol-1-yl and 1,3,4-triazol-2-yl; when it is benzthiazolyl, it may be 2-benzthiazolyl, 4-benzthiazolyl, 5-benzthiazolyl, 6-benzthiazolyl and 7-benzthiazolyl.

When any variable (eg. Ar, Het, $R^1$, $R^2$ etc.) occurs more than one time in any constituent, each definition is independent.

Lines drawn into ring systems from substituents indicate that the bond may be attached to any of the suitable ring atoms.

It will be appreciated that some of the compounds of formula (I) and their N-oxides, addition salts, quaternary amines and stereochemically isomeric forms may contain one or more centers of chirality and exist as stereochemically isomeric forms.

The term "stereochemically isomeric forms" as used hereinbefore defines all the possible stereoisomeric forms which the compounds of formula (I), and their N-oxides, addition salts, quaternary amines or physiologically functional derivatives may possess. Unless otherwise mentioned or indicated, the chemical designation of compounds denotes the mixture of all possible stereochemically isomeric forms, said mixtures containing all diastereomers and enantiomers of the basic molecular structure as well as each of the individual isomeric forms of formula (I) and their N-oxides, salts, solvates or quaternary amines substantially free, i.e. associated with less than 10%, preferably less than 5%, in particular less than 2% and most preferably less than 1% of the other isomers. In particular, stereogenic centers may have the R- or S-configuration; substituents on bivalent cyclic (partially) saturated radicals may have either the cis- or trans-configuration. Compounds encompassing double bonds can have an E or Z-stereochemistry at said double bond. Stereochemically isomeric forms of the compounds of formula (I) are obviously intended to be embraced within the scope of this invention.

Compounds of formula (I) as defined supra of particular interest include those where the asymmetric carbon atom indicated with an * has an S-configuration.

For some of the compounds of formula (I), their N-oxides, salts, solvates or quaternary amines and the intermediates used in the preparation thereof, the absolute stereochemical configuration was not experimentally determined. In these cases the stereoisomeric form which was first isolated is designated as "A" and the second as "B", without further reference to the actual stereochemical configuration. However, said "A" and "B" stereoisomeric forms can be unambiguously characterized by for instance their optical rotation in case "A" and "B" have an enantiomeric relationship. A person skilled in the art is able to determine the absolute configuration of such compounds using art-known methods such as, for example, X-ray diffraction. In case "A" and "B" are stereoisomeric mixtures, they can be further separated whereby the respective first fractions isolated are designated "A1" and "B1" and the seconds as "A2" and "B2", without further reference to the actual stereochemical configuration.

For therapeutic use, salts of the compounds of formula (I) are those wherein the counterion is pharmaceutically acceptable. However, salts of acids and bases which are non-pharmaceutically acceptable may also find use, for example, in the preparation or purification of a pharmaceutically acceptable compound. All salts, whether pharmaceutically acceptable or not are included within the ambit of the present invention.

The pharmaceutically acceptable acid and base addition salts as mentioned hereinabove are meant to comprise the therapeutically active non-toxic acid and base addition salt forms which the compounds of formula (I) are able to form. The pharmaceutically acceptable acid addition salts can conveniently be obtained by treating the base form with such appropriate acid. Appropriate acids comprise, for example, inorganic acids such as hydrohalic acids, e.g. hydrochloric or hydrobromic acid, sulfuric, nitric, phosphoric and the like acids; or organic acids such as, for example, acetic, propanoic, hydroxyacetic, lactic, pyruvic, oxalic (i.e. ethanedioic), malonic, succinic (i.e. butane-dioic acid), maleic, fumaric, malic, tartaric, citric, methanesulfonic, ethanesulfonic, benzenesulfonic, p-toluenesulfonic, cyclamic, salicylic, p-aminosalicylic, pamoic and the like acids.

Conversely said salt forms can be converted by treatment with an appropriate base into the free base form.

The compounds of formula (I) containing an acidic proton may also be converted into their non-toxic metal or amine addition salt forms by treatment with appropriate organic and inorganic bases. Appropriate base salt forms comprise, for example, the ammonium salts, the alkali and earth alkaline metal salts, e.g. the lithium, sodium, potassium, magnesium, calcium salts and the like, salts with organic bases, e.g. the benzathine, N-methyl-D-glucamine, hydrabamine salts, and salts with amino acids such as, for example, arginine, lysine and the like.

The term addition salt as used hereinabove also comprises the solvates which the compounds of formula (I) as well as the salts thereof, are able to form. Such solvates are for example hydrates, alcoholates and the like.

Some of the compounds of formula (I) may also exist in their tautomeric form. Such forms although not explicitly indicated in the above formula are intended to be included within the scope of the present invention. For instance, when an aromatic heterocyclic ring is substituted with hydroxy the keto-form may be the mainly populated tautomer.

Preferred embodiments of the present invention include compounds of formula (I) wherein one or more of the following restrictions apply:
 (i) B is a group of formula (b-2);
 (ii) —A$^1$=A$^2$—A$^3$=A$^4$— is a radical of formula (a-1);
 (iii) groups R$^1$, R$^2$, R$^3$ and R$^4$ are hydrogen;
 (iv) m and n are 0 and p is 0 or 1;
 (v) D is Ar$^1$ [wherein Ar$^1$ is preferably phenylidene (wherein the phenylidene moiety may be optionally substituted with halo)] or Het$^1$ [wherein Het$^1$ is preferably pyridinylidene];
 (vi) L is Ar$^1$ [wherein Ar$^1$ is most preferably phenyl {wherein the phenyl moiety may be optionally substituted with one or more substituents, preferably 1, 2 or 3 substituents, independently selected from halo, C$_{(1-3)}$alkyloxy, C$_{(1-3)}$alkyl (wherein the alkyl moiety may be optionally substituted with one or more halo, preferably substituted with 3 F substituents), NR$^{23}$R$^{24}$ (wherein R$^{23}$ and R$^{24}$ are preferably independently selected from hydrogen and C$_{(1-3)}$alkyl), (C=O)R$^{22}$ (wherein R$^{22}$ is preferably NR$^{23}$R$^{24}$ (wherein R$^{23}$ and R$^{24}$ are preferably independently selected from hydrogen and C$_{(1-3)}$alkyl)), (SO$_2$)R$^{22}$ (wherein R$^{22}$ is preferably C$_{(1-3)}$alkyl (wherein the alkyl moiety may be optionally substituted with one or more halo)) and NH(C=O)R$^{22}$ (wherein R$^{22}$ is preferably

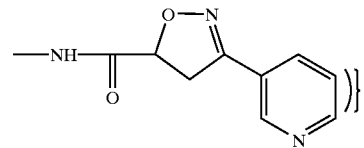

or naphtalenyl] or Het$^1$ [wherein Het$^1$ is preferably selected from pyridinyl, furanyl, thiophenyl, benzodioxolanyl, quinolinyl and 1,3,4H-isoquinolinyl (wherein the 1,3,4H-isoquinolinyl moiety may be optionally substituted with one or more, preferably 1 or 2 C$_{(1-3)}$alkyloxy)];
 (vii) Q is preferably a bivalent radical of formula (c-1), (c-2), (c-3), (c-4), (c-5), (c-6), (c-7), (c-8), (c-9) or (c-10), most preferably, Q is a bivalent radical of formula (c-1), (c-3), (c-4), (c-5), (c-7) or (c-10).
  When
  1. Q is (C-2), X$_1$ is preferably S or O;
  2. Q is (c-3), R$^5$ is preferably selected from hydrogen, hydroxy and cyano;
   R$^6$ is preferably selected from hydrogen, hydroxy, (C=))OR$^{16}$, NR$^{17}$R$^{18}$, N$_3$, C$_{(1-3)}$alkyl [wherein the alkyl moiety may be optionally substituted with (=O), NR$^{17}$R$^{18}$,
   C$_{(1-3)}$alkyloxy, Ar$^1$ (wherein Ar$^1$ is preferably phenyl) or Het$^1$ (wherein Het$^1$ is preferably pyridinyl)], C$_{(1-3)}$ alkyloxy [wherein the alkyloxy moiety may be optionally substituted with (=)), $NR^{17}R^{18}$, $C_{(1-3)}$alkyloxy or $Ar^1$ (wherein $Ar^1$ is preferably phenyl)], $Ar^1$ [wherein $Ar^1$ is preferably phenyl] and $Het^1$ [wherein $Het^1$ is preferably pyridinyl or thiazolyl (wherein the thiazolyl may be optionally substituted with one or two substituents independently selected from amino and phenyl)];

$R^{16}$ is preferably $C_{(1-3)}$alkyl;

$R^{17}$ is preferably hydrogen;

$R^{18}$ is preferably selected from hydrogen, $C_{(3-6)}$cycloalkyl, $(C=O)R^{19}$, $C_{(1-3)}$alkyl [wherein the alkyl moiety is optionally substituted by $(C=O)R^{19}$ or $Het^1$ {wherein $Het^1$ is preferably benzimidazolyl (wherein the benzimidazolyl is preferably substituted with $C_{(1-3)}$alkyl), piperidine (wherein the piperidine is preferably substituted with $C_{(1-3)}$alkyl), pyridinyl, morpholinyl or 1,2-dioxolanyl}], $Ar^1$ [wherein $Ar^1$ is preferably phenyl {wherein the phenyl moiety is optionally substituted by one or more substituents, preferably 1, 2 or 3 substituents, independently selected form halo, hydroxy, $C_{(1-3)}$alkyloxy, $(C=O)R^{22}$, $NH(C=O)R^{22}$, $(SO_2)R^{22}$, $C_{(1-3)}$alkyl (wherein the alkyl moiety is optionally substituted by one or more halo), and $Het^1$ (wherein $Het^1$ is preferably piperidinyl)] and $Het^1$ [wherein $Het^1$ is preferably selected from pyridinyl, benzitriazolyl, benzimidazolyl (wherein the benzimidazolyl is preferably substituted with $C_{(1-3)}$alkyl), piperidinyl (wherein the piperidinyl moiety is preferably substituted with $C_{(1-3)}$alkyl, $C_{(1-3)}$alkylphenyl) or isoxazolyl (wherein the isoxazolyl is preferably substituted with $C_{(1-3)}$alkyl)];

or $R^{17}$ and $R^{18}$ together with the N atom to which they are attached preferably form an optionally substituted $C_{(1-14)}$heterocycle, preferably 2H-pyridine [wherein the 2H-pyridine is preferably substituted with (=NH)], morpholinyl, 1,3,4H-isoquinolinyl, piperidine [wherein the piperidine is preferably substituted with $C_{(1-3)}$alkyl (wherein the alkyl moiety may be optionally substituted with N-methylpiperazinyl) or piperidine];

$R^{19}$ is preferably selected from $C_{(1-3)}$alkyl [wherein the alkyl moiety may be optionally substituted with $NR^{20}R^{21}$, $Ar^1$ (wherein $Ar^1$ is preferably phenyl)], $NR^{20}R^{21}$ and $Ar^1$ [wherein $Ar^1$ is preferably phenyl (wherein the phenyl moiety is optionally substituted by one or more halo)];

$R^{20}$ is preferably selected from hydrogen and $C_{(1-3)}$alkyl;

$R^{21}$ is preferably selected from hydrogen and $Het^1$ [wherein $Het^1$ is preferably piperidinyl (wherein the piperidinyl moiety is preferably substituted with $C_{(1-3)}$alkyl)];

$R^{22}$ is preferably selected from $C_{(1-3)}$alkyl and $NR^{23}R^{24}$;

$R^{23}$ is preferably hydrogen;

$R^{24}$ is preferably hydrogen;

3. Q is (c-4), $R^7$ is preferably hydrogen;
4. Q is (c-5), $R^8$ is preferably hydrogen;
5. Q is (c-6), $R^9$ and $R^{10}$ are preferably hydrogen;
6. Q is (c-7), $R^{11}$ is preferably selected from hydroxy and $C_{(1-3)}$alkyloxy [wherein the alkyloxy moiety may be optionally substituted with $(C=O)R^{16}$];

$R^{16}$ is preferably $NR^{17}R^{18}$;

$R^{17}$ is preferably $C_{(1-3)}$alkyl;

$R^{18}$ is preferably $C_{(3-6)}$cycloalkyl;

7. Q is (c-8), t is preferably 1;

$R^{12}$ is preferably selected from hydrogen and hydroxy;

8. Q is (c-10), $X_2$ is preferably s or O, most preferably $X_2$ is O;

$R^{13}$ is preferably selected from hydrogen, $C_{(1-3)}$alkyl and $C_{(1-3)}$alkyloxy;

$R^{14}$ is preferably hydrogen;

$R^{15}$ is preferably selected from hydrogen, $C_{(1-3)}$alkyl [wherein the alkyl moiety may be optionally substituted with $Het^1$ (wherein $Het^1$ is preferably morpholinyl)] and $Het^1$ [wherein $Het^1$ is preferably piperidinyl (wherein the thiazolyl moiety is optionally substituted with $(C=)R^{22}$) or thiazolyl {wherein the thiazolyl moiety is optionally substituted with $C_{(1-3)}$alkyl (wherein the alkyl moiety is optionally substituted with $NR^{23}R^{24}$)}];

$R^{22}$ is preferably $C_{(1-3)}$alkyloxy;

$R^{23}$ is preferably $C_{(1-3)}$alkyl;

$R^{24}$ is preferably $C_{(1-3)}$alkyl;

or a N-oxide, addition salt, quaternary amine or stereochemically isomeric form thereof.

Particularly preferred compounds are those compounds of formula (I) wherein

B is a group of formula (b-2);

$—A^1=A^2—A^3=A^4—$ is a radical of formula (a-1);

groups $R^1$, $R^2$, $R^3$ and $R^4$ are hydrogen;

preferably m and n are 0 and p is 0 or 1;

D is $Ar^1$ [wherein $Ar^1$ is preferably phenylidene (wherein the phenylidene moiety may be optionally substituted with halo)];

L is $Ar^1$ [wherein $Ar^1$ is preferably phenyl {wherein the phenyl moiety may be optionally substituted with one or more substituents, preferably 1, 2 or 3 substituents, independently selected from halo, $C_{(1-3)}$alkyloxy, $C_{(1-3)}$alkyl, $(SO_2)R^{22}$ (wherein $R^{22}$ is preferably $C_{(1-3)}$alkyl (wherein the alkyl moiety may be optionally substituted with one or more halo), more preferably $R^{22}$ is trifluoromethyl), $NH(C=O)R^{22}$ (wherein $R^{22}$ is preferably

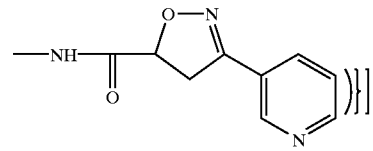

and $Het^1$ [wherein $Het^1$ is preferably pyridinyl or quinolinyl].

Q is most preferably is a bivalent radical of formula (c-1), (c-3), (c-4), (c-5), (c-7) or (c-10).

When

1. Q is (c-3), $R^5$ is most preferably selected from hydrogen, hydroxy and cyano;

$R^6$ is preferably selected from hydrogen, hydroxy, $C_{(1-3)}$alkyl, $C_{(1-3)}$alkyloxy and $NR^{17}R^{18}$;

$R^{17}$ is preferably hydrogen;

$R^{18}$ is preferably hydrogen;

2. Q is (c-4), $R^7$ is preferably hydrogen;
3. Q is (c-5), $R^8$ is preferably hydrogen;
4. Q is (c-7), $R^{11}$ is preferably selected from hydroxy and $C_{(1-3)}$alkyloxy [wherein the alkyloxy moiety is preferably substituted with $(C=O)R^{16}$];

$R^{16}$ is preferably $NR^{17}R^{18}$;

$R^{17}$ is preferably $C_{(1-3)}$alkyl;

$R^{18}$ is preferably $C_{(3-6)}$cycloalkyl;

5. Q is (c-10), $X_2$ is preferably O;

$R^{13}$ is preferably selected from hydrogen and $C_{(1-3)}$alkyl;

$R^{14}$ is preferably hydrogen;
$R^{15}$ is preferably selected from hydrogen and $C_{(1-3)}$alkyl;
or a N-oxide, addition salt, quaternary amine or stereochemically isomeric form thereof.

Most preferred compounds include:

N-(4-benzolyphenyl)-4,5-dihydro-3-(3-pyridinyl)-5-isoxazolecarboxamide;

(B)-N-(4-benzolyphenyl)-4,5-dihydro-3-(3-pyridinyl)-5-isoxazolecarboxamide;

(E)-4,5-dihydro-N-[4-(hydroxyimino)phenylmethyl]phenyl]-3-(3-pyridinyl)-5-isoxazolecarboxamide;

4,5-dihydro-N-[4-(hydroxyphenylmethyl)phenyl]-3-(3-pyridinyl)-5-isoxazolecarboxamide;

[5S(B)]-4,5-dihydro-N-[4-(hydroxyphenylmethyl)phenyl]-3-(3-pyridinyl)-5-isoxazolecarboxamide;

4,5-dihydro-N-[4-(phenylmethyl)phenyl]-3-(3-pyridinyl)-5-isoxazolecarboxamide;

N-[4-(aminophenylmethyl)phenyl]-4,5-dihydro-3-(3-pyridinyl)-5-isoxazolecarboxamide;

[5S(A)]-N-[4-(aminophenylmethyl)phenyl]-4,5-dihydro-3-(3-pyridinyl)-5-isoxazolecarboxamide;

N-[4-(cyanophenylmethyl)phenyl]-4,5-dihydro-3-(3-pyridinyl)-5-isoxazolecarboxamide;

4,5-dihydro-N-[4-(4-methoxybenzoyl)phenyl]-3-(3-pyridinyl)-5-isoxazolecarboxamide;

4,5-dihydro-N-[(4-(methoxyphenylmethyl)phenyl]-3-(3-pyridinyl)-5-isoxazolecarboxamide;

4,5-dihydro-3-(3-pyridinyl)-N-[4-[[(2-pyridinylmethyl)amino]carbonyl]phenyl]-5-isoxazolecarboxamide;

(±)-[cyano-[4-[[[4,5-dihydro-3-(3-pyridinyl)-5-isoxazolyl]carbonyl]amino]-phenyl]phenylmethyl] acetate;

(±)-(E)-4,5-dihydro-N-[4-(1-oxo-3-phenyl-2-propenyl)phenyl]-3-(3-pyridinyl)-5-isoxazolecarboxamide;

(±)-N-[4-(3,4-dimethoxybenzoyl)phenyl]-4,5-dihydro-3-(3-pyridinyl)-5-isoxazolecarboxamide;

(±)-N-[4-(2,4-difluorobenzoyl)phenyl]-4,5-dihydro-3-(3-pyridinyl)-5-isoxazolecarboxamide;

(±)-N-[4-(4,5-dihydro-1-methyl-3-phenyl-1H-pyrazol-5-yl)phenyl-4,5-dihydro-3-(3-pyridinyl)-5-isoxazolecarboxamide;

(±)-N-[4-[(2,4-difluorophenyl)hydroxymethyl]phenyl]-4,5-dihydro-3-(3-pyridinyl)-5-isoxazolecarboxamide;

(B)-4,5-dihydro-3-(3-pyridinyl)-N-[4-(2-pyridinylcarbonyl)phenyl]-5-isoxazolecarboxamide;

(B2)-4,5-dihydro-N-[4-(hydroxy-2-pyridinylmethyl)phenyl]-3-(3-pyridinyl)-5-isoxazolecarboxamide;

or a N-oxide, addition salt, the quaternary amine or stereochemically isomeric form thereof;

The present invention further includes the following processes for the preparation of a compound of formula (I) or stereoisomers, a N-oxide, a salt, a quaternary amine or a solvate thereof.

In this and the following preparations, the reaction products may be isolated from the reaction medium and, if necessary, further purified according to methodologies generally known in the art, for example, extraction, crystallization, distillation, trituration and chromatography.

In the following description, the symbols $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, B, D, Q, L, m, n, p and t have the meaning ascribed to them in formula (I) unless otherwise stated.

In order to simplify the structural representation of the compounds of formula (I), the group

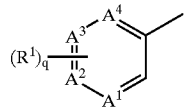

wherein $-A^1=A^2-A^3=A^4-$, $R^1$ and q is as defined before, will hereinafter be represented by the symbol Z.

Compounds of formula (I) wherein B is formula (b-2), represented by formula (I-a) below, can generally be prepared by reacting an intermediate of formula (II) wherein $W^1$ is $C_{(1-3)}$alkyloxy, hydroxy or a halogen atom, with an appropriate reagent of formula (III).

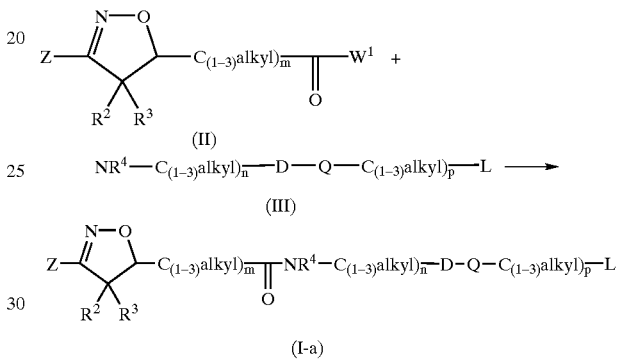

Said reaction can be performed in a reaction inert solvent, such as, chloroform, dichloroethane, dimethylformamide, tetrahydrofuran or a mixture thereof, and optionally in the presence of a suitable base, for example, N,N-dimethylpyridinamine or triethylamine. Convenient reaction temperatures range between 0° C. and 100° C.

Compounds of formula (III) can be obtained commercially or they can be made by methods well known in the art. Typically, compounds of formula (III) can be prepared by reacting a compound of formula HQ—$(C_{(1-3)}$alkyl$)_p$—L with a compound of formula $NO_2$—$(C_{(1-3)}$alkyl$)_n$—$DW^2$ wherein $W^2$ is a suitable leaving group, for example, a halogen atom. The nitro group can be converted in a amine by hydrogenation. Said reaction can be performed in a reaction inert solvent, such as, ethanol and in the presence of a suitable catalyst, such as palladium on carbon.

Intermediates of formula (II) wherein $W^1$ is $C_{(1-3)}$ alkyloxy, said compound being represented by formula (II-a) below, can be prepared by cyclization. Said cyclization can be performed by reacting an intermediate of formula (IV) with a compound of formula

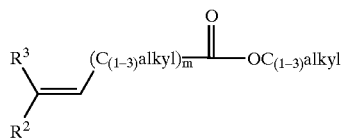

in a reaction inert solvent such as, dichloroethane in the presence of a base such as, triethylamine.

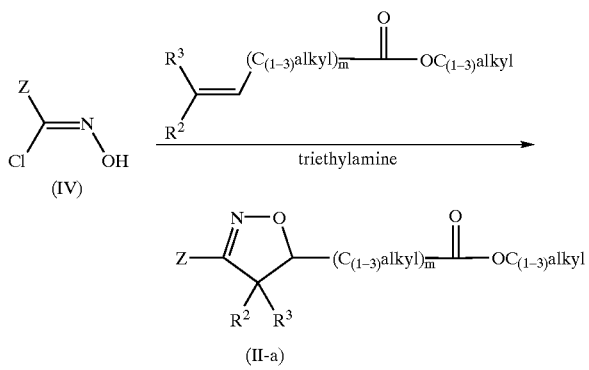

Intermediates of formula (IV) can be prepared by converting an aldehyde of formula (V) to an oxime of formula (VI), using art-known techniques, such as, using hydroxylamine hydrochloride in the presence of $NaHCO_3$ or pyridine in a solvent, for example, ethanol. The oxime is subsequently reacted with $Cl_{2(g)}$. Said reaction can be performed in a solvent, for example, chloroform or a mixture thereof. Convenient reaction temperatures range between 0° C. and room temperature.

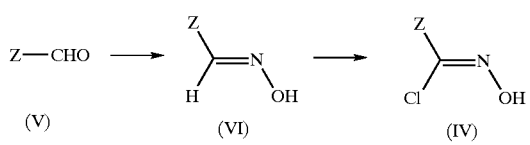

The intermediate of (II-a) can be conveniently converted into intermediates of formula (II) wherein $W^1$ is OH, represented by formula (II-b), using a suitable base, for example, NaOH, in a solvent, for example methanol. The intermediate of (II-b) can subsequently be converted into intermediates of formula (II) wherein $W^1$ is halo, represented by formula (II-c). A convenient procedure is converting the carboxylic acid group to the corresponding acid chloride atom using a suitable reagent such as, thionylchloride.

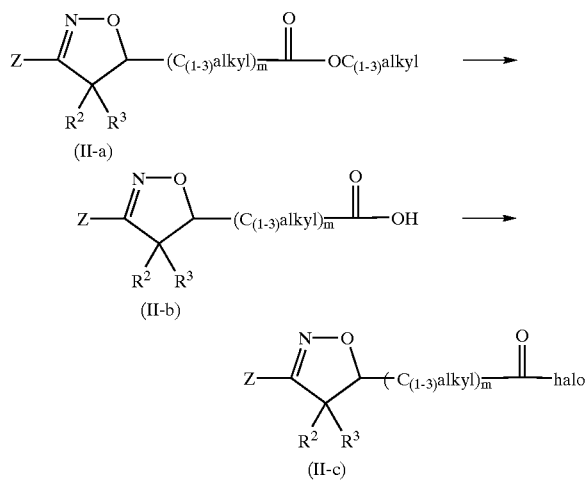

Compounds of formula (I) wherein B is a bivalent radical (b-1), (b-2) or (b-3) can be prepared by a 1,3-dipolar addition. Said addition reaction can be performed by reacting a compound of formula (IV) with an intermediate of formula

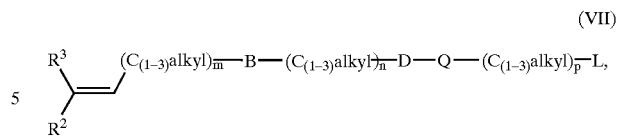

wherein B is (b-1), (b-2) or (b-3).

The reaction can be performed in a reaction inert solvent, for example dichloroethane or dimethylformamide in the presence of a base such as, triethylamine or pyridine. Convenient reaction temperatures range between 0° C. and 40° C.

When B is (b-1), the intermediate of formula (VII) can be prepared by reacting a compound of formula

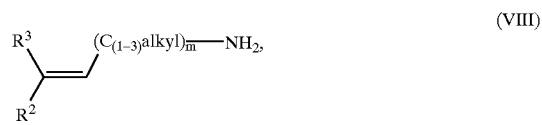

with an intermediate formula

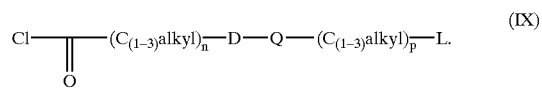

The compounds of formula (VIII) an (IX) can be obtained commercially or made using methods known in the art. Typically, compounds of formula (IX) can be prepared by converting the cyano group of an intermediate of formula

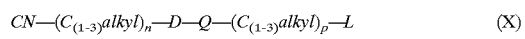

to a carboxyl group using, for example, a combination of sulfuric and acetic acid in water, which in turn can be further reacted to an acyl halide using thionyl chloride.

Compounds of formula (X) can be prepared as in J. Am. Chem. Soc. (1981), 103(3), 634–640.

The intermediate of formula (VII), wherein B is (b-2), can be made by reacting the amine of formula (III), supra, with a compound of formula

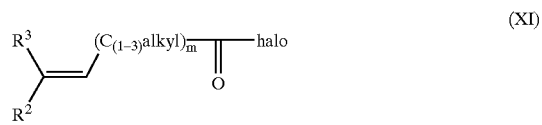

using methods known in the art.

Compounds of formula (VII) where B is (b-3) can be prepared by a two step substitution reactions as known in the art. Typically a compound of formula

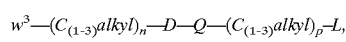

wherein $W^3$ is a suitable leaving group such as a halogen atom can be reacted with a compound of formula (XI). Suitable solvents are tetrahydrofuran, benzene or dimethylacetamide or a mixture thereof. The reaction can be performed in the presence of suitable catalysts such as, for example, Zn/Cu and Pd complexes. Convenient reaction temperatures range between 0° C. and 40° C.

Compounds of formula (I) wherein B is a bivalent radical of formula (b-4), (b-5) or (b-6), can conveniently be prepared by cyclization of a compound of formula

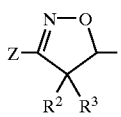

(XII)

where E represents

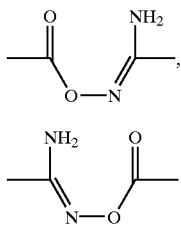

(e-1)

(e-2)

in paratoluene sulfonic acid and DMSO, at elevated temperature or where E represent

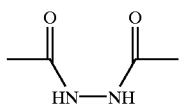

(e-3)

in POCl$_3$ at elevated temperature.

Compounds of formula (XII) wherein E is (e-1) can be prepared by reacting an intermediate of formula

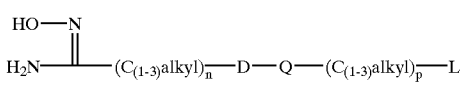

(XIII)

with a compound of formula (II-c), supra. The reaction can be performed in a reaction inert solvent, such as dichloromethane, and in the presence of a suitable base, for example diisopropylethylamine. Convenient reaction temperatures range between 5° C. and room temperature. Compounds of formula (XIII) can be prepared from a compound of formula (X), supra, by converting the cyano group to an amidoxime group using hydroxylamine hydrochloride using methods known in the art.

Compounds of formula (XII) wherein E is (e-3) can be prepared by reacting (II-c), supra, with a compound of formula

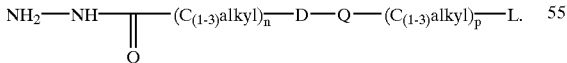

(XIV)

Compounds of formula (XIV) can be prepared by reacting a compound of formula with N$_2$H$_4$ in a reaction inert solvent such as dichloromethane, in the presence of a suitable base, for example, N,N-dimethyl-pyridinamine or diisopropylethaneamine.

Compounds of formula (XII) wherein E is (e-2) can be prepared by reacting a compound of formula (XVI) with an intermediate of formula (IX). The reaction can be performed in a reaction inert solvent, such as dichloromethane, and in the presence of a suitable base, for example diisopropylethylamine. Convenient reaction temperatures range between 0° C. and room temperature.

Compounds of formula (XVI) can be prepared from a nitrile derivative of formula (XV) by converting the cyano group to an amidoxime group using hydroxylamine hydrochloride or a functional derivative thereof using methods known in the art.

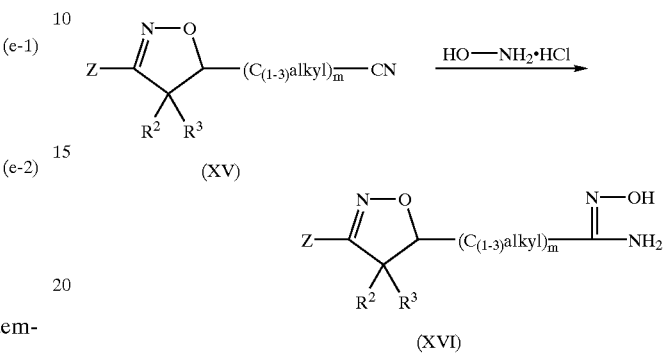

(XV)

(XVI)

Compounds of formula (XV) can be prepared by reacting an amidoxime of formula (VI) with 1-chloro-2,5-pyrrolidinedione and a compound of formula

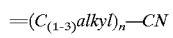

in a reaction inert solvent such as chloroform and in the presence of a suitable base, for example, pyridine, triethylamine or a mixture thereof.

Compounds of formula (I) wherein Q is a bivalent radical of formula (c-1), can generally be prepared by reacting an intermediate of formula (XVII) wherein W$^4$ is a suitable leaving group, for example, a halogen atom, with a compound of formula (XVIII). Said reaction can be performed in a reaction-inert solvent, for example, dichloroethane, preferably in the presence of a catalyst such as a trifurylphosphine-palladium (0) complex. The reaction is performed at an elevated temperature, ranging between 80° C. and 100° C.

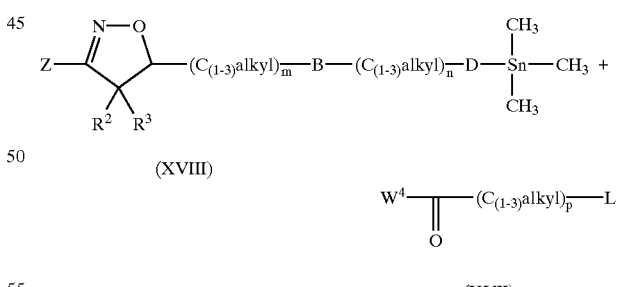

(XVIII)

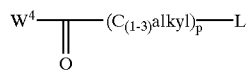

(XVII)

Intermediates of formula (XVII) can be obtained commercially or prepared by methods known in the art.

Intermediates of formula (XVIII) can be prepared by reacting a compound of formula (XIX), wherein W$^5$ is a suitable leaving group, for example, a halogen atom, with Sn$_2$(CH$_3$)$_6$. The reaction can be performed in a reaction inert solvent such as dioxane and in the presence of a suitable catalyst such as a Pd-complex. The reaction is performed at an elevated temperature, ranging between 80° C. and 100° C.

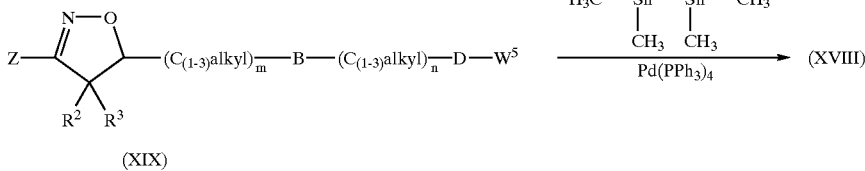

(XVIII)

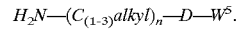

(XIX)

Compounds of formula (XIX) can be prepared by reacting compounds of formula (II-c) supra, with compounds of formula $H_2N-(C_{(1-3)}alkyl)_n-D-W^5$.

These compounds can be obtained commercially or prepared by methods known in the art.

Compounds of formula (I) wherein Q is of formula (c-5), (c-8) or (c-9) can conveniently be prepared by reacting an intermediate of formula

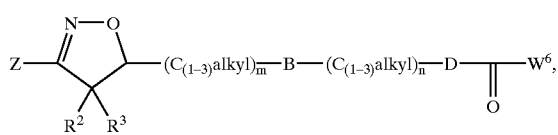

wherein $W^6$ is, for example, hydroxy or a halogen atom, with an appropriate functional primary or secondary amine derivative; For example, reacting with amines, such as

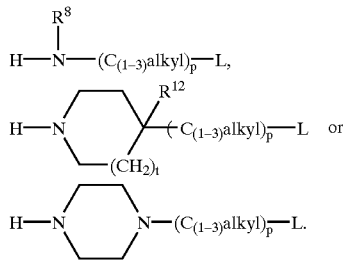

in a reaction inert solvent, for example, dichloromethane, dimethylformamide or a mixture thereof and in the presence of a suitable base such as diisopropylethylamine or triethylamine. Convenient reaction temperatures range between 0° C. and 50° C.

Compounds of formula (XX) can be prepared by reacting a compound of formula (II-c) supra, with a compound of formula

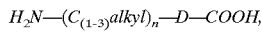

in a reaction inert solvent, such as, chloroform, dichloroethane, dimethylformamide, tetrahydrofuran or a mixture thereof, and optionally in the presence of a suitable base, for example, N,N-dimethyl-pyridinamine or triethylamine. Convenient reaction temperatures range between 0° C. and 100° C.

The resulting acid can subsequently be converted into a compound of formula (XX) using standard techniques.

Where necessary or desired, any one or more of the following further steps in any order may be performed:

(i) removing any remaining protecting group(s);

(ii) converting a compound of formula (I) or a protected form thereof into a further compound of formula (I) or a protected form thereof (iii) converting a compound of formula (I) or a protected form thereof into a N-oxide, a salt, a quaternary amine or a solvate of a compound of formula (I) or a protected form thereof;

(iv) converting a N-oxide, a salt, a quaternary amine or a solvate of a compound of formula (I) or a protected form thereof into a compound of formula (I) or a protected form thereof;

(v) converting a N-oxide, a salt, a quaternary amine or a solvate of a compound of formula (I) or a protected form thereof into another N-oxide, a pharmaceutically acceptable addition salt a quaternary amine or a solvate of a compound of formula (I) or a protected form thereof;

(vi) where the compound of formula (I) is obtained as a mixture of (R) and (S) enantiomers resolving the mixture to obtain the desired enantiomer.

Compounds of formula (I), N-oxides, addition salts, quaternary amines and stereochemical isomeric forms thereof can be converted into further compounds according to the invention using procedures known in the art, for example:

A.) Preparation of a compound of formula (I) wherein Q is a radical of formula (c-3) and $R^5$ is OH and $R^6$ is H, by reduction of the corresponding compound of formula (I), wherein Q is a radical of formula (c-1). The reaction is carried out in the presence of a suitable reducing agent, for example, sodiumborohydride in a suitable solvent, for example, water, an alcohol, tetrahydrofuran or a mixture thereof.

B.) Preparation of a compound of formula (I) wherein Q is a radical of formula (c-3), where $R^5$ is OH and $R^6$ is as defined in formula (I), by reacting the corresponding compound of formula (I), wherein Q is a radical of formula (c-1), with a compound of formula X-$R^6$, wherein X is halo and $R^6$ is as defined in formula (I), Said reaction is typically performed in a reaction inert solvent, for example, tetrahydrofuran, and in the presence of Mg. When X is Br, the reaction may conveniently be carried out in the presence of butyl lithium.

C) Preparation of a compound of formula (I) wherein Q is a radical of formula (c-3), where $R^5$ is $C_{(1-6)}$alkyloxy and $R^6$ is as defined in formula (I), by treating the corresponding compound of formula (I) wherein Q is a radical of formula (c-3), where $R^5$ is OH and $R^6$ is as defined in formula (I), using a suitable alkylating agent according to methods well known in the art.

D.) Preparation of a compound of formula (I) wherein Q is a radical of formula (c-3), where $R^6$ is as defined in formula (I) and $R^5$ is $NR^{17}R^{18}$ where $R^{17}$ and $R^{18}$ are as defined in formula (I), by reacting a compound of formula

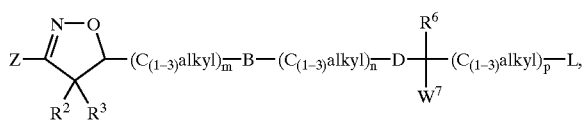

(XXI)

where $W^7$ is a leaving group such as, halo, $OSO_2CH_3$ or $OSO_2CF_3$, with an appropriate amine, for example, $NHR^{17}R^{18}$, in a reaction inert solvent, for example dimethylformamide and in the presence of a suitable base, such as, triethylamine. Compounds of formula (XXI) can be prepared from a compound of formula (I) wherein Q is a radical of formula (c-3), where $R^5$ is OH and $R^6$ is as defined in formula (I), by methods known in the chemical literature or well known to a skilled person.

E.) Preparation of a compound of formula (I) wherein Q is a radical of formula (c-3), where $R^6$ is as defined in formula (I) and $R^5$ is $NH_2$, by reacting a compound of formula (XXI) with a salt of a compound of formula

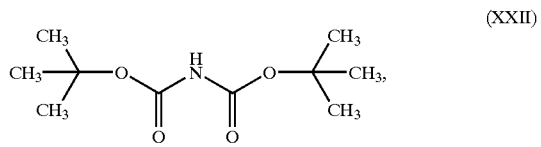

(XXII)

followed by an acid deprotection using trifluoroacetic acid. The reaction can be performed in a reaction inert solvent such as tetrahydrofuran or dichloromethane.

F.) Preparation of a compound of formula (I) wherein Q is a radical of formula (c-3), where $R^6$ is as defined in formula (I) and $R^5$ is $NHR^{18}$ where $R^{18}$ is $(C=O)R^{19}$ or $(SO_2)R^{19}$, by reacting the corresponding amino compound described in E.) above with a compound of formula $W^8$-$R^{18}$, where $W^8$ is a suitable leaving group, such as, halo and $R^{18}$ is $(C=O)R^{19}$ or $(SO_2)R^{19}$.

G.) Preparation of a compound of formula (I) wherein Q is a radical of formula (c-3), where $R^6$ is as defined in formula (I) and $R^5$ is $NHR^{18}$ where $R^{18}$ is $(C=O)CH_2R^{19}$ and $R^{19}$ is $NR^{20}R^{21}$, by reacting the corresponding compound of formula (I) wherein $R^{18}$ is a group $(C=O)CH_2$-halo with $HNR^{20}R^{21}$ in a reaction inert solvent, for example, tetrahydrofuran, dichloromethane, dimethylformamide or a mixture thereof.

H.) Preparation of a compound of formula (I) wherein Q is a radical of formula (c-3), where $R^6$ is as defined in formula (I) and $R^5$ is $NHR^{18}$ where $R^{18}$ is $(C=O)R^{19}$ and $R^{19}$ is $NHR^{21}$, by reacting a corresponding compound wherein $R^5$ is $NH_2$ with a compound of formula $R^{21}N=C=O$ in a suitable solvent, for example, tetrahydrofuran, dioxan, acetonitrile or a mixture thereof.

I.) Preparation of a compound of formula (I) wherein Q is a radical of formula (c=10) and $X_2$ is O, by reacting a compound of formula

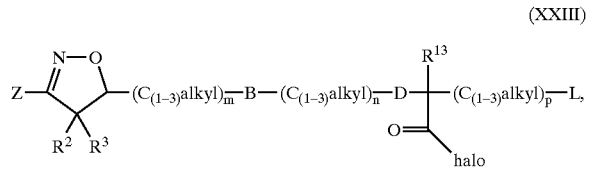

(XXIII)

with $HNR^{17}R^{18}$, in a reaction-inert solvent, for example, tetrahydrofuran, dichloromethane, dimethylformamide or a mixture thereof, preferably in the presence of a suitable base such as, for example diisopropylethylamine or triethylamine.

Compounds of formula (XXIII) can be prepared from a compound of formula (I) wherein Q is a radical of formula (c-3), where $R^5$ is cyano and $R^6$ is as defined in formula (I), by methods known in the chemical literature or well known to a skilled person.

J.) Preparation of a compound of formula (I) wherein Q is a radical of formula (c-6), where $R^9$ and $R^{10}$ are H, by reacting the corresponding compound of formula (I) wherein Q is a radical of formula (c-3), where $R^5$ is OH and $R^6$ is methyl with methylsulfonylchloride in the presence of a suitable base, such as, triethylamine, in a reaction inert solvent, for example, dichloromethane.

K.) Preparation of a compound of formula (I) wherein Q is a radical of formula (c-3), where $R^5$ is hydroxy and $R^6$ is $C_{(1-6)}$alkynyl, by reacting the corresponding compound of formula (I) wherein Q is a radical of formula (c-1) with a suitable reagent, such as, $Na^{+-}C\equiv C_{(1-5)}$alkyl, in a reaction inert solvent, for example, tetrahydrofuran.

L.) Preparation of a compound of formula (I) wherein Q is a radical of formula (c-3), where $R^5$ and $R^6$ together form 1,3-dioxalanyl, by reacting the corresponding compound of formula (I) wherein Q is a radical of formula (c-1) with 1,2-ethanediol in the presence of

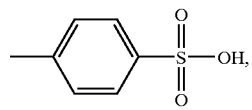

and a reaction inert solvent, for example, toluene.

M.) Preparation of a compound of formula (I) wherein Q is a radical of formula (c-3), where $R^6$ is as defined in formula (I) and $R^5$ is $O(C=O)NH_2$, by reacting the corresponding compound of formula (I) wherein Q is a radical of formula (c-3), where $R^5$ is hydroxy and $R^6$ is as defined in formula (I) with chlorosulfonyl isocyanate, in a reaction inert solvent, for example , dichloromethane.

N.) Preparation of a compound of formula (I) wherein Q is a radical of formula (c-10) wherein $X_2$ is S and $R^{14}$ and $R^{15}$ are H, by reacting a compound of formula (I) wherein Q is a radical of formula (c-3), where $R^6$ is as defined in formula (I) and $R^5$ is cyano, with $H_2S$ in the presence of a suitable base, such as, pyridine, triethylamine or a mixture thereof.

O.) Preparation of a compound of formula (I) wherein Q is a radical of formula (c-3), where $R^5$ is $C_{(1-6)}$alkyloxy and $R^6$ is as defined in formula (I), by reacting a compound of formula (I) wherein Q is a radical of formula (c-3), where $R^5$ is a halogen atom or other $R^5$ substituent which acts as a leaving group and $R^6$ is as defined in formula (I), with the corresponding hydroxy$C_{(1-6)}$alkyl.

P.) Preparation of a compound of formula (I) wherein Q is a radical of formula (c-3), where $R^5$ is $N_3$ and $R^6$ is as defined in formula (I), by reacting a compound of formula (I) wherein Q is a radical of formula (c-3), where $R^6$ is as defined in formula (I) and $R^5$ is $O(C=O)C_{(1-6)}$alkyl with $(CH_3)_3SiN_3$ in a reaction inert solvent such as dichloromethane in the presence of $SnCl_4$. The latter compound of formula (I) wherein $R^5$ is $O(C=O)C_{(1-6)}$alkyl can be prepared from the corresponding compound of formula (I) wherein $R^5$ is hydroxy, using acetic anhydride, in the presence of a suitable base, for example, pyridine.

Q.) Preparation of a compound of formula (I) wherein Q is a radical of formula (c-3), where $R^5$ is $OC_{(1-6)}$alkyl$OC_{(1-}$ $_{6)}$alkyl and $R^6$ is as defined in formula (I), by reacting a compound of formula (I) wherein Q is a radical of formula (c-3), where $R^6$ is as defined in formula (I) and $R^5$ is OSi(CH$_3$)$_3$, with $W^9C_{(1-6)}$alkylOC$_{(1-6)}$alkyl, wherein $W^9$ is a suitable leaving group, for example, a halogen atom. The reaction can be performed in a reaction inert solvent such as chloroform in the presence of P$_2$O$_5$. The latter compound of formula (I) where $R^5$ is OSi(CH$_3$)$_3$ can be prepared from the corresponding compound of formula (I) wherein Q is a radical of formula (c-1), using (CH$_3$)$_3$SiR$^6$.

R.) Compounds of formula (I) wherein Q is a radical of formula (c3), where $R^6$ is Het$^1$ and $R^5$ is as defined in formula (I), by cyclization of the corresponding compound of formula (I), wherein Q is a radical of formula (c3), where $R^5$ is CN and $R^6$ is azydyl. Said cyclization is performed in a reaction inert solvent such as tetrahydrofuran, methanol or mixture thereof and in the presence of a suitable reducing agent such as NaBH$_4$.

S.) Compounds of formula (I) where Q is a radical of formula (c3), wherein $R^5$ is CN and $R^6$ is C$_{1-6}$ alkyloxycarbonyloxy, by reacting the corresponding compound of formula (I), wherein Q is a radical of formula (c3), where $R^5$ is CN and $R^6$ is OH, using a compound of formula;

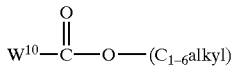

wherein $W^{10}$ is a leaving group such as, halo, OSO$_2$CH$_3$ or OSO$_2$CF$_3$ in the presence of a suitable base, such as, triethylamine, in a reaction inert solvent for example dicloromethane.

T.) Preparation of a compound of formula (I) wherein Q is a radical of formula (c3), where $R^5$ is as defined in formula (I) and $R^6$ is hydroxy C$_{(1-6)}$alkyl, by reacting a compound of formula (I) wherein Q is a radical of formula (c3), where $R^5$ is as defined in formula (I) and $R^6$ is C$_{(1-6)}$alkyl O C$_{(1-6)}$alkyl where the alkyloxy moiety may be optionally substituted by one or more substituents as defined in formula (I), with a hydrolizing agent such as HCl in a reaction inert solvent such as 1,4-dioxane.

U.) Preparation of a compound of formula (I) wherein Q is a radical of formula (c3), where $R^5$ is as defined in formula (I) and $R^6$ is hydroxy C$_{(1-6)}$alkyl, by reacting a compound of formula (I) wherein Q is a radical of formula (c3), where $R^5$ is as defined in formula (I) and $R^6$ is hydrogen, with (CH$_2$O)$_n$ using Triton B in the presence of a suitable base, for example pyridine.

V.) Preparation of a compound of formula (I) wherein Q is a radical of formula (c10), wherein X$_2$ is O and $R^{14}$ and $R^{15}$ are as defined in formula (I), where $R^{13}$ is Het$^1$, by reacting the corresponding compound of formula

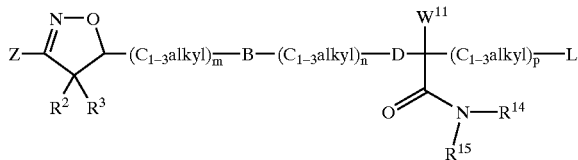

Wherein $W^{11}$ is a leaving group for example halo, with an appropriate amine such as NHR$^{17}$R$^{18}$.

It will be appreciated by those skilled in the art that in the processes described above the functional groups of intermediate compounds may need to be blocked by protecting groups.

Functional groups which it is desirable to protect include hydroxy, amino and carboxylic acid. Suitable protecting groups for hydroxy include trialkylsilyl groups (e.g. tert-butyldimethylsilyl, tert-butyldiphenylsilyl or trimethylsilyl), benzyl and tetrahydropyranyl. Suitable protecting groups for amino include tert-butyloxycarbonyl or benzyloxycarbonyl. Suitable protecting groups for carboxylic acid include C$_{(1-6)}$alkyl or benzyl esters.

The protection and deprotection of functional groups may take place before or after a reaction step.

The use of protecting groups is fully described in 'Protective Groups in Organic Chemistry', edited by J W F McOmie, Plenum Press (1973), and 'Protective Groups in Organic Synthesis' 2$^{nd}$ edition, T W Greene & P G M Wutz, Wiley Interscience (1991).

Additionally, the N-atoms in compounds of formula (I) can be methylated by art-known methods using CH$_3$I in a suitable solvent such as, for example 2propanone, tetrahydrofuran or dimethylformamide.

The compounds of formula (I) can also be converted into each other following art-known procedures of functional group transformation of which some examples are mentioned hereinabove.

The compounds of formula (I) may also be converted to the corresponding N-oxide forms following art-known procedures for converting a trivalent nitrogen into its N-oxide form. Said N-oxidation reaction may generally be carried out by reacting the starting material of formula (I) with 3-phenyl-2-(phenylsulfonyl)oxaziridine or with an appropriate organic or inorganic peroxide. Appropriate inorganic peroxides comprise, for example, hydrogen peroxide, alkali metal or earth alkaline metal peroxides, e.g. sodium peroxide, potassium peroxide; appropriate organic peroxides may comprise peroxy acids such as, for example, benzenecarboperoxoic acid or halo substituted benzenecarboperoxoic acid, e.g. 3-chlorobenzenecarboperoxoic acid, peroxoalkanoic acids, e.g. peroxoacetic acid, alkylhydroperoxides, e.g. t-butyl hydroperoxide. Suitable solvents are, for example, water, lower alkanols, e.g. ethanol and the like, hydrocarbons, e.g. toluene, ketones, e.g. 2-butanone, halogenated hydrocarbons, e.g. dichloromethane, and mixtures of such solvents.

Pure stereochemically isomeric forms of the compounds of formula (I) may be obtained by the application of art-known procedures. Diastereomers may be separated by physical methods such as selective crystallization and chromatographic techniques, e.g. counter-current distribution, liquid chromatography and the like.

Some of the compounds of formula (I) and some of the intermediates in the present invention may contain an asymmetric carbon atom. Pure stereochemically isomeric forms of said compounds and said intermediates can be obtained by the application of art-known procedures. For example, diastereoisomers can be separated by physical methods such as selective crystallization or chromatographic techniques, e.g. counter current distribution, liquid chromatography and the like methods. Enantiomers can be obtained from racemic mixtures by first converting said racemic mixtures with suitable resolving agents such as, for example, chiral acids, to mixtures of diasteromeric salts or compounds; then physically separating said mixtures of diastereomeric salts or compounds by, for example, selective crystallization or chromatographic techniques, e.g. liquid chromatography and the like methods; and finally converting said separated diastereomeric salts or compounds into the corresponding enantiomers. Pure stereochemically isomeric forms may also be obtained from the pure stereochemically isomeric forms of the appropriate intermediates and starting materials, provided that the intervening reactions occur stereospecifically.

An alternative manner of separating the enantiomeric forms of the compounds of formula (I) and intermediates involves liquid chromatography, in particular liquid chromatography using a chiral stationary phase.

Some of the intermediates and starting materials as used in the reaction procedures mentioned hereinabove are known compounds and may be commercially available or may be prepared according to art-known procedures.

The compounds of the present invention are useful because they possess pharmacological properties. They can therefore be used as medicines.

The growth inhibitory effect of the present compounds has been demonstrated by in vitro proliferation assays on human phytohemagglutinin stimulated white blood of which the test results for growth inhibition are presented in the experimental part hereinafter. Growth inhibition was also demonstrated in vitro on human keratinocytes.

Accordingly, the present invention provides the compounds of formula (I) and their pharmaceutically acceptable N-oxides, addition salts, quaternary amines and stereochemically isomeric forms for use in therapy. More particular in the treatment or prevention of T cell mediated diseases. The compounds of formula (I) and their pharmaceutically acceptable N-oxides, addition salts, quaternary amines and the stereochemically isomeric forms may hereinafter be referred to as compounds according to the invention.

Disorders for which the compounds according to the invention are particularly useful are rheumatic diseases like rheumatoid arthritis, juvenile arthritis and osteoarthritis; systemic inflammatory disease like systemic lupus erythematosis; psoriasis and psoriatic arthritis; T cell leukemia; transplant rejection and graft-versus-host disease.

Other therapeutic uses (particularly human therapeutic uses) for the compounds of formula (I) and their pharmaceutically acceptable salts and solvates include the treatment of conditions outlined in table 1.

TABLE 1

List of some T lymphocyte mediated pathologies

| | |
|---|---|
| Multiple sclerosis and other demyelinating diseases | Sézary syndrome and other T cell proliferative disorders |
| Crohn's disease | Hashimoto's syndrome |
| Ulcerative colitis | Graves' disease |
| Atopic dermatitis | Graves' opthalmopathy |
| Contact dermatitis | Simmonds' panhypopituitarism |
| Scleroderma | Primary biliary cirrhosis |
| Erythema nodosum | Polymyocistis |
| Mycosis fungoides | Myocarditis |
| Sarcoidosis boeck | Gout |
| Multiple myeloma | Reiters syndrome |
| Some B cell lymphomas | Uveitis |
| Aplastic anemia | Bechet's disease |
| Idiopathic thrombocytopenic purpura | Sjörgen's syndrome |
| Pemphigus vulgaris | Various clinical syndromes with vasculitis |
| Pemphigoid | Disseminated intravascular coagglutination |
| Insulin dependent diabetes | Arteriosclerosis |
| Addison's disease | Shock |
| Subcutane thyreoditis | Cachexia |

In view of the utility of the compounds according to the invention, there is provided a method for the treatment of an animal, for example, a mammal including humans, suffering from T cell mediated diseases, in particular T cell blast mediated disorders such as rheumatic diseases like rheumatoid arthritis, juvenile arthritis and osteoarthritis; systemic inflammatory disease like systemic lupus erythematosis; psoriasis and psoriatic arthritis; T cell leukeamia; transplant rejection and graft-versus-host disease, which comprises administering an effective amount of a compound according to the present invention.

Said method comprising the systemic or topical administration of an effective amount of a compound according to the invention, to warm-blooded animals, including humans.

In yet a further aspect, the present invention provides the use of the compounds according to the invention in the manufacture of a medicament for treating any of the aforementioned T cell mediated diseases or indications.

The amount of a compound according to the present invention, also referred to here as the active ingredient, which is required to achieve a therapeutical effect will be, of course, vary with the particular compound, the route of administration, the age and condition of the recipient, and the particular disorder or disease being treated. A suitable daily dose would be from 0.01 mg/kg to 50 mg/kg body weight, in particular from 0.05 mg/kg to 10 mg/kg body weight. A method of treatment may also include administering the active ingredient on a regimen of between one and four intakes per day.

While it is possible for the active ingredient to be administered alone, it is preferable to present it as a pharmaceutical composition. Accordingly, the present invention further provides a pharmaceutical composition comprising a compound according to the present invention, together with a pharmaceutically acceptable carrier or diluent. The carrier or diluent must be "acceptable" in the sense of being compatible with the other ingredients of the composition and not deleterious to the recipients thereof.

The pharmaceutical compositions of this invention may be prepared by any methods well known in the art of pharmacy, for example, using methods such as those described in Gennaro et al. Remington's Pharmaceutical Sciences (18$^{th}$ ed., Mack Publishing Company, 1990, see especially Part 8: Pharmaceutical preparations and their Manufacture). A therapeutically effective amount of the particular compound, in base form or addition salt form, as the active ingredient is combined in intimate admixture with a pharmaceutically acceptable carrier, which may take a wide variety of forms depending on the form of preparation desired for administration. These pharmaceutical compositions are desirably in unitary dosage form suitable, preferably, for systemic administration such as oral percutaneous, or parenteral administration; or topical administration such as via inhalation, a nose spray, eye drops or via a cream, gel, shampoo or the like. For example, in preparing the compositions in oral dosage form, any of the usual pharmaceutical media may be employed, such as, for example, water, glycols, oils, alcohols and the like in the case of oral liquid preparations such as suspensions, syrups, elixirs and solutions: or solid carriers such as starches, sugars, kaolin, lubricants, binders, disintegrating agents and the like in the case of powders, pills, capsules and tablets. Because of their ease in administration, tablets and capsules represent the most advantageous oral dosage unit form, in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. In the compositions suitable for percutaneous administration, the carrier optionally comprises a penetration enhancing agent and/or a suitable wettable agent, optionally combined with suitable additives of any nature in minor proportions, which additives do not cause any significant deleterious effects on the skin. Said additives may facilitate the administration to the skin and/or may be helpful for preparing the desired compositions. These compositions may be administered in various ways, e.g., as a transdermal patch, as a spot-on or as an ointment. As appropriate compositions for topical application there may be cited all compositions usually employed for topically administering drugs e.g. creams, gellies, dressings, shampoos, tinctures, pastes, ointments, salves, powders and the like. Application of said compositions may be by aerosol, e.g. with a propellant such as nitrogen, carbon dioxide, a freon, or without a propellant such as a pump spray, drops, lotions, or a semisolid such as a thickened composition which can be applied by a swab. In particular, semisolid compositions such as salves, creams, gellies, ointments and the like will conveniently be used.

It is especially advantageous to formulate the aforementioned pharmaceutical compositions in dosage unit form for ease of administration and uniformity of dosage. Dosage unit form as used in the specification and claims herein refers to physically discrete units suitable as unitary dosages, each unit containing a predetermined quantity of active ingredient calculated to produce the desired therapeutic effect in association with the required pharmaceutical carrier. Examples of such dosage unit forms are tablets (including scored or coated tablets), capsules, pills, powder packets, wafers, injectable solutions or suspensions, teaspoonfuls, tablespoonfuls and the like, and segregated multiples thereof.

In order to enhance the solubility and/or the stability of the compounds of formula (I) in pharmaceutical compositions, it can be advantageous to employ α-, β- or γ-cyclodextrins or their derivatives. Also co-solvents such as alcohols may improve the solubility and/or the stability of the compounds of formula (I) in pharmaceutical compositions. In the preparation of aqueous compositions, addition salts of the subject compounds are obviously more suitable due to their increased water solubility.

Appropriate cyclodextrins are α-, β- or γ-cyclodextrins or ethers and mixed ethers thereof
wherein one or more of the hydroxy groups of the anhydroglucose units of the cyclodextrin are substituted with $C_{(1-6)}$alkyl, particularly methyl, ethyl or isopropyl, e.g. randomly methylated β-CD; hydroxy $C_{(1-6)}$alkyl, particularly hydroxyethyl, hydroxypropyl or hydroxybutyl; carboxy $C_{(1-6)}$alkyl, particularly carboxymethyl or carboxyethyl; $C_{(1-6)}$alkylcarbonyl, particularly acetyl; $C_{(1-6)}$alkyloxycarbonyl $C_{(1-6)}$alkyl or carboxy-$C_{(1-6)}$alkyloxy $C_{(1-6)}$alkyl, particularly carboxymethoxypropyl or carboxyethoxypropyl; $C_{(1-6)}$ alkylcarbonyloxy $C_{(1-6)}$alkyl, particularly 2-acetyloxypropyl. Especially noteworthy as complexants and/or solubilizers are β-CD, randomly methylated β-CD, 2,6-dimethyl-β-CD, 2-hydroxyethyl-β-CD, 2-hydroxyethyl-γ-CD, 2-hydroxypropyl-γ-CD and (2-carboxymethoxy)propyl-β-CD, and in particular 2-hydroxypropyl-β-CD (2-HP-β-CD).

The term mixed ether denotes cyclodextrin derivatives wherein at least two cyclodextrin hydroxy groups are etherified with different groups such as, for example, hydroxypropyl and hydroxyethyl.

The average molar substitution (M.S.) is used as a measure of the average number of moles of alkoxy units per mole of anhydroglucose. The M.S. value can be determined by various analytical techniques, preferably, as measured by mass spectrometry, the M.S. ranges from 0.125 to 10.

The average substitution degree (D.S.) refers to the average number of substituted hydroxyls per anhydroglucose unit. The D.S. value can be determined by various analytical techniques, preferably, as measured by mass spectrometry, the D.S. ranges from 0.125 to 3.

Experiment Part

Hereinafter, the term 'RT' means room temperature, 'THF' means tetrahydrofuran, 'EtOAc' means ethylacetate, 'DMF' means N,N-dimethylformamide, 'DIPE' means diisopropylether, 'Et$_2$O' means diethylether, 'NH$_4$OAc' means amoniumacetate and 'HOAc' means acetic acid.

A. PREPARATION OF THE INTERMEDIATE COMPOUNDS

EXAMPLE A.1 a.) A solution of N,N-diethylethanamine (0.544 mol) in ethanol (600 ml) was added dropwise to a stirred suspension of N-hydroxy-3-pyridinecarboximidoyl chloride (0.259 mol) and methyl 2-propenoate (1.295 mol) in ethanol (1500 ml) over a period of 1 hour. The reaction mixture was stirred for 1 hour at RT. The reaction mixture was evaporated. The residue was mixed with diethyl ether and filtered. The organic layer was separated, washed three times with water, separated again, dried (MgSO$_4$), filtered and left overnight. Partial crystallization occurred on overnight standing. The crystals were filtered and dried and the filtrate was evaporated, yielding 52.6 g (98%) of (±)-methyl 4,5-dihydro-3-(3-pyridinyl)-5-isoxazolecarboxylate (interm. 1).

b.) A solution of intermediate (1) (0.027 mol) in a mixture of NaOH 1 N (0.030 mol) and methanol (30 ml) was stirred at RT for 30 minutes. Then, 1 N HCl (30 ml) was added and this mixture was evaporated. The residue was crystallized from H$_2$O (25 ml). The crystals were filtered off, washed with cold water, and dried (fraction 1). Partial crystallization of the filtrate occurred. The crystals were filtered and dried yielding 3.8 g (72%) of (±)-4,5-dihydro-3-(3-pyridinyl)-5-isoxazolecarboxylic acid (interm. 2). c.) A mixture of intermediate (2) (0.031 mol) in thionyl chloride (100 ml) was refluxed until gas evolution stopped. The reaction mixture was evaporated (removal SOCl$_2$). Toluene was added to the residue and this mixture was evaporated again, yielding 7.6 g (100% crude residue) of (±)-4,5-dihydro-3-(3-pyridinyl)-5-isoxazolecarbonyl chloride monohydrochloride (interm. 3).

EXAMPLE A.2 a.) To a stirred and warm (40° C.) mixture of 1,2-dichloro-4-nitrobenzene (0,250 mol), 450 ml of NaOH solution 50%, 0,002 mol of N,N,N-triethylbenzenemethanaminium chloride and 225 ml of tetrahydrofuran is added dropwise a solution of 0,272 mol of 4-chlorobenzeneacetonitrile in 70 ml of tetrahydrofuran. Upon completion, stirring is continued for 5 hours at ±60° C. The reaction mixture is cooled and diluted with water. The whole is acidified with a hydrochloric acid solution and the product is extracted with Et$_2$O. The extract is washed with water, dried, filtered and evaporated, yielding 80 g of 2-chloro-α-(4-chlorophenyl)-4-nitrobenzeneacetonitrile as an oily solution. (interm. 4)

b.) A mixture of 80 g of intermediate (4), 80 g of iron-powder, 1000 ml of NH$_4$Cl solution (0.78 N) and 270 ml of methylbenzene is stirred and refluxed overnight. The reaction mixture is filtered over dicalite. The methylbenzene-phase is separated from the filtrate, dried, filtered and evaporated. The oily residue is crystallized from DIPE, yielding 36 grams of 4-amino-2-chloro-α-(4-chlorophenyl)benzeneacetonitrile. (interm. 5)

EXAMPLE A.3

A mixture of 0,277 mol of 1,4-benzenediamine, 0,017 mol of methyl 2-hydroxy benzoate and 10 grams of potassium carbonate is stirred for 1 hour at 190° C. Then there are added 0,049 mol of 1-chloro-4-(trifluoromethylsulfonyl) benzene and stirring at 190° C. is continued for 3 hours. The reaction mixture is cooled and stirred in 2000 ml of water. The precipitated product is filtered off, washed with water, dried and crystallized from a mixture of ethanol and water, yielding 2.3 grams of N-[4-(trifluoromethylsulfonyl) phenyl]-1,4-benzenediamine. (interm. 6)

EXAMPLE A.4 a.) A mixture of 0.020 mol of p-nitro-α-phenylhydratroponitrile and 28 ml of concentrated sulfuric acid solution (90%) is heated in a water-bath for 3.5 hours. The reaction mixture is poured onto crushed ice, neutralized with a sodium hydroxide solution and the product is extracted with chloroform. The organic layer is washed with water, dried and evaporated in vacuo and the residue is crystallized from either, yielding 2.4 grams of p-nitro-α-phenylhydratropamide. (interm. 7)

b.) A mixture of 0,048 mol of intermediate (7), 120 ml of absolute ethanol and 3 grams of palladium-on-charcoal catalyst 10% is hydrogenated at normal pressure and at a temperature between 30° and 60° C. After the calculated amount of hydrogen is taken up, hydrogenation is stopped. The catalyst is filtered off and the filtrate is evaporated in vacuo. The solid residue is washed with ether and crystallized from absolute ethanol, yielding 5.5 grams of p-amino-α-phenylhydratropamide. (interm.8)

c.) A mixture of intermediate (8) (0.0166 mol) in $CH_2Cl_2$ (105 ml) was cooled in an ice-water bath. 2-Butenoyl chloride (0.0208 mol) was added. N,N-diethylethanamine (0.0208 mol) was added dropwise. The reaction mixture was stirred for 3 hours at RT, then treated with water and extracted. The solvent of the extract was evaporated. The residue (2.1 g) was washed with ethanol, then purified by short open column chromatography over silica gel (eluent: $CH_2Cl_2/CH_3OH$ 96/4). The desired fractions were collected and the solvent was evaporated, yielding 1.3 g (27%) of (±)-α-methyl-4-[(1-oxo-2-propenyl)amino]-α-phenylbenzene-acetamide (interm. 9).

EXAMPLE A.5 a.) Hydroxylamine (0.0449 mol) was added to a mixture of 4-(2-phenyl-1,3-dioxin-2-yl)benzonitrile (0.022 mol) in ethanol (88 ml). Then, N,N-diethylethanamine (0.0449 mol) was added dropwise and the resulting reaction mixture was stirred and refluxed for 3.5 hours. The solvent was evaporated. The residue was washed with water and this mixture was extracted with EtOAc. The separated organic layer was dried ($Na_2SO_4$), filtered and the solvent was evaporated, yielding 6.38 g of N'-hydroxy-4-(2-phenyl-1,3-dioxolan-2-yl)benzenecarboimidamide (interm. 10)

b.) N,N-bis(1-methylethyl)ethanamine (0.04484 mol) was added to a solution of intermediate (10) (0.022 mol) in $CH_2Cl_2$ (69 ml) and THF (69 ml). This mixture was cooled with an ice-water bath. A suspension of (±)-4,5-dihydro-3-(3-pyridinyl)-5-isoxazolecarbonyl chloride monohydrochloride (0.0269 mol) in $CH_2Cl_2$ (80 ml) and THF (10 ml) was added portionwise and the resulting reaction mixture was stirred for one hour at RT. The crude reaction mixture was filtered and the solid was washed with diethyl ether to give 3.5 g of product. The filtrate was concentrated in vacuo and the residue was washed with water and extracted with $CH_2Cl_2$. The separated organic layer was dried ($Na_2SO_4$), filtered and the solvent was evaporated. The residue was washed with diethyl ether, then dried to give 4.13 g of product which was combined with the previous fraction, yielding ±7.63 g (74%) of (±)-[amino[4-(2-phenyl-1,3-dioxolan-2-yl)phenyl]methylene]amino 4,5-dihydro-3-(3-pyridinyl)-5-isoxazolecarboxylate (interm. 11).

EXAMPLE A.6 a.) A solution of hydrazine (0.023 mol) and N,N-dimethyl-4-pyridinamine (catalytic quantity) in $CH_2Cl_2$ (50 ml) was cooled in an ice-water bath. Half of a solution of 4-benzoylbenzoyl chloride (0.023 mol) in $CH_2Cl_2$ (60 ml) was added dropwise. The other half of this solution, and a solution of N,N-bis(1-methylethyl)ethanamine (0.023 mol) in $CH_2Cl_2$ (40 ml) were added simultaneously and dropwise. The resulting reaction mixture was stirred for 5 hours at RT. The crude reaction mixture was filtered and the filtrate was washed with water and extracted. The separated organic layer was dried ($Na_2SO_4$), filtered and the solvent was evaporated, yielding 1.9 g (34%) of 4-benzoylbenzoic acid hydrazide (interm. 12)

b.) A mixture of (±)-4,5-dihydro-3-(3-pyridinyl)-5-isoxazolecarbonyl chloride monohydrochloride (0.0095 mol; 2.74 g; 86%) and intermediate (12) (0.0079 mol) in $CH_2Cl_2$ (60 ml) and DMF (6 ml) was cooled with an ice-water bath, under $N_2$ atmosphere. N-ethyl-N-(1-methylethyl)-2-propanamine (0.0159 mol) was added dropwise and the resulting reaction mixture was stirred overnight at RT. This mixture was treated with water and filtered off. The solid residue was washed with a 10% aqueous $K_2CO_3$ solution and extracted with EtOAc/$CH_3OH$. The separated organic layer was dried ($Na_2SO_4$), filtered and the solvent was evaporated to give 0.62 g of residue. The filtrate was extracted. The extract was dried ($Na_2SO_4$), filtered and the solvent was evaporated to give a residue which was washed with a 3 N HCl solution. This mixture was extracted with EtOAc. The aqueous phase was alkalized with $K_2CO_3$, then extracted with EtOAc/$CH_3OH$. The organic layer was separated, dried ($Na_2SO_4$), filtered and the solvent was evaporated, to give 1 g of residue. Both product fractions were combined, treated with $Et_2O$, and filtered off, yielding 1.4 g (42%) of N2-(4-benzoylbenzoyl)-4,5-dihydro-3-(3-pyridinyl)-5-isoxazolecarboxylic acid hydrazide (interm. 13)

EXAMPLE A.7 a.) 1-Chloro-2,5-pyrrolidinedione (0.061 mol; 98%) was added portionwise to a mixture of 3-pyridinecarboxaldehyde, oxime (0.041 mol) and pyridine (0.32 ml) in $CHCl_3$ (300 ml) and this mixture was stirred for 3 hours at 40° C. The mixture was cooled to RT. 2-Propenenitrile (0.041 mol) was added. N,N-diethylethanamine (0.061 mol) was added dropwise while the temperature was kept <35° C. The resulting reaction mixture was stirred overnight at RT. The crude mixture was washed with water, then extracted. The organic layer was separated, dried ($Na_2SO_4$), filtered and the solvent was evaporated. The residue was purified by two open column chromatography over silica gel ((I) eluent: CH₂Cl₂/2-propanone 96/4 and CH₂Cl₂/CH₃OH 96/4; (II) hexane/EtOAc 4/1 and CH₂Cl₂/2-propanone 96/4). The pure fractions were collected and the solvent was evaporated, yielding 5.3 g (74%) of (±)-4,5-dihydro-3-(3-pyridinyl)-5-isoxazolecarbonitrile (interm. 14)

b.) Hydroxylamine (0.05 mol) was added to a mixture of intermediate (14) (0.025 mol) in ethanol (100 ml). N,N-diethylethanamine (0.050 mol) was added dropwise. The resulting reaction mixture was stirred and refluxed for 3 hours. The solvent was evaporated. The residue was washed with water and this mixture was extracted with EtOAc. The separated organic layer was dried (Na₂SO₄), filtered and the solvent was evaporated, yielding 4.7 g (91%) of (±)-4,5-dihydro-N'-hydroxy-3-(3-pyridinyl)-5-isoxazolecarboximidamide (interm. 15).

c.) A solution of intermediate (15) (0.024 mol) and N,N-bis(1-methylethyl)ethanamine (0.024 mol) in THF (40 ml) and CH₂Cl₂ (10 ml) was cooled on an ice-water bath. A solution of 4-benzoylbenzoyl chloride was stirred for 90 minutes at RT. The solvent was evaporated. The residue was washed with water and extracted with CH₂Cl₂/CH₃OH and EtOAc. The separated organic layer was dried (Na₂SO₄), filtered and the solvent was evaporated, yielding: 9.3 g (93%) of (±)-[[amino[4,5-dihydro-3-(3-pyridinyl)-5-isoxazolyl]methylene]amino] 4 benzoylbenzoate (interm. 16).

EXAMPLE A.8 a.) A mixture of 4-iodobenzeneamine (0.0405 mol) and N,N-bis(1-methylethyl)ethanamine (0.081 mol) in CH₂Cl₂ (250 ml) was stirred at 0° C. Intermediate (3) (0.0405 mol) was added portionwise and the resulting reaction mixture was stirred for 3 hours at RT. Water was added. The organic layer was separated, dried (MgSO₄), filtered and the solvent was evaporated under reduced pressure. The residue was stirred in EtOAc, filtered off, washed with EtOAc and dried, yielding 14.8 g (93%) of (±)-4,5-dihydro-N-(4-iodophenyl)-3-(3-pyridinyl)-5-isoxazolecarboxamide (interm. 17).

b.) Reaction under N₂ atmosphere. A mixture of intermediate (17) (0.003 mol), hexamethyl distannane, (0.006 mol), LiCl (0.009 mol) and Pd(trihenylphosphine)₄ (0.000009 mol) in 1,4-dioxane (50 ml) was stirred and refluxed for 2 hours, then filtered over Celite and the filtrate was evaporated under reduced pressure. The residue was purified by short column chromatography over silica gel (eluent: EtOAc). The desired fractions were collected and the solvent was evaporated under reduced pressure. The residue was stirred in DIPE, filtered off, washed with DIPE and dried, yielding 1.1 g of (±)-4,5-dihydro-N-[4-(trimethylstannane)phenyl]-3-(3-pyridinyl)-5-isoxazolecarboxamide carboxamide (interm. 18)

EXAMPLE A.9

A solution of 4-aminobenzoic acid (0.020 mol) and N-ethyl-N-(1-methylethyl)-2-propanamine, (0.020 mol) in CH₂Cl₂ (100 ml) was cooled to 0° C. (±)-4,5-dihydro-3-(3-pyridinyl)-5-isoxazolecarbonyl chloride monohydrochloride (0.020 mol) was added. The resulting brown suspension was stirred overnight. The precipitate was filtered off, washed with CH₂Cl₂, then dried. The filtrate was evaporated under reduced pressure. The residue was purified by short column chromatography over silica gel (eluent: CH₂Cl₂/CH₃OH 95/5). The pure fractions were collected and the solvent was evaporated under reduced pressure. The residue was stirred in methanol, filtered off, then dried, yielding 2.3 g of (±)-4-[[[4,5-dihydro-3-(3-pyridinyl)-5-isoxazolyl]carbonyl]amino]benzoic acid (interm. 19).

EXAMPLE A.10 a.) 1,1'-carbonylbis[1H-imidazole (0.022 mol) was added to benzeneacetic acid, α-hydroxy-4-nitro-α-phenyl (0.020 mol) in CH₂Cl₂ (150 ml). The mixture was stirred for one hour at room temperature. NH₃ (excess of gas) was allowed to bubble through the solution for 2 hours. The solvent was evaporated under reduced pressure. CH₂Cl₂ was added and the mixture was washed with water and brine. The organic layer was separated, dried (Na₂SO₄), filtered and the solvent was evaporated under reduced pressure. The residue was purified by short open column chromatography over silica gel (eluent: CH₂Cl₂/CH₃OH 98/2). The desired fractions were collected and the solvent was evaporated. Yielding: 2.1 g of of (±)-α-hydroxy-4-nitro-α-phenylbenzeneacetamide (interm. 20) (38%, 90% pure by HPLC, used in next reaction step, without further purification).

b.) Intermediate (20) (0.0069 mol) and thiophene/2-propanol (0.155 ml) were added to Pd/C (1.96 g) in methanol (50 ml) under N₂ atmosphere. The mixture was hydrogenated at 50 psi for 2 hours. After filtration through dicalite, the solvent was evaporated under reduced pressure. Yielding: 1.53 g of (±)-4-amino-α-hydroxy-α-phenylbenzeneacetamide (interm. 21).

EXAMPLE A.11 a.) Reaction under N₂ atmosphere. A solution of phenyl-(4-nitrophenyl)-acetonitrille (0.0209 mol) in DMF (6 ml) was added dropwise to a mixture of NaH, 60%, (0.023 mol) in E (6 ml). The mixture was stirred for 30 min at room temperature. 1-chloro-2-methoxyethane (0.315 mol) was added dropwise. Then, 18-crown-6 (catalytic quantity) was added and the resulting reaction mixture was stirred overnight at 60° C. More 1-chloro-2-methoxyethane (5.86 ml) was added. NaI (catalytic amount) was added and the reaction mixture was stirred for 3 days at 60° C. The crude reaction mixture was washed with water and extracted with EtOAc. The separated organic layer was dried (Na₂SO₄), filtered, and the solvent was evaporated. The residue was purified by short open column chromatography over silica gel (eluent: hexane/EtOAc 96/4 90/10 and 80/20). The purest fractions were collected and the solvent was evaporated. Yielding: 3.11 g of (±)-α-(2-methoxyethyl)-4-nitro-α-phenylbenzeneacetonitrile (interm. 22)

b.) A solution of intermediate (22) (0.0105 mol) and thiophene, 0.01% in 2-propanol, (0.03 ml) in methanol (150 ml) was hydrogenated in a Parr apparatus at room temperature with Pd/C (0.9 g) as a catalyst. After uptake of H₂ (3 equiv), the catalyst was filtered off and the filtrate was evaporated. Yielding: 2.74 g (±)-4-amino-α-(2-methoxyethyl)-α-phenylbenzeneacetonitrile (interm. 23).

B. PREPARATION OF THE FINAL COMPOUNDS

EXAMPLE B.1 a.) A mixture of intermediate (1) (0.040 mol) and (4-aminophenyl)phenylmethanone (0.041 mol) in CH₂Cl₂ (250 ml) was stirred at RT. Triethylamine (0.089 mol) was added dropwise and the resulting reaction mixture was stirred for 1 hour at RT. Water was added and the mixture was stirred for 20 minutes. The organic layer was separated, dried (MgSO₄), filtered and the solvent was evaporated under reduced pressure. The residue was stirred in 50–80 ml of CH$_2$Cl$_2$, then purified by short column chromatography over silica gel (eluent: CH$_2$Cl$_2$/CH$_3$OH 98/2). The pure fractions were collected and the solvent was evaporated under reduced pressure. The residue (oil) was boiled in EtOAc, filtered off, washed with EtOAc, then dried, yielding 8.6 g (58%) (±)-N-(4-benzoylphenyl)-4,5-dihydro-3-(3-pyridinyl)-5-isoxazolecarboxamide. (compound 1)

b.) Compound (1) (0.046 mol) was purified and separated into its optical enantiomers by column chromatography over a Diacel Chiralcel OJ column (eluent: pure methanol). Two pure fraction groups were collected and their solvent was evaporated under reduced pressure, yielding (R)-enantiomer and (S)-enantiomer. The (R)-enantiomer was stirred in DIPE. The precipitate was filtered off, washed with DIPE, and dried, yielding 7.3 g (R)-N-(4-benzoylphenyl)-4,5-dihydro-3-(3-pyridinyl)-5-isoxazolecarboxamide (compound 2). The (S)-enantiomer was stirred in DIPE. The precipitate was filtered off, washed with DIPE, and dried, yielding: 5.3 g of (S)-N-(4-benzoylphenyl)-4,5-dihydro-3-(3-pyridinyl)-5-isoxazolecarboxamide (compound 3).

c.) Compound (3) (0.0001 mol) and bicyclo[2.2.1]heptane-1-methanesulfonic acid (0.0001 mol) were dissolved in 2-propanone (2 ml) and 4-methyl-2-pentanone (2 ml), by heating. The mixture was slowly cooled to room temperature. The precipitate was filtered off and dried (vacuum, 50° C.). Yielding: 0.048 g (S)-N-(4-benzoylphenyl)-4,5-dihydro-3-(3-pyridinyl)-5-isoxazolecarboxamide (1:1) monohydrate (compound 491).

EXAMPLE B.2

To a cooled stirred suspension of (±)-4,5-dihydro-3-(3-pyridinyl)-5-isoxazole carbonylchloride monohydrochloride (0.016 mol) in dry THF (100 ml), triethylamine (0.040 mol) was added. The reaction mixture was cooled to 0° C. 4-[(Hydroxyimino)phenylmethyl]benzeneamine (0.018 mol) was added in one portion. Stirring was continued for 2.5 hours. Water was added to the reaction mixture and this mixture was extracted with CH$_2$Cl$_2$. The organic layer was separated, dried (MgSO$_4$), filtered and the solvent was evaporated. The residue was stirred in CH$_3$OH/CH$_2$Cl$_2$ 5/95. The precipitate was filtered off, washed with CH$_3$OH/CH$_2$Cl$_2$ 5/95 and dried. The product (1.6 g) was stirred in boiling ethyl acetate (25 ml) and crystallized from ethyl acetate (150 ml). The volume was reduced to 75 ml. The precipitate was filtered off, washed with ethyl acetate and DIPE, then dried, yielding 0.8 g of (±)-(E)-4,5-dihydro-N-[4-[(hydroxyimino)phenylmethyl]phenyl]-3-(3-pyridinyl)-5-isoxazolecarboxamide. (compound 301)

EXAMPLE B.3

Intermediate (1) (0.012 mol) was added to a solution of 4-(phenylmethyl)benzenamine (0.012 mol), CH$_2$Cl$_2$ (dry) (0.024 mol) and N,N-dimethyl-4-pyridinamine (catalytic quantity) in CH$_2$Cl$_2$ (100 ml), stirred at 0° C. The reaction mixture was stirred overnight at RT. Water was added. The organic layer was separated, dried (MgSO$_4$), filtered and the solvent was evaporated under reduced pressure. The residue was purified by flash column chromatography over silica gel (eluent: CH$_2$Cl$_2$/CH$_3$OH 98/2). The desired fractions were collected and the solvent was evaporated under reduced pressure. The residue was stirred in EtOAc, filtered off, washed with EtOAc, then dried, yielding 2.9 g of (±)-4,5-dihydro-N-[4-(phenylmethyl)phenyl]-3-(3-pyridinyl)-5-isoxazolecarboxamide. (compound 44)

EXAMPLE B.4 a.) Intermediate (1) (0.010 mol) was added at 0° C. to a solution of α-(4-aminophenyl)benzeneacetonitrile (0.01 mol), N,N-bis(1-methylethyl)ethanamine (0.02 mol) and N,N-dimethyl-4-pyridinamine (cat. quant.) in CH$_2$Cl$_2$ (100 ml). The mixture was allowed to warm to RT and then stirred at RT for 3 hours. H$_2$O was added. The organic layer was separated, dried (MgSO$_4$), filtered and the solvent was evaporated under reduced pressure. The residue was solidified in EtOAc. The precipitate was filtered off, washed with EtOAc and dried in vacuo at 50° C. for 4 hours, yielding 2.2 g (58%) of (±)-N-[4-(cyanophenylmethyl)phenyl]-4,5-dihydro-3-(3-pyridinyl)-5-isoxazolecarboxamide. (compound 55)

b.) A mixture of compound (55) (0.003 mol) and triethylamine (0.003 mol) in pyridine (100 ml) was stirred at 80° C. H$_2$S was allowed to bubble through the solution during 48 hours. Then, the reaction mixture was stirred for one day at 80° C. The solvent was evaporated under reduced pressure. The residue was dissolved in CH$_2$Cl$_2$. The organic solution was washed with water, dried (MgSO$_4$), filtered and the solvent was evaporated under reduced pressure. The residue was purified by short column chromatography over silica gel (eluent: CH$_2$Cl$_2$/CH$_3$OH 95/5). The desired fractions were collected and the solvent was evaporated under reduced pressure. The residue was stirred in DIPE, filtered off, washed with DIPE, then dried, yielding 0.4 g (39%) of (±)-N-[4-(2-amino-1-phenyl-2-thioxoethyl)phenyl]-4,5-dihydro-3-(3-pyridinyl)-5-isoxazolecarboxamide (compound 313).

EXAMPLE B.5

Intermediate (1) (0.044 mol) was added portionwise to a solution of (4-aminophenyl) (4-hydroxyphenyl)methanone (0.044 mol), N,N-bis(1-methylethyl)ethanamine (0.088 mol) and N,N-dimethyl-4-pyridinamine (catalytic quantity) in CH$_2$Cl$_2$ (500 ml), stirred at 0° C. The reaction mixture was stirred overnight at RT. Water was added. The organic layer was separated, dried (MgSO$_4$), filtered and the solvent was evaporated under reduced pressure. The residue was purified by short column chromatography over silica gel (eluent: CH$_2$Cl$_2$/CH$_3$OH 98/2). The pure fractions were collected and the solvent was evaporated under reduced pressure. The residue (oil) was solidified in DIPE, filtered off, washed with DIPE, then dried, yielding 10.1 g (60%) of (±)-4,5-dihydro-N-[4-(4-methoxybenzoyl)phenyl]-3-(3-pyridinyl)-5-isoxazolecarboxamide. (compound 15)

EXAMPLE B.6

3-Pyridinecarboxaldehyde, oxime (0.013 mol) was added to a suspension of 1-chloro-2,5 pyrrolidinedione (0.0148 mol) in CHCl$_3$ (80 ml) and pyridine (0.16 ml), stirred at RT. The mixture was stirred for 3 hours at 40° C., then cooled to 0° C. and 4-benzoyl-N-(2-propenyl)benzamide (0.011 mol) was added. Then, triethylamine (2.25 ml) was added dropwise and the resulting reaction mixture was stirred overnight at RT. The reaction mixture was washed with water, dried (Na$_2$SO$_4$), filtered and the solvent was evaporated. The residue was crystallized from CH$_3$CN. The precipitate was filtered off and dried, yielding 2.0 g (37%) of (±)-4-benzoyl-N-[[4,5-dihydro-3-(3-pyridinyl)-5-isoxazolyl]methyl]benzamide. (compound 343).

EXAMPLE B.7

3-Pyridinecarboxaldehyde, oxime (0.0044 mol) was added to a suspension of 1-chloro-2,5-pyrrolidinedione (0.0048 mol) in CHCl$_3$ (27 ml) and pyridine (0.05 ml), stirred at RT. The mixture was stirred for 3 hours at 40° C., then cooled to 0° C. At 0° C., intermediate (9) (0.0044 mol)

was added. Triethylamine (0.0052 mol) was added dropwise and the resulting reaction mixture was stirred for 18 hours at RT. The reaction mixture was washed with water, dried ($Na_2SO_4$), filtered and the solvent was evaporated. The residue was purified by short open column chromatography over silica gel (eluent: $CH_2Cl_2/CH_3OH$ 97/3). The pure fractions were collected and the solvent was evaporated. The residue (0.7 g) was washed with EtOAc, then dried, yielding 0.2 g (11%) of (±)-N-[4-[1-(aminocarbonyl)-1-phenylethyl]phenyl]-4,5-dihydro-3-(3-pyridinyl)-5-isoxazolecarboxamide (compound 323).

EXAMPLE B.8

A mixture of intermediate (11) (0.017 mol) and 4-methylbenzenesulfonic acid (0.017 mol) in DMSO (53 ml) was stirred for one hour at 140° C. The crude reaction mixture was cooled and poured out onto crushed ice. The precipitate was filtered off and washed with water, then dissolved in $CH_2Cl_2$. The organic solution was washed with brine and extracted. The separated organic layer was dried ($Na_2SO_4$), filtered and the solvent was evaporated. The residue was purified by open column chromatography over silica gel (eluent: $CH_2Cl_2/CH_3OH$ 98/2 and 96/4). The desired fractions were collected and the solvent was evaporated. The residue was crystallized from DIPE and recrystallized from DIPE/$CH_2Cl_2$, filtered off and dried, yielding 3.7 g (56%) (±)-[4-[5-(4,5-dihydro-3-(3-pyridinyl)-5-isoxazolyl]-1,2,4-oxadiazol-3-yl]phenyl]phenylmethanone (compound 446).

EXAMPLE B.9

Intermediate (13) (0.003 mol) was added portionwise to $POCl_3$ (27 ml), cooled with an ice-water bath. The reaction mixture was allowed to warm to RT. Then, it was stirred for 24 hours at 80° C. The solvent was evaporated. The residue was washed with a 10% aqueous $Na_2CO_3$ solution and extracted with EtOAc. The separated organic layer was dried ($Na_2SO_4$), filtered and the solvent was evaporated. The residue was purified by open column chromatography over silica gel (eluent: $CH_2Cl_2$/2-propanone 90/10, $CH_2Cl_2$/$CH_3OH$ 96/4), then repurified by HPLC (eluent: $CH_2Cl_2$/$CH_3OH$ 97.5/2.5). The desired fractions were collected and the solvent was evaporated. The residue was washed with methanol, filtered off and dried, yielding 0.3 g (25%) of (±)-[4-[5-[4,5-dihydro-3-(3-pyridinyl)-5-isoxazolyl]-1,3,4-oxadiazol-2-yl]phenyl]phenylmethanone (compound 447).

EXAMPLE B.10

A reaction solution of intermediate (16) (0.022 mol) and 4-methylbenzenesulfonic acid (0.022 mol) in DMSO (70 ml) was stirred for one hour at 140° C. The reaction mixture was cooled and poured out into crushed ice. The precipitate was filtered off, washed with water, then dissolved in $CH_2Cl_2$. The separated organic layer was dried ($Na_2SO_4$), filtered and the solvent was evaporated. The residue was purified first by open column chromatography over silica gel (eluent: $CH_2Cl_2/CH_3OH$ 100/0 and 96/4), then by HPLC (eluent: $CH_2Cl_2/CH_3OH$ 99/1). The pure fractions were collected and the solvent was evaporated, yielding 2.8 g (31%) of (±)-[4-[3-[4,5-dihydro-3-(3-pyridinyl)-5-isoxazolyl]-1,2,4-oxadiazol-5-yl]phenyl]methanone (compound 445).

EXAMPLE B.11

To a solution of $Pd_2(dba)_3$ in 1,2 dichloroethane, under nitrogen atmosphere, tri-2-furylphosphine is added in one portion at RT. Then, a solution of the acid chloride in 1,2 dichloroethane is added dropwise followed by intermediate Sn-compound (intermediate 18). The reaction mixture is heated up till 80° C. and stirred overnight. The reaction mixture was cooled till RT, filtered through Celite and the filtrate was concentrated under reduced pressure. The residue was purified by reversed-phase HPLC over Kromasil C18 (22 g, 100 Å, 5 μm) (column: one inch I.D.; eluent: ((0.5% $NH_4OAc$ in $H_2O$)/$CH_3CN$ 90/10)/$CH_3OH$/$CH_3CN$. The desired fractions were collected and the solvent was evaporated, yielding 0.1 g of (±)-4,5-dihydro-3-(3-pyridinyl)-N-[4-[3-(trifluoromethyl)benzoyl]phenyl]-5-isoxazolecarboxamide (compound 8).

EXAMPLE B.12

1,1'-carbonylbis-1H-imidazole (0.010 mol) was added to a stirring mixture of intermediate (19) (0.01 mol) in $CH_2Cl_2$ (50 ml). THF was added until a clear solution was obtained. The mixture was stirred and refluxed until the evolution of $CO_2$ had stopped. Benzenemethanamine (0.010 mol) was added dropwise. The mixture was stirred at RT overnight. The precipitate was filtered off, washed with $H_2O$ and dried in vacuo at 60° C. for 16 hours, yielding 1.7 g of (±)-4,5-dihydro-N-[4-[[(phenylmethyl)amino]carbonyl]phenyl]-3-(3-pyridinyl)-5-isoxazolecarboxamide. (compound 257)

EXAMPLE B.13 a.) $NaBH_4$ (0.001 mol) was added to a suspension of compound (1) (0.003 mol) in methanol (50 ml). The reaction mixture was stirred for 2 hours. $NaBH_4$ (0.026 g) was added and the reaction mixture was stirred overnight at RT. The precipitate was filtered off, washed with $CH_3OH$ and DIPE, then dried, yielding 0.7 g (70%) of (±)-4,5-dihydro-N-[4-(hydroxyphenylmethyl)phenyl]-3-(3-pyridinyl)-5-isoxazolecarboxamide (compound 50).

b.) HCl (excess of gas) was allowed to bubble through a solution of compound (50) (0.008 mol) in $CH_2Cl_2$ (100 ml) during 2 minutes. $SOCl_2$ (0.016 mol) was added and the resulting reaction mixture was stirred and refluxed for 1 hour (HCl gas evolution). The reaction mixture was concentrated under reduced pressure. Toluene was added and azeotroped on the rotary evaporator (2×). The crude solid residue was taken up into methanol (50 ml) and this mixture was heated to 80° C. (HCl gas evolution) and stirred for 30 minutes. The solvent was evaporated under reduced pressure. The residue was taken up into $CH_2Cl_2$ and washed with a 10% aqueous $NaHCO_3$ solution. The organic layer was dried ($MgSO_4$), filtered and the solvent was evaporated under reduced pressure. The residue was stirred up in diethyl ether. The precipitate was filtered off and the filtrate was evaporated under reduced pressure and purified by short column chromatography over silica gel (eluent: $CH_2Cl_2/CH_3OH$ 99/1). The desired fractions were collected and the solvent was evaporated under reduced pressure. The oily residue was stirred up in diethyl ether. The precipitate was filtered off, washed with diethyl ether and dried, yielding 0.1 g (22%) of (±)-4,5-dihydro-N-[(4-(methoxyphenylmethyl) phenyl]-3-(3-pyridinyl)-5-isoxazolecarboxamide (compound 58).

EXAMPLE B.14

A mixture of Mg (0.035 mol) in THF (20 ml) was stirred. $CH_3I$ (1 drop) was added. The mixture was heated. A solution of 2-bromopropane (0.035 mol) in THF (20 ml) was added dropwise. After complete addition, the mixture was stirred and refluxed until all Mg was consumed and then cooled to 0° C. A solution of compound (1) (0.010 mol) in THF (20 ml) was added dropwise. After complete addition, the mixture was stirred at RT, neutralized with a saturated NH₄Cl solution and extracted with CH₂Cl₂. The organic layer was separated, dried (MgSO₄), filtered and the solvent was evaporated under reduced pressure. The residue was purified by short column chromatography over silica gel (eluent: CH₂Cl₂/CH₃OH 98/2). The desired fractions were collected and their solvents were evaporated. The residue was stirred in DIPE, filtered off, washed with DIPE/EtOAc and dried in vacuo at 50° C. for 16 hours, yielding 0.3 g of N-[4-[hydroxy-(1-methylethyl)phenylmethyl]phenyl]-4,5-dihydro-3-(3-pyridinyl)-5-isoxazolecarboxamide. (compound 66)

EXAMPLE B.15

Phenyllithium (0.0334 mol; 16.7 ml, 2.0 M in THF/Et₂O) was added dropwise to a 0° C. solution of compound (1) (0.011 mol) in THF (100 ml). The reaction mixture was stirred for 2 hours at RT, then cooled to 0° C. A saturated aqueous NH₄Cl solution was added dropwise and this mixture was extracted with CH₂Cl₂. The separated organic layer was dried (MgSO₄), filtered and the solvent evaporated under reduced pressure. The residue was purified by short column chromatography over silica gel (eluent: CH₂Cl₂/CH₃OH 98/2). The pure fractions were collected and the solvent was evaporated under reduced pressure. This fraction (crude oil) was stirred in CH₃CN, filtered off, washed with CH₃CN and DIPE, then dried, yielding 0.3 g (5%) of N-[4-[hydroxy(diphenyl)methyl]phenyl]-4,5-dihydro-3-(3-pyridinyl)-5-isoxazole carboxamide (compound 54).

EXAMPLE B.16 a.) Compound (58) (0.026 mol) was suspended in CH₂Cl₂ (100 ml). HCl (excess) was allowed to bubble through the suspension for 30 minutes. Thionyl chloride (0.042 mol) was added to the resultant gel and the reaction mixture was stirred and refluxed for 4 hours (HCl gas evolution). The reaction mixture was cooled to RT. The resulting precipitate was filtered off, washed with DIPE, and dried, yielding 10.5 g (94%) of (±)-N-[4-(chlorophenylmethyl)phenyl]-4,5-dihydro-3-(3-pyrid|inyl)-5-isoxazolecarboxamide monohydrochloride (compound 492).

b.) A mixture of (±)-N-[4-(chlorophenylmethyl)phenyl]-4,5-dihydro-3-(3-pyridinyl)-5-isoxazolecarboxamide monohydrochloride (0.00035 mol), ethanamine (0.2 g) and triethylamine (0.5 ml) in DMF (2 ml) was stirred overnight at RT. The desired compound was isolated and purified by HPLC over a Prochrom D.A.C.-column with Hyperprep 'BDS' HS C18 (100 g, 8 μm, 100 Å; eluent gradient: ((0.5% NH₄OAc in H₂O)/CH₃CN 90/10)/CH₃OH/CH₃CN. The desired fractions were collected and the solvent was evaporated, yielding 0.1 g of (±)-N-[4-[(ethylamino)phenylmethyl]phenyl]-4,5-dihydro-3-(3-pyridinyl)-5-isoxazolecarboxamide. (compound 89)

EXAMPLE B.17 a.) Bis(1,1-dimethylethyl) imidodicarbonoate (0.058 mol) was added portionwise to a mixture of NaH 40% (0.113 mol) in THF (500 ml), stirred at RT (foaming resulted). The mixture was stirred for one hour at RT. Compound (58) (0.053 mol) was added and the resulting reaction mixture was stirred vigorously for 4 hours at RT (H₂ gas evolution). A saturated aqueous NH₄Cl solution was added and this mixture was extracted with CH₂Cl₂. The separated organic layer was dried (MgSO₄), filtered and the solvent evaporated under reduced pressure. The residue (crude oil) was purified by short column chromatography over silica gel (eluent: CH₂Cl₂/CH₃OH 97/3). The pure fractions were collected and the solvent was evaporated under reduced pressure, yielding 20.9 g (69%) and 8.0 (26%) g of (±)-1,1-dimethyl [(1,1-dimethylethoxy)carbonyl][[4-[[[4,5-dihydro-3-(3-pyridinyl)-5-isoxazolyl]carbonyl]amino]phenyl]phenylmethyl]carbamate (compound 125).

b.) Trifluoroacetic acid (50 ml) was added dropwise to a solution of compound (125) (0.037 mol) in CH₂Cl₂ (500 ml), stirred at RT. The reaction mixture was stirred overnight at RT. The solvent was evaporated under reduced pressure. Toluene was added and azeotroped on the rotary evaporator (2×). The residue (crude oil) was dissolved in CH₂Cl₂. The organic solution was washed with 1 N NaOH (2×), dried (MgSO₄), filtered and the solvent was evaporated under reduced pressure. The residue was crystallized from EtOAc, filtered off, washed with EtOAc, then dried, yielding 7.4 g (54%) of (±)-N-[4-(aminophenylmethyl)phenyl]-4,5-dihydro-3-(3-pyridinyl)-5-isoxazolecarboxamide. (compound 126)

c.) (5S)-N-[4-(aminophenylmethyl)phenyl]-4,5-dihydro-3-(3-pyridinyl)-5-isoxazole carboxamide (0.0067 mol) was separated by chiral high-performance liquid chromatography over Chiralpak AD (250 g, 35 bar, flow: 30 ml/minute, wavelength: 220 nm, 0.300 g per injection dissolved in 40 ml of eluent; eluent: CH₃CN/C₂H₅OH 80/20). Two desired fraction groups were collected and their solvent was evaporated. The (A)-residue was stirred in EtOAc, filtered off, washed with some DIPE and dried, yielding 0.9 g of [5S-(A)]-N-[4-(aminophenylmethyl)phenyl]-4,5-dihydro-3-(3-pyridinyl)-5-isoxazolecarboxamide (compound 205).

The (B)-residue was stirred in EtOAc, filtered off, washed with DIPE and dried, yielding 1.2 g of [5S-(B)]-N-[4-(aminophenylmethyl)phenyl]-4,5-dihydro-3-(3-pyridinyl)-5-isoxazolecarboxamide (compound 206).

EXAMPLE B.18 a.) A solution of chloroacetylchloride (0.0089 mol) in CH₂Cl₂ (20 ml, dried over MgSO₄) was added to a cooled solution of (±)-N-[4-(aminophenylmethyl)phenyl]-4,5-dihydro-3-(3-pyridinyl)-5-isoxazolecarboxamide (0.0081 mol) and N-ethyl-N-(1-methylethyl)-2-propanamine (0.0093 mol) in CH₂Cl₂ (100 ml). The reaction mixture was stirred for one hour at 0° C. Water was added. The organic layer was separated, dried (MgSO₄), filtered and the solvent was evaporated under reduced pressure. The residue (crude oil) was purified by short column chromatography over silica gel (eluent: CH₂Cl₂/CH₃OH 98/2). The pure fractions were collected and the solvent was evaporated under reduced pressure. The residue was stirred in EtOAc. The precipitate was filtered off, washed with EtOAc, and dried, yielding 2.47 g (68%) of (±)-N-[4-[[(chloroacetyl)amino]phenylmethyl]phenyl]-4,5-dihydro-3-(3-pyridinyl)-5-isoxazolecarboxamide. (compound 127)

A mixture of compound (127) (±)-N-[4-[[(chloroacetyl)amino]phenylmethyl]phenyl]-4,5-dihydro-3-(3-pyridinyl)-5-isoxazolecarboxamide (0.00022 mol), 1-methylpiperazine (0.100 g, ±0.00022 mol) and triethylamine (0.5 ml) in DMF (2 ml) was stirred over the weekend at 50° C. Then, the desired compound was isolated and purified by high-performance liquid chromatography over a Prochrom D.A.C.-column with Hyperprep 'BDS' HS C18 (100 g, 8 μm, 100 Å; eluent gradient: ((0.5% NH₄OAc in H₂O)/CH₃CN 90/10)/CH₃OH/CH₃CN (0 minutes) 75/25/0, (10.31 minutes) 0/50/50, (16.32 minutes) 0/0/100, (16.33 minutes-end) 75/25/0). The desired fractions were collected and the solvent was evaporated, yielding 0.080 g of (±)-4,5-dihydro-N-[4-[[[(4-methyl-1-piperazinyl)acetyl]amino]phenylmethyl]phenyl]-3-(3-pyridinyl)-5-isoxazolecarboxamide. (compound 140)

EXAMPLE B.19 a.) Intermediate (3) (0.007 mol) was added to a solution of methyl [(4-aminophenyl) phenyl]acetate (0.007 mol), N,N-bis(1-methylethyl)ethanamine (0.014 mol) and N,N-dimethyl-4-pyridinamine (catalytic quantity) in $CH_2Cl_2$ (100 ml), stirred at 0° C. The reaction mixture was stirred overnight at RT. Water was added. The organic layer was separated, dried ($MgSO_4$), filtered and the solvent was evaporated under reduced pressure. The residue was purified by flash column chromatography over silica gel (eluent: $CH_2Cl_2/CH_3OH$ 98/2). The pure fractions were collected and the solvent was evaporated under reduced pressure. The residue was crystallized from EtOAc. The precipitate was filtered off, washed with EtOAc, and dried, yielding 1.0 g (35%) of (±)-methyl 4-[[[4,5-dihydro-3-(3-pyridinyl)-5-isoxazolyl]carbonyl]amino]-α-phenylbenzeneacetate (compound 56).

b.) A mixture of compound (56) (0.001 mol) in methanol (100 ml) was cooled to 0° C. NaOH 1N (0.0288 mol) was added and the reaction mixture was stirred overnight at RT. The reaction mixture was re-cooled to 0° C. 1 N HCl (30 ml) was added and this mixture was extracted with $CH_2Cl_2$. The separated organic layer was dried ($MgSO_4$), filtered and the solvent evaporated under reduced pressure. The residue was crystallized from ethanol. The precipitate was filtered off, washed with ethanol, and dried, yielding 0.2 g (5.2%) (±)-4-[[[4,5-dihydro-3-(3-pyridinyl)-5-isoxazolyl]carbonyl]amino]-α-phenylbenzeneacetic acid (compound 406).

c.) HCl (gaseous) (excess) was bubbled through a suspension of (±)-4-[[[4,5-dihydro-3-(3-pyridinyl)-5-isoxazolyl]carbonyl]amino]-a-phenylbenzeneacetic acid (0.005 mol) in $CH_2Cl_2$ (100 ml) for 10 minutes. The solvent was removed under reduced pressure. The white solid was co-evaporated twice with toluene. Thionyl chloride (50 ml) was added. The reaction mixture was heated and refluxed for 1 hour. The solvent was evaporated. The reaction mixture was co-evaporated three times with toluene, yielding N-[4-[(chlorocarbonyl)phenylmethyl]phenyl]-4,5-dihydro-3-(3-pyridinyl)-5-isoxazolecarboxamide (compound 493).

d.) A mixture of N-[4-[(chlorocarbonyl)phenylmethyl]phenyl]-4,5-dihydro-3-(3-pyridinyl)-5-isoxazolecarboxamide (0.00047 mol) and 2-propanamine (0.200 g) in pyridine (1 ml) was stirred overnight at 60° C. Then, the desired compound was isolated and purified by high-performance liquid chromatography over Kromasil C18 (22 g, 100 Å, 5 μm) (column: one inch I.D.; eluent: ((0.5% $NH_4OAc$ in $H_2O)/CH_3CN$ 90/10)/$CH_3OH/CH_3CN$. The desired fractions were collected and the solvent was evaporated, yielding 0.1 g of (±)-4,5-dihydro-N-[4-[2-(dimethylamino)-2-oxo-1-phenylethyl]phenyl]-3-(3-pyridinyl)-5-isoxazolecarboxamide. (compound 316).

EXAMPLE B.20 a.) $CH_3MgCl$, 22% (w/w)/THF (0.003 mol) was added dropwise to a cooled (0° C.) solution of (±)-N-(4-benzoylphenyl)-4,5-dihydro-3-(3-pyridinyl)-5-isoxazolecarboxamide (0.003 mol) in THF (50 ml). The reaction mixture was stirred for 30 minutes at 0° C. More $CH_3MgCl$, 22% w/w/THF (0.003 mol) was added and the mixture was stirred for 30 minutes at 0° C. Extra $CH_3MgCl$, 22% (w/w)/THF (0.003 mol) was added and the reaction mixture was stirred for 30 minutes at 0° C. The mixture was allowed to warm to RT for 30 minutes, then cooled again to 0° C. Water was added. This mixture was extracted with $CH_2Cl_2$. The separated organic layer was dried ($MgSO_4$), filtered and the solvent evaporated under reduced pressure. The crude oil was crystallized from EtOAc. The precipitate was filtered off, washed with EtOAc, and dried, yielding 0.5 g (50%) of (±)-4,5-dihydro-N-[4-(1-hydroxy-1-phenylethyl)phenyl]-3-(3-pyridinyl)-5-isoxazolecarboxamide (compound 51).

b.) Methanesulfonyl chloride (0.010 mol) was added to a solution of compound (51) (0.005 mol) and triethylamine (0.013 mol) in $CH_2Cl_2$ (100 ml, dried over $MgSO_4$), stirred at 0° C. The resulting reaction mixture was stirred for 1 hour at 10° C. Water was added. The organic layer was separated, dried ($MgSO_4$), filtered and the solvent was evaporated under reduced pressure. The residue was purified by short column chromatography over silica gel (eluent: $CH_2Cl_2/CH_3OH$ 97/3). The pure fractions were collected and the solvent was evaporated under reduced pressure. The residue was crystallized from EtOAc. The precipitate was filtered off, washed with EtOAc, then dried, yielding 0.5 g (27%) of (±)-4,5-dihydro-N-[4-(1-phenylethenyl)phenyl]-3-(3-pyridinyl)-5-isoxazolecarboxamide (compound 378).

EXAMPLE B.21

Sodium acetylide (0.024 mol; 7.2 g of slurry (18 wt % in xylene/light mineral oil)) was added portionwise to a solution of compound (3) (0.008 mol) in THF (50 ml), stirred at 0° C. The reaction mixture was stirred for 30 minutes at 0° C., then overnight at RT. More sodium acetylide (5 ml) was added at 0° C. and the reaction mixture was allowed to warm to RT, then stirred for 2 hours at 40° C. A saturated aqueous $NH_4Cl$ solution (200 ml) was added and this mixture was extracted with $CH_2Cl_2$ (2×300 ml). The separated organic layer was dried ($MgSO_4$) and the solvent evaporated. The residue was purified by column chromatography over silica gel (eluent: $CH_2Cl_2/CH_3OH$ 99/1). The desired fractions were collected and the solvent was evaporated. EtOAc was added and azeotroped on the rotary evaporator. The residue was dried, yielding 1.3 g (40%) of [B(R)]+[B(S)]-4,5-dihydro-N-[4-(1-hydroxy-1-phenyl-2-propynyl)phenyl]-3-(3-pyridinyl)-5-isoxazolecarboxamide. (compound 69)

EXAMPLE B.22

A mixture of compound (3) (0.010 mol), 1,2-ethanediol (10 ml) and 4-methylbenzenesulfonic acid (catalytic quantity) in toluene (100 ml) was stirred and refluxed for 24 hours. The solvent was evaporated under reduced pressure. The crude oil was crystallized from DIPE, filtered off, washed with DIPE and dried, yielding 2.1 g (50%) of (B)-4,5-dihydro-N-[4-(2-phenyl-1,3-dioxolan-2-yl)phenyl]-3-(3-pyridinyl)-5-isoxazolecarboxamide. (compound 375)

EXAMPLE B.23 a.) Trimethyl silyl cyanide (0.040 mol) was added to a mixture of compound (1) (0.013 mol) and $ZnI_2$ (0.015 mol) in $CH_2Cl_2$ (100 ml). The reaction mixture was stirred for 2 hours at 65° C. The reaction mixture was treated with 10% $NH_4Cl$, filtered over Celite, and the two layers of the filtrate were separated. The organic layer was dried ($Na_2SO_4$), filtered and the solvent was evaporated, yielding 6.3 g of (±)-N-[4-[cyano[(trimethylsilyl)oxy]phenylmethyl]phenyl]-4,5-dihydro-3-(3-pyridinyl)-5-isoxazolecarboxamide. (compound 494)

b.) HCl 3N (0.010 mol) was added to a solution of (±)-N-[4-[cyano[(trimethylsilyl)oxy] phenylmethyl] phenyl]-4,5-dihydro-3-(3-pyridinyl)-5-isoxazolecarboxamide (0.010 mol) in THF (50 ml). The reaction mixture was stirred for 15 minutes at 65° C. The reaction mixture was washed with water and extracted with EtOAc. The separated organic layer was dried ($Na_2SO_4$), filtered and the solvent was evaporated, yielding 4.2 g of (±)-N-[4-(cyanohydroxyphenylmethyl)phenyl]-4,5-dihydro-3-(3-pyridinyl)-5-isoxazolecarboxamide (compound 495).

c.) Chlorosulfonyl isocyanato (0.010 mol) was added to a solution of (±)-N-[4-(cyanohydroxyphenylmethyl)phenyl]-4,5-dihydro-3-(3-pyridinyl)-5-isoxazolecarboxamide (0.010 mol) in $CH_2Cl_2$ (40 ml). The reaction mixture was stirred for 3 hours at RT. Water (40 ml) was added and stirring was continued for one hour. The mixture was washed with an aqueous $NaHCO_3$ solution and extracted with 1-butanol. The organic layer was separated, dried ($Na_2SO_4$), filtered and the solvent was evaporated. The residue was purified by open column chromatography over silica gel (eluent: $CH_2Cl_2/CH_3OH$ 96/4, 90/10). The desired fractions were collected and the solvent was evaporated. The residue was crystallized from DIPE/methanol and dried, yielding 0.2 g (5%) of (±)-[cyano[4-[[[4,5-dihydro-3-(3-pyridinyl)-5-isoxazolyl]carbonyl] amino]phenyl]phenylmethyl] carbamate. (compound 75)

EXAMPLE B.24 a.) $PCl_5$ (0.027 mol) was added to a solution of (±)-N-[4-(cyanohydroxyphenylmethyl) phenyl]-4,5-dihydro-3-(3-pyridinyl)-5-isoxazolecarboxamide (0.023 mol) in THF (50 ml). The reaction mixture was stirred and refluxed for 2 hours. $Et_2O$ was added and the precipitate was filtered off and dried, yielding 7.2 g (80%) of (±)-N-[4-(chlorocyanophenylmethyl)phenyl]-4,5-dihydro-3-(3-pyridinyl)-5-isoxazolecarboxamide monohydrochloride (compound 496).

b.) A solution of (±)-N-[4-(chlorocyanophenylmethyl) phenyl]-4,5-dihydro-3-(3-pyridinyl)-5-isoxazolecarboxamide monohydrochloride (0.004 mol) in methanol (50 ml) was stirred and refluxed for 30 minutes. The solvent was evaporated. The residue was purified by high-performance liquid chromatography over silica gel ((I) eluent: $CH_2Cl_2CH_3OH$ 96/4; (II) eluent: $CH_2Cl_2/CH_3OH$ 97.5/2.5). The desired fractions were collected and the solvent was evaporated. The residue was repurified by high-performance liquid chromatography over Kromasil C18 (eluent: $CH_3OH/H_2O$ 70/30). The desired fractions were collected and the solvent was evaporated. The residue was crystallized from $Et_2O$/hexane, filtered off and dried, yielding 0.113 g (6%) of (±)-N-[4-cyanomethoxyphenylmethyl)phenyl]-4,5-dihydro-3-(3-pyridinyl)-5-isoxazolecarboximidamide (compound 76).

EXAMPLE B.25 a.) Acetic acid anhydride (0.03 mol) was added dropwise to a solution of (±)-N-[4-(cyanohydroxyphenylmethyl) phenyl]-4,5-dihydro-3-(3-pyridinyl)-5-isoxazolecarboximidamide (0.010 mol) in pyridine (80 ml), stirred at 0° C. The reaction mixture was stirred for 4 days at RT. The solvent was evaporated. The residue was dissolved in EtOAc and washed with water. The organic layer was separated, dried ($Na_2SO_4$), filtered, and the solvent was evaporated. The residue was purified by short open column chromatography over silica gel (eluent: $CH_2Cl_2/CH_3OH$ 92/8). The desired fractions were collected and the solvent was evaporated, yielding 2.7 g (61%) of (±)-[cyano-[4-[[[4,5-dihydro-3-(3-pyridinyl)-5-isoxazolyl]carbonyl]amino] phenyl]phenylmethyl]acetate. (compound 83)

b.) $(CH_3)_3SiN_3$ (0.010 mol) was added to compound (83) (0.004 mol) in $CH_2Cl_2$ (50 ml). $SnCl_4$ (0.525 ml) was added and the reaction mixture was stirred for 17 hours at RT. The reaction mixture was washed with a saturated aqueous $NaHCO_3$ solution. The resulting emulsion was filtered through dicalite. The layers were separated. The organic layer was washed with brine, dried ($Na_2SO_4$), filtered, and the solvent was evaporated. The residue was purified by high-performance liquid chromatography over silica gel (eluent: $CH_2Cl_2CH_3OH$ 98/2). The desired fractions were collected and the solvent was evaporated, yielding 1.1 g (59%) of (±)-N-[4-(azidocyanophenylmethyl)phenyl]-4,5-dihydro-3-(3-pyridinyl)-5-isoxazolecarboxamide. (compound 84)

c) A solution of (±)-N-[4-(azidocyanophenylmethyl) phenyl]-4,5-dihydro-3-(3-pyridinyl)-5-isoxazolecarboxamide (0.00472 mol) in THF (30 ml) was stirred at 0° C. under $N_2$ atmosphere. $NaBH_4$ (0.00315 mol) was added. Methanol (4 ml) was added dropwise and the resulting reaction mixture was warmed to room temperature and stirred for 16 hours. $NH_4Cl$, 20% was added and the mixture was stirred for 30 min. This mixture was extracted with $CH_2Cl_2$. The separated organic layer was washed with water, brine, dried, filtered and the solvent evaporated. The residue was purified by column chromatography over silica gel (eluent: $CH_2Cl_2/CH_3OH$ 96/4). The desired fractions were collected and the solvent was evaporated. The residue was partially dissolved in EtOAc and precipitated with hexane. The precipitate was filtered off and dried. Yielding: 0.200 g of (±)-N-[4-(4,5-dihydro-5-methylene-4-phenyl-1H-1,2,3-triazol-4-yl)phenyl]-4,5-dihydro-3-(3-pyridinyl)-5-isoxazolecarboxamide (10%, white solid) (compound 497).

EXAMPLE B.26

Chloromethoxymethane (0.025 mol) and $P_2O_5$ (2.0 g) were added to a solution of compound (375) (0.0085 mol) in $CHCl_3$ (50 ml). The reaction mixture was stirred for 4 hours at RT. The reaction mixture was poured out into a cold saturated aqueous $Na_2CO_3$ solution and this mixture was extracted with diethyl ether. The aqueous layer was separated and extracted with EtOAc. The combined organic layers were dried ($Na_2SO_4$), filtered and the solvent was evaporated. The residue was purified by short open column chromatography over silica gel (eluent: $CH_2Cl_2/CH_3OH$ 98/2 to 95/5). The desired fractions were collected and the solvent was evaporated. The residue was purified twice by high-performance liquid chromatography over silica gel ((I) eluent: $CH_2Cl_2/(CH_3OH/NH_3)$ 98/2); (II) eluent: $CH_2Cl_2/CH_3OH$ 98/2). The desired fractions were collected and the solvent was evaporated. The residue was dissolved in $Et_2O$/2-propanol 1/1 and converted into the hydrochloric acid salt (1:1). The precipitate was filtered off and dried, yielding 0.1 g of (±)-N-[4-[cyano(methoxymethoxy)phenylmethyl] phenyl]-4,5-dihydro-3-(3-pyridinyl)-5-isoxazolecarboxamide monohydrochlorid. (compound 87)

EXAMPLE B.27

Iodomethane (0.010 mol) was added to a suspension of compound (1) (0.00403 mol) in 2-propanone (20 ml). In a Parr pressure vessel, the reaction mixture was heated for 20 hours at 50° C. The solvent was evaporated. The residue was treated with diethyl ether, filtered off under $N_2$, and dried, yielding 1.8 g (89%) of (±)-3-[5-[[(4-benzoylphenyl)amino]carbonyl]-4,5-dihydro-3-isoxazolyl]-1-methylpyridinium iodide (compound 448).

EXAMPLE B.28 a.) A suspension of compound (50) (0.021 mol), N,N-dimethyl-4-pyridinamine (0.042 mol) and triethylamine (catalytic quantity) in $CH_2Cl_2$ (100 ml) was stirred at RT. Acetic acid anhydride (0.042 mol) was added and the resulting reaction mixture was stirred and refluxed until a clear solution was obtained. The mixture was stirred and refluxed for an extra 30 minutes, then cooled to RT. Water was added. The organic layer was separated, dried ($MgSO_4$), filtered and the solvent was evaporated under reduced pressure, yielding 8.0 g of (±)-[4-[[[4,5-dihydro-3-(3-pyridinyl)-5-isoxazolyl]carbonyl]amino]phenyl]phenylmethyl acetate (compound 414).

b.) (±)-[4-[[[4,5-dihydro-3-(3-pyridinyl)-5-isoxazolyl]carbonyl]amino]phenyl]phenylmethyl acetate (0.019 mol) was separated into its enantiomers by chiral column chromatography over Chiralcel OJ (eluent: 100% methanol). The desired fraction group was collected and the solvent was evaporated, yielding 0.3 g of (S)-[4-[[[4,5-dihydro-3-(3-pyridinyl)-5-isoxazolyl]carbonyl]amino]phenyl]phenylmethyl acetate (compound 498).

c.) NaOH 1N (1 ml) was added dropwise to a stirred solution of (S)-[4-[[[4,5-dihydro-3-(3-pyridinyl)-5-isoxazolyl]carbonyl]amino]phenyl]phenylmethyl acetate (0.001 mol) in methanol (20 ml) and THF (20 ml) and the reaction mixture was stirred for one hour at RT. The solvent was evaporated under reduced pressure. The white solid residue was taken up into methanol. The precipitate was filtered off, washed with methanol and diethyl ether, then dried, yielding 0.2 g (92%) of (S)-4,5-dihydro-N-[4-(hydroxyphenylmethyl)phenyl]-3-(3-pyridinyl)-5-isoxazolecarboxamide (compound 57).

EXAMPLE B.29

1-Chloro-2,4-pyrrolidinedione (0.011 mol; 98%) was added portionwise to a solution of 5-pyrimidinecarboxaldehyde, oxime (0.036 mol) in DMF (50 ml) and this mixture was heated to 50° C. to start the reaction. The mixture was cooled to RT. Pyridine (0.28 ml) was added. The rest of 1-chloro-2,4-pyrrolidinedione (0.043 mol) was added portionwise and the mixture was stirred for 3 hours at RT. N-(4-benzoylphenyl)propenamide (0.025 mol) was added. Triethylamine (0.053 mol) was added dropwise and the resulting reaction mixture was stirred overnight at RT. The crude mixture was washed with water, then extracted with EtOAc. The organic layer was separated, and the solvent was evaporated. The residue was washed with water and extracted with $CH_2Cl_2$. The separated organic layer was dried ($Na_2SO_4$), filtered and the solvent was evaporated. The residue was crystallized from $CH_3OH$, washed with diethyl ether and hot $CH_2Cl_2$, dried and repurified by HPLC over silica gel (eluent: $CH_2Cl_2/CH_3OH$ 97/3). The pure fractions were collected and the solvent was evaporated, yielding 3.5 g of (±)-N-(4-benzoylphenyl)-4,5-dihydro-3-(5-pyrimidinyl)-5-isoxazolecarboxamide (compound 349)

EXAMPLE B.30 a.) $NaBH_4$ (0.054 mol) was added to a solution of compound (3) (0.054 mol) in methanol (300 ml). The reaction mixture was stirred overnight at RT. The precipitate was filtered off, washed with $CH_3OH$ and DIPE, then dried, yielding 18 g (89%) of (5S)-4,5-dihydro-N-[4-(hydroxyphenylmethyl)phenyl]-3-(3-pyridinyl)-5-isoxazolecarboxamide (compound 499).

b.) (5S)-4,5-dihydro-N-[4-(hydroxyphenylmethyl)phenyl]-3-(3-pyridinyl)-5-isoxazolecarboxamide (0.027 mol) was suspended in $CH_2Cl_2$ (250 ml). HCl, gas (excess) was allowed to bubble through the suspension for 2 minutes. $SOCl_2$ (0.097 mol) was added dropwise and the reaction mixture was stirred and refluxed for 4 hours. The solvent was evaporated under reduced pressure. Toluene was added and azeotroped on the rotary evaporator (2×). The residue was stirred in toluene. The precipitate was filtered off, washed with toluene and dried, yielding 11.5 g (100% crude yield) of (5S)-N-[4-(chlorophenylmethyl)phenyl]-4,5-dihydro-3-(3-pyridinyl)-5-isoxazolecarboxamide monohydrochloride (compound 500).

c.) NaH (0.047 mol) was added portionwise to a solution of bis(1,1-dimethylethyl) imidodicarbonate (0.023 mol) in DMF (250 ml), stirred at RT ($H_2$ gas evolution). The mixture was stirred for 30 minutes at RT. (5S)-N-[4-(chlorophenylmethyl)phenyl]-4,5-dihydro-3-(3-pyridinyl)-5-isoxazolecarboxamide monohydrochloride (0.0233 mol) was added portionwise and the resulting reaction mixture was stirred vigorously for 1 hour at RT ($H_2$ gas evolution). The solvent was evaporated under reduced pressure. The residue was partitioned between water and $CH_2Cl_2$. The separated organic layer was dried ($MgSO_4$), filtered and the solvent evaporated under reduced pressure, yielding 1,1-dimethylethyl (5S)-[[4-[[[4,5-dihydro-3-(3-pyridinyl)-5-isoxazolyl]carbonyl]amino]phenyl]phenylmethyl][(1,1-dimethylethoxy)carbonyl]carbamate (compound 501).

d.) (50 ml) was added dropwise to a solution of 1,1-dimethylethyl (5S)-[[4-[[[4,5-dihydro-3-(3-pyridinyl)-5-isoxazolyl]carbonyl]amino]phenyl]phenylmethyl][(1,1-dimethylethoxy)carbonyl]carbamate (0.0233 mol) in $CH_2Cl_2$ (500 ml), stirred at RT ($CO_2$ gas evolution). The reaction mixture was stirred for 48 hours at RT. The reaction mixture was added dropwise to a saturated aqueous $NaHCO_3$ solution, and this mixture was extracted with $CH_2Cl_2$. The separated organic layer was dried ($MgSO_4$), filtered and the solvent evaporated under reduced pressure. The residue was purified by short column chromatography over silica gel (eluent: $CH_2Cl_2/(CH_3OH/NH_3)$ 97.5/2.5). The desired fractions were collected and the solvent was evaporated under reduced pressure. The resultant oil was stirred in EtOAc, filtered off, washed with EtOAc and DIPE, then dried, yielding 2.5 g (30%) of (±)-N-[4-(aminophenylmethyl) phenyl]-4,5-dihydro-3-(3-pyridinyl)-5-isoxazolecarboxamide (compound 502).

e.) (±)-N-[4-(aminophenylmethyl) phenyl]-4,5-dihydro-3-(3-pyridinyl)-5-isoxazole carboxamide (0.007 mol) was separated by chiral HPLC over Chiralpak AD (250 g, 35 bar, flow: 30 ml/minute, wavelength: 220 nm, 0.300 g per injection dissolved in 40 ml of eluent; eluent: $CH_3CN/C_2H_5OH$ 80/20). Two desired fraction groups were collected and their solvent was evaporated. The (A)-residue was stirred in EtOAc, filtered off, washed with some DIPE and dried, yielding 0.9 g [5S-(A)]-N-[4-(aminophenylmethyl) phenyl]-4,5-dihydro-3-(3-pyridinyl)-5-isoxazolecarboxamide. (compound 205)

EXAMPLE B.31

Intermediate (19) (0.013 mol) was stirred in $CH_2Cl_2$. HCl (gas) was allowed to bubble through this mixture (for a while). The solvent was evaporated. The residue was taken up into thionyl chloride, then stirred and refluxed for 3 hours. Toluene was added and the solvent was evaporated to give residue (A*). Half the residue (A*) was stirred in $CH_2Cl_2$, then partitioned over 12 vials, filled with 2-pyridinemethanamine (0.1 g) in $CH_2Cl_2$ (4 ml) (so each vial contained ±0.0005 mol of reactant (A*)). Triethylamine (0.5 ml) was added and the resulting reaction mixture was stirred overnight at RT. The desired compound was isolated and purified by high-performance liquid chromatography over Kromasil Spherical underivated silica gel (55 g, 60 Å, 5 µm; eluent: $CH_2Cl_2/CH_2Cl_2/CH_2OH$ 9/1)/$CH_3OH$. The desired fractions were collected and the solvent was evaporated, yielding 0.055 g of (±)-4,5-dihydro-3-(3-pyridinyl)-N-[4-[[(2-pyridinylmethyl)amino]carbonyl]phenyl]-5-isoxazolecarboxamide. (compound 271)

EXAMPLE B.32

Hydroxylamine (0.0067 mol) and sodiumacetate (0.0067 mol) were added to a mixture of (±)-4,5-dihydro-3-(3-pyridinyl)-N-[4-(3-pyridinylcarbonyl)phenyl]-5-isoxazolecarboxamide (0.0053 mol) in ethanol (20 ml) and THF (10 ml). The reaction mixture was stirred and refluxed for 5.5 hours, then stirred for 18 hours at room temperature. The solvent was evaporated. The residue was taken up into 1-butanol, then washed with water. The organic layer was separated, dried ($Na_2SO_4$), filtered and the solvent was evaporated. The residue was crystallized from $CH_2Cl_2/Et_2O$/hexane, filtered off and dried. Yield: 0.37 g of 4,5-dihydro-N-[4-[(hydroxyimino)-3-pyridinylmethyl]phenyl]-3-(3-pyridinyl)-5-isoxazolecarboxamide (18%) (compound 503).

EXAMPLE B.33

A mixture of (5S)-N-[4-(chlorophenylmethyl)phenyl]-4,5-dihydro-3-(3-pyridinyl)-5-isoxazolecarboxamide (0.00938 mol) in 4-methyl-2-butanone (100 ml) was stirred at room temperature under $N_2$ flow. 2-Propane-oxime (0.0281 mol) and then methanesulfonic acid (0.0206 mol) were added. The mixture was stirred at 100° C. for 2 hours and at room temperature for 2 hours. The upper layer was decanted. The residue was stirred in $CH_2Cl_2$ (100 ml). A half saturated $NaHCO_3$ solution (50 ml) was added. Then $CH_2Cl_2/CH_3OH$ 50/50 (25 ml) was added. The organic layer was separated, combined with the decanted layer, dried ($MgSO_4$), filtered, washed with $CH_2Cl_2/CH_3OH$ 90/10 and the solvent was evaporated. The residue was co-evaporated with toluene. This fraction was purified by HPLC (eluent: $NH_4O$ Ac 0.5% in $H_2O/CH_3CN$ 90/10)/$CH_3OH/CH_3CN$ 75/25/0, 0/50/50, 0/0/100 and 75/25/0). Two desired fractions were collected and the solvent was evaporated. Each residue was stirred in DIPE. The precipitate was filtered off, washed and dried in vacuo at 50° C. Yielding: 0.194 g of (5S)-4,5-dihydro-N-[4-[[[(1-methylethylidene)amino]oxo]phenylmethyl]phenyl]-3-(3-pyridinyl)-5-isoxazolecarboxamide (compound 504) and 0.56 g of (5S)-N-[4-[[[(1,3-dimethylbutylidene)amino]oxy]phenylmethyl]phenyl]-4,5-dihydro-3-(3-pyridinyl)-5-isoxazolecarboxamide (compound 410).

EXAMPLE B.34 a.) Triethylamine (0.0206 mol) was added dropwise to a mixture of intermediate (3) (0.0133 mol), intermediate (23) (0.01 mol) and dimethylpyrilidylamine (catalytic quantity) in $CH_2Cl_2$ (70 ml, dry), stirred and cooled on an ice-water bath. The resulting reaction mixture was stirred overnight at room temperature. The crude reaction mixture was washed with water and brine, and extracted. The separated organic layer was dried ($Na_2SO_4$), filtered, and the solvent was evaporated. The residue was purified by open column chromatography over silica gel (eluent: $CH_2Cl_2/CH_3OH$ 96/4). The desired fractions were collected and the solvent was evaporated. A sample (1 g) was purified by high-performance liquid chromatography (eluent: $CH_2Cl_2/CH_3OH$ 98/2). The pure fractions were collected and the solvent was evaporated. Yielding: 0.63 g (±)-N-[4-(1-cyano-3-methoxy-1-phenylpropyl)phenyl]-4,5-dihydro-3-(3-pyridinyl)-5-isoxazolcarboxamide (compound 399).

b.) $BBr_3$ (0.01566 mol) was added dropwise to a solution of compound (399) (0.00522 mol) in $CH_2Cl_2$ (50 ml), cooled at −60° C. The resulting reaction mixture was stirred for 3 hours at room temperature. The crude reaction mixture was treated with water and $Na_2CO_3$ until only slightly acidic pH. This mixture was extracted. The separated organic layer was dried ($Na_2SO_4$), filtered and the solvent was evaporated. The residue was purified first by open column chromatography over silica gel (eluent: $CH_2Cl_2$/2-propanone 96/4 and $CH_2Cl_2/CH_3OH$ 96/4), then by HPLC (eluent: $CH_2Cl_2/CH_3OH$ 96/4). The desired fractions were collected and the solvent was evaporated. The impure residue was washed with a 2 N HCl solution and extracted with $CH_2Cl_2$. The separated organic layer was dried ($Na_2SO_4$), filtered and the solvent was evaporated. The residue was dissolved in 2-propanol and converted into the hydrobromic acid salt (1:1). The precipitate was filtered off and dried. Yielding: 0.36 g (±)-N-[4-(1-cyano-3-hydroxy-1-phenylpropyl)phenyl]-4,5-dihydro-3-(3-pyridinyl)-5-isoxazolecarboxamide monohydrobromide (14%) (compound 505).

EXAMPLE B.35

A mixture of (±)-N-[4-(cyanophenylmethyl)phenyl]-4,5-dihydro-3-(3-pyridinyl)-5-isoxazolecarboxamide (0.0157 mol) and poly(oxymethylene) (0.0627 mol) in pyridine (31.2 ml) was cooled with an ice-water bath. Triton B (1.56 ml) was added dropwise and the resulting reaction mixture was stirred for 2 days at room temperature. The crude reaction mixture was washed with water and this mixture was extracted with EtOAc. The separated organic layer was dried ($Na_2SO_4$), filtered and the solvent was evaporated. The residue was purified first by short column chromatography over silica gel (eluent: $CH_2Cl_2$/2-propanone 96/4 and 90/10 and $CH_2Cl_2/CH_3OH$ 96/4), then by HPLC (eluent: $CH_2Cl_2/(CH_3OH/NH_3)$ 96/4). The pure fractions were collected and the solvent was evaporated. Yielding: 0.52 g of (±)-N-[4-(1-cyano-2-hydroxy-1-phenylethyl)phenyl]-4,5-dihydro-3-(3-pyridinyl)-5-isoxazolecarboxamide (8%) (compound 506).

EXAMPLE B.36

A mixture of (±)-N-[4-(cyanophenylmethyl)phenyl]-4,5-dihydro-3-(3-pyridinyl)-5-isoxazolecarboxamide (0.00628 mol), hydroxylamine (0.01256 mol) and triethylamine (0.01256 mol) in ethanol (10 ml) and THF (10 ml) was stirred and refluxed for 22 hours. The solvent was evaporated. Water was added. The precipitate was filtered off and dissolved in $CH_2Cl_2/CH_3OH$. The organic solution was dried ($MgSO_4$), filtered and the solvent was evaporated. The residue was purified by HPLC over silica gel (eluent: $CH_2Cl_2/CH_3OH$ 94/6; $CH_2Cl_2/(CH_3OH/NH_3)$ 95/5). The desired fractions were collected and the solvent was evaporated. The residue was crystallized from $CH_2Cl_2/Et_2O$, filtered off, washed with methanol and dried. Yield: 0.26 g of (±)-N-[4-[2-amino-2-(hydroxyimino)-1-phenylethyl]phenyl]-4,5-dihydro-3-(3-pyridinyl)-5-isoxazolecarboxamide (10%) (compound 507). Mixture of diastereomers: 95/5

EXAMPLE B.37

In the following reaction with $N_2$ atmosphere, a mixture of compound (412) (0.00562 mol), $CH_2Cl_2$ (40 ml), triethylamine (0.0112 mol) and N,N-dimethyl-4-pyridinamine (catalytic quantity) was stirred on an ice-bath. Isopropyl chlorocarbonate (0.00675 mol; 1 M/toluene) was added dropwise and the reaction mixture was stirred for 30 min at 0° C., then for 30 min at room temperature. The reaction mixture was stirred and refluxed overnight. More isopropyl chlorocarbonate (4.5 ml) was added and the reaction mixture was stirred and refluxed for 24 hours. THF, p.a. (15 ml; p.a., dried over molecular sieves) was added and the reaction mixture was stirred and refluxed for 24 hours. G (25 ml; p.a., dried over molecular sieves) was added and the reaction mixture was stirred overnight at 80° C. More isopropyl chlorocarbonate (5 ml) was added and the resulting reaction mixture was stirred for 24 hours at 80° C. Again, isopropyl chlorocarbonate (5 ml) was added and the mixture was stirred for 75 min at 90° C. The solvent was evaporated. Toluene was added and azeotroped on the rotary evaporator. The residue was stirred in $CH_2Cl_2$, filtered off, and the precipitate (mainly starting material compound (412)) was washed with $CH_2Cl_2$. The filtrate was evaporated. The residue was co-evaporated with toluene. The residue was purified by HPLC over silica gel (eluent: $CH_2Cl_2$/2-propanol 96/4). The desired fractions were collected and the solvent was evaporated. The residue was stirred in DIPE, filtered off, washed and dried (vacuum, 50° C.). Yield: 0.115 g of [5S(A)]-[4-[[[4,5-dihydro-3-(3-pyridinyl)-5-isoxazolyl]carbonyl]amino]phenyl]phenylmethyl 1-methylethyl carbonic acid (ester) (compound 508).

EXAMPLE B.38

HCl (8.5 ml) was added to a solution of (±)-4,5-dihydro-N-[4-[1-phenyl-2-(triphenylmethoxy)ethyl]phenyl]-3-(3-pyridinyl)-5-isoxazolecarboxamide (0.00857 mol) in 1,4-dioxane (250 ml). The reaction mixture was stirred for one hour at room temperature. Water was added. This mixture was extracted with $CH_2Cl_2$ and 1-butanol. The combined organic layers were dried ($Na_2SO_4$), filtered and the solvent evaporated. The residue was purified by short open column chromatography over silica gel (eluent: $CH_2Cl_2$/$CH_3OH$ 98/2, 96/4, and 92/8). The desired fractions were collected and the solvent was evaporated. The residue was purified by HPLC over silica gel (eluent: $CH_2Cl_2$/($CH_3OH$/$NH_3$) 97/3). The desired fractions were collected and the solvent was evaporated. The residue was crystallized from $CH_2Cl_2$/$Et_2O$/hexane, filtered off, washed with $CH_3CN$ and dried. Yield: 1.26 g of (±)-4,5-dihydro-N-[4-(2-hydroxy-1-phenylethyl)phenyl]-3-(3-pyridinyl)-5-isoxazolecarboxamide (38%) (compound 509).

EXAMPLE B.39 a) Compound (51) (0.1032 mol) was separated into its optical enantiomers by high-performance liquid chromatography (AD, 11 cm; eluent gradient: $C_2H_5OH$/$CH_3CN$ 90/10; flow: 500 ml/min; wavelength: 220 nm). Two fraction groups were collected and their solvent was evaporated, to give residues [(I)=(B1)-4,5-dihydro-N-[4-(1-hydroxy-1-phenylethyl)phenyl]-3-(3-pyridinyl)-5-isoxazolecarboxamide) and (II)=(A2)-4,5-dihydro-N-[4-(1-hydroxy-1-phenylethyl)phenyl]-3-(3-pyridinyl)-5-isoxazolecarboxamide)]. Residue (I) was stirred in methanol. The precipitate was filtered off, washed with methanol and dried (vacuum, 50° C., 24 hours). Yielding: 7.3 g of (B1)-4,5-dihydro-N-[4-(1-hydroxy-1-phenylethyl)phenyl]-3-(3-pyridinyl)-5-isoxazolecarboxamide (compound 510). Residue (II) was stirred in methanol. The precipitate was filtered off, washed with methanol and dried (vacuum, 50° C., 24 hours). Yielding: 5.91 g of (A2)-4,5-dihydro-N-[4-(1-hydroxy-1-phenylethyl)phenyl]-3-(3-pyridinyl)-5-isoxazolecarboxamide (compound 411).

b) Compound (51) (0.0052 mol) was separated into 4 optical enantiomers by high-performance liquid chromatography (5 cm DAC, AC, 250 g; eluent gradient: $C_2H_5OH$/$CH_3CN$ from 90/10 to 70/30). Four fraction groups were collected and their solvent was evaporated, to give 4 residues, which were stirred in diethyl ether, the resulting precipitates were filtered, washed with diethyl ether and dried (vacuum, 50° C., 16 hours). Residue (I) yielded: 0.29 g of (A1)-4,5-dihydro-N-[4-(1-hydroxy-1-phenylethyl)phenyl]-3-(3-pyridinyl)-5-isoxazolecarboxamide. Residue (II) yielded: 0.23 g compound (510) (+). Residue (III) yielded: 0.32 g of (B2)-4,5-dihydro-N-[4-(1-hydroxy-1-phenylethyl)phenyl]-3-(3-pyridinyl)-5-isoxazolecarboxamide (−). Residue (IV) yielded: 0.30 g of (A2)-4,5-dihydro-N-[4-(1-hydroxy-1-phenylethyl)phenyl]-3-(3-pyridinyl)-5-isoxazolecarboxamide (+) (compound 511).

EXAMPLE B.40 a.) Reaction under $N_2$ atmosphere. A mixture of 1,3-dioxolane, 2-[4-(bromomethyl)phenyl]-2-phenyl (0.0051 mol), Zn/Cu couple (0.0076 mol) in N,N-dimethylacetamide (1.1 ml) and benzene (13 ml) was stirred for 2 hours at 60° C. The heating bath was removed and the mixture was treated with a solution of $Pd(PPh_3)_4$ (0.000066 mol) in benzene (1 ml). The mixture was stirred for 5 min. 2-propenoyl chloride (0.0033 mol) was added and the resulting reaction mixture was stirred for 90 min at room temperature. The crude reaction mixture was diluted with EtOAc, filtered over dicalite and the filtrate was washed with an aqueous $NH_4Cl$ solution, then extracted. The separated organic layer was dried ($Na_2SO_4$), filtered and the solvent was evaporated (without heating). Yielding: 0.74 g of 1-[4-(2-phenyl-1,3-dioxolan-2-yl)phenyl]-3-buten-2-one (76%, used in next reaction step, without further purification (compound 512).

b.) N-Chlorosuccinimide (0.0038 mol) was added portionwise to a mixture of nicotinaldoxime (0.0025 mol) and pyridine (0.02 ml) in $CHCl_3$ (20 ml). This mixture was stirred for 3 hours at 40° C., then cooled. A solution of R153208 (0.0025 mol) in $CHCl_3$ (6 ml) was added. Triethylamine (0.0038 mol) was added dropwise and the resulting reaction mixture was stirred overnight at room temperature. The crude reaction mixture was washed with water and extracted. The separated organic layer was dried ($Na_2SO_4$), filtered and the solvent was evaporated. The residue was purified by open column chromatography over silica gel (eluent: $CH_2Cl_2$/$CH_3OH$ 100/0, 99/1, 98/2 and 96/4). The pure fractions were collected and the solvent was evaporated. Yielding: 0.87 g (±)-1-[4,5-dihydro-3-(3-pyridinyl)-5-isoxazolyl]-2-[4-(2-phenyl-1,3-dioxolan-2-yl)phenyl]ethanone (83%, used in next reaction step, without further purification) (compound 513).

c.) A mixture of (±)-1-[4,5-dihydro-3-(3-pyridinyl)-5-isoxazolyl]-2-[4-(2-phenyl-1,3-dioxolan-2-yl)phenyl]

ethanone (0.00227 mol) in 10% HCl (5.4 ml) and THF (5.4 ml) was stirred for 3 hours at room temperature, then cooled and treated with water and $Na_2CO_3$ until neutral pH. This mixture was extracted with EtOAc. The separated organic layer was dried ($Na_2SO_4$), filtered and the solvent was evaporated. The residue was purified first by open column chromatography over silica gel (eluent: $CH_2Cl_2/CH_3OH$ 96/4), then by HPLC (eluent: $CH_2Cl_2/CH_3OH$ 98/2). The purest fractions were collected and the solvent was evaporated. The residue was dissolved in diethyl ether/2-propanol and converted into the hydrochloric acid salt (1:1). The precipitate was filtered off and dried. Yielding: 0.14 g (±)-2-(4-benzoylphenyl)-1-[4,5-dihydro-3-(3-pyridinyl)-5-isoxazolyl]ethanone monohydrochloride (15%) (compound 514).

EXAMPLE B.41

A suspension of intermediate (3) (0.014 mol) in THF (100 ml) was stirred at 0° C. (ice bath). 1-(3-phenylpropyl)-piperazine (0.046 mol) was added in one portion and the reaction mixture was allowed to reach room t°. Stirring at room t° was continued for 2 h. Water was added to the reaction mixture and ammonia was added. This mixture was extracted with $CH_2Cl_2$. The organic layer was separated, dried ($MgSO_4$), filtered and the solvent was evaporated. The residue (9.3 g) was purified over silica gel on a glass filter (eluent: $CH_2Cl_2/CH_3OH$ 95/5). The pure fractions were collected and evaporated. The residue (4.4 g) was crystallized from ethyl acetate (25 ml). The crystals were filtered off, washed with DIPE, then dried (vacuum; 50° C.). Yielding: 2.15 g (±)-1-[[4,5-dihydro-3-(3-pyridinyl)-5-isoxazolyl]carbonyl]-4-(3-phenylpropyl)-piperazine (40%) (compound 515).

EXAMPLE B.42

A mixture of 3,3a,4,5-tetrahydroisoxazolo[4,3-c]quinolin-3-carboxylic acid (0.0064 mol), 4-(4-fluorobenzoyl)-piperidine (0.0053 mol) and 1-hydroxy-1H-benzotriazole (0.0064 mol) in THF (20 ml) was stirred at room temperature. A solution of N,N'-dicyclohexylcarbodiimide (0.0064 mol) in $CH_2Cl_2$ (77 ml) was added dropwise and the resulting reaction mixture was stirred overnight at room temperature. The crude reaction mixture was filtered over dicalite, and the filtrate was washed with brine, then extracted with $CH_2Cl_2$. The separated organic layer was dried ($Na_2SO_4$), filtered and the solvent was evaporated. The residue was washed with DIPE, then purified by two short open column chromatographies ((1) over silica gel, eluents: $CH_2Cl_2$ and $CH_2Cl_2$/2-peopanone 96/4; (2) over Kromasil C18, eluent: methanol). The pure fractions were collected and the solvent was evaporated. Yielding: 0.17 g of (cis)-4-(4-fluorobenzoyl)-1-[(3,3a,4,5-tetrahydroisoxazolo[4,3-c]quinolin-3-yl)carbonyl]piperidine (6%) (compound 516).

EXAMPLE B.43

Diisopropylethylamine (0.5 ml) was added to N,N-dimethyl-2-(4-piperidinyloxy)-4-pyrimidinamine (0.100 g) in $CH_2Cl_2$ (2 ml). N,N-Dimethyl-4-pyridinamine (catalytic quantity) was added and the mixture was stirred at room temperature. A solution of diisopropylethylamine (0.00061 mol) in $CH_2Cl_2$ (5 ml) and DMA (2 ml) was added dropwise and the resulting reaction mixture was stirred overnight at room temperature. Pyridine (0.5 ml) was added and the reaction mixture was stirred overnight at 60° C. The desired compound was isolated and purified by reversed-phase high-performance liquid chromatography over Kromasil C18 (22 g, 100 Å, 5 µm) (column: one inch I.D.; eluent: ((0.05% $NH_4AOc$ in $H_2O$)/$CH_3CN$ 90/10)/$CH_3OH$/$CH_3CN$ (0 min) 75/25/0, (10.50 min) 0/50/50, (16.50 min) 0/0/100, (18.01–20 min) 75/25/0). The desired fractions were collected and the solvent was evaporated. Yielding: 0.080 g of 4-[[4-(dimethylamino)-2-pyrimidinyl]oxy]-1-[[4,5-dihydro-3-(3-pyridinyl)isoxazole-5-yl]carbonyl]piperidine (compound 517). This fraction (0.080 g) was dissolved in DMSO (10.1 ml) and used for pharmacological tests.

EXAMPLE B.44 a.) Diisopropylethylamine (0.0104 mol) was added dropwise to a mixture of intermediate (3) (0.0062 mol), intermediate (21) (0.0052 mol) and N,N-dimethyl-4-pyridinamine (catalytic quantity) in $CH_2Cl_2$ (50 ml), stirred at 0° C. The reaction mixture was stirred for 20 hours at room temperature. The solvent was evaporated under reduced pressure. The residue was taken up into 1-butanol. The organic solution was washed with water, dried ($Na_2SO_4$), filtered and the solvent was evaporated. The residue was crystallized from $CH_2Cl_2$ and the impure solid was purified by high-performance liquid chromatography over silica gel (eluent: $CH_2Cl_2/CH_3OH$ 95/5). The desired fractions were collected and the solvent was evaporated. Yielding: 0.38 g of (±)-N-[4-(2-amino-1-hydroxy-2-oxo-1-phenylethyl)phenyl]-4,5-dihydro-3-(3-pyridinyl)-5-isoxazolecarboxamide (15%) (compound 330).

b.) $PCl_5$ (0.0028 mol) was added of compound (330) (0.0024 mol) in THF (20 ml). The reaction mixture was stirred for one hour at room temperature. The precipitate was filtered off and dried. Yielding: 0.8 g of (±)-N-[4-(2-amino-1-chloro-2-oxo-1-phenylethyl)phenyl]-4,5-dihydro-3-(3-pyridinyl)-5-isoxazolecarboxamide monohydrochloride (71%; 90% pure by NMR, used in next reaction step, without further purification) (compound 158).

c.) A solution of compound (518) (0.0025 mol) in N-methylmorpholine (20 ml) was stirred for 18 hours at room temperature. The solvent was evaporated. The residue was purified by high-performance liquid chromatography over silica gel (eluent: $CH_2Cl_2/CH_3OH$ 95/5). The desired fractions were collected and the solvent was evaporated. The residue was taken up into $CH_2Cl_2$, washed with an aqueous $NaHCO_3$ solution and with water. The organic layer was separated, dried ($Na_2SO_4$), filtered and the solvent was evaporated. The residue was crystallized from $CH_2Cl_2$/$Et_2O$, filtered off and dried. Yielding: 0.27 g of (±)-α-[4-[[[4,5-dihydro-3-(3-pyridinyl)-5-isoxazolyl]-carbonyl]amino]phenyl]-α-phenyl-4-morpholineacetamide monohydrate (22%) (compound 519).

EXAMPLE B.45

A mixture of 4-aminochalcone (0.005 mol) and triethylamine (0.01 mol) in $CH_2Cl_2$ (25 ml) was stirred at 5–10° C. Intermediate (3) (0.005 mol) was added portionwise over 30 min. The mixture was stirred for 2 hours at 5–10° C., then for 2 hours at room temperature. Intermediate 3 (0.0025 mol) and triethylamine (0.005 mol) were added. The reaction mixture was stirred over the weekend at room temperature. The precipitate was filtered off and recrystallized from $CH_3CN$ (50 ml). The precipitate was filtered off, washed with DIPE and dried. Yield: 0.7 g of (compound 520)

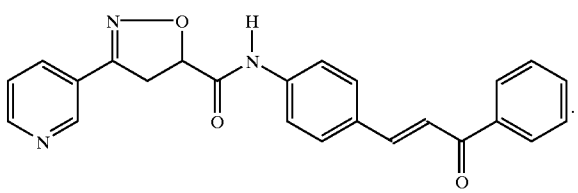

EXAMPLE B.46

Intermediate (3) (0.01 mol) was added to 4'-amino-2-azachalcone (0.008 mol) and diisopropylethylamine (0.02 mol) in CH$_2$Cl$_2$ (150 ml), stirred at 0° C. The reaction mixture was stirred while warming up to room temperature for 3 hours. The precipitate was filtered off, washed with water and DIPE, then dried under vacuum. Yield: 2.40 g (compound 521)

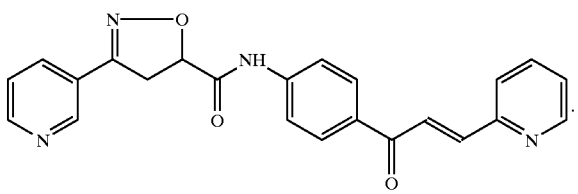

(75.3%)

EXAMPLE B.47

Intermediate (3) (0.0274 mol) was added portionwise to a mixture of 1-(p-aminophenyl)-1H-benzotriazole (0.0228 mol) and diisopropylethylamine (0.0548 mol) in CH$_2$Cl$_2$ (200 ml), stirred at 0° C. The reaction mixture was stirred for 3 hours at 0° C. Methanol and water were added. The organic layer was separated, dried (MgSO$_4$), filtered and the solvent was evaporated under reduced pressure. The residue was purified by column chromatography over Kromasil spherical silica gel (200 g, 100 Å, 5 μm; eluent: CH$_2$Cl$_2$/ (CH$_2$Cl$_2$/CH$_3$OH 90/10)/CH$_3$OH (0 min) 100/0/0, (34 min) 50/50/0, (40 min) 50/0/50, (43 min) 0/0/100, (46.6–60 min) 100/0/0). The desired fractions were collected and the solvent was evaporated under reduced pressure (50° C., 16 hours). Yielding: 1.57 g of (compound 522)

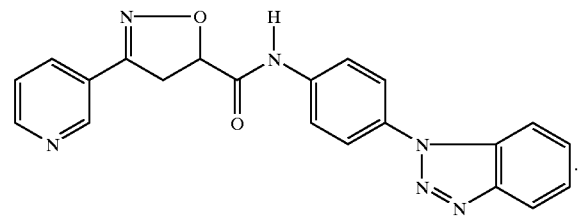

EXAMPLE B.48

A mixture of isoxazole,5-(4-aminophenyl)-3-phenyl (0.01 mol) and triethylamine (0.22 mol) in CH$_2$Cl$_2$ (50 ml) was stirred at 5° C. Intermediate (3) (0.011 mol) was added portionwise over one hour. The reaction mixture was stirred for one hour at 5° C., then overnight at room temperature. The precipitate was filtered off, washed with 2-propanol, with water, again with 2-propanol and DIPE, then dried. Yield: 3.1 g (compound 523)

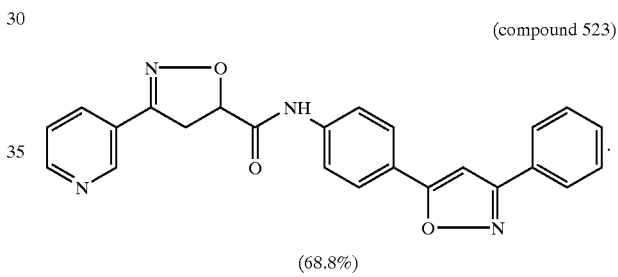

(68.8%)

Tables II to XIV list compounds of the present invention as prepared according to one of the above examples.

TABLE II

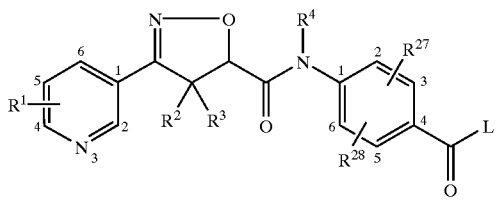

| Co. No. | Ex. No. | R$^1$ | R$^2$ | R$^3$ | R$^4$ | R$^{27}$ | R$^{28}$ | L | Physical Data |
|---|---|---|---|---|---|---|---|---|---|
| 1 | B1a | H | H | H | H | H | H | phenyl | |
| 2 | B1b | H | H | H | H | H | H | phenyl | (R) |
| 3 | B1b | H | H | H | H | H | H | phenyl | (S) |
| 4 | B1a | H | H | H | H | 3Cl | 5CH$_3$ | 4F-phenyl | — |
| 5 | B1a | H | H | H | H | 3Cl | H | 4Cl-phenyl | — |
| 6 | B1a | H | H | H | H | 5OCH$_3$ | H | phenyl | — |
| 7 | B1a | H | H | H | H | 5CH$_3$ | H | phenyl | — |
| 8 | B11 | H | H | H | H | H | H | 3CF$_3$-phenyl | — |
| 9 | B11 | H | H | H | H | H | H | 3OCH$_3$-phenyl | — |
| 10 | B11 | H | H | H | H | H | H | 3CH$_3$-phenyl | — |
| 11 | B11 | H | H | H | H | H | H | 4CH$_3$-phenyl | — |
| 12 | B11 | H | H | H | H | H | H | 3F-phenyl | — |

TABLE II-continued

[Structure: isoxazoline core with pyridine substituent (positions 4,5,6 on pyridine with R¹, N3, positions 1,2) connected via C(R²)(R³) to C(=O)N(R⁴)-phenyl (with R²⁷, R²⁸) bearing C(=O)-L group]

| Co. No. | Ex. No. | R¹ | R² | R³ | R⁴ | R²⁷ | R²⁸ | L | Physical Data |
|---|---|---|---|---|---|---|---|---|---|
| 13 | B11 | H | H | H | H | H | H | 4F-phenyl | — |
| 14 | B11 | H | H | H | H | H | H | 6Cl-phenyl | — |
| 15 | B5 | H | H | H | H | H | H | 4OCH₃-phenyl | — |
| 16 | B3 | H | H | H | H | H | H | [N-(p-tolyl)-3-(3-pyridyl)-4,5-dihydroisoxazole-5-carboxamide structure] | |
| 17 | B3 | H | H | H | H | H | H | 4NH₂-phenyl | — |
| 18 | B1a | H | H | H | H | H | H | 4Br-phenyl | — |
| 19 | B12 | H | H | H | H | H | H | [1-methyl-4-(dimethylamino)piperidine structure] | |
| 20 | B12 | H | H | H | H | H | H | [2-methyl-6,7-dimethoxy-1,2,3,4-tetrahydroisoquinoline structure] | |
| 21 | B12 | H | H | H | H | H | H | [1-methyl-1,2,3,4-tetrahydroquinoline structure] | — |
| 22 | B3a | 6Cl | H | H | H | H | H | phenyl | 123.6° C. |
| 23 | B1a | 2OCH₃ | H | H | H | H | H | phenyl | 124.5° C. |
| 24 | B1a | 6OCH₃ | H | H | H | H | H | phenyl | 172.9° C. |
| 25 | B29 | 2CH₃ | H | H | H | H | H | phenyl | — |
| 26 | B29 | 4Cl | H | H | H | H | H | phenyl | — |
| 27 | B29 | 2Cl | H | H | H | H | H | phenyl | — |
| 28 | B29 | 4CH₃ | H | H | H | H | H | phenyl | — |
| 29 | B30c | H | H | H | CH₃ | H | H | phenyl | — |
| 30 | B1a | H | CH₃ | H | H | H | H | phenyl | 148.7° C. |
| 31 | B29 | 5CH₃ | H | H | H | H | H | phenyl | 156.7° C. |
| 32 | B38 | 2OH | H | H | H | H | H | phenyl | 181.6° C. |
| 380 | B3b | H | H | H | H | H | H | phenylethyl | — |
| 381 | B3b | H | H | H | H | H | H | [1-methyl-imidazol-5-yl structure] | — |
| 382 | B11 | H | H | H | H | 2-CH3 | H | phenyl | 158.8° C. |
| 383 | B11 | H | H | H | H | 2-Cl | H | phenyl | 144.8° C. |
| 384 | B3a | H | H | H | H | H | H | 4-trifluoromethoxyphenyl | 130.7° C. |
| 385 | B3a | H | H | H | H | H | H | 2,6-difluorophenyl | 119.7° C. |
| 386 | B3a | H | H | H | H | H | H | 1-methyl-4-pyrazolyl | 194.6° C. |
| 387 | B3a | H | H | H | H | H | H | 3-pyridinyl | 94.4° C. |
| 388 | B3a | H | H | H | H | H | H | 4-pyridinyl | 96.2° C. |
| 389 | B3a | H | H | H | H | H | H | 1,3-benzodioxol-5-yl | 278.3° C. |
| 390 | B3a | H | H | H | H | H | H | 2-methoxy phenyl | 251.2° C. |

TABLE II-continued

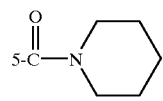

| Co. No. | Ex. No. | R¹ | R² | R³ | R⁴ | R²⁷ | R²⁸ | L | Physical Data |
|---|---|---|---|---|---|---|---|---|---|
| 391 | B3a | H | H | H | H | H | H | 1,3-dimethoxyphenyl | 228.9° C. |
| 392 | B3a | H | H | H | H | H | H | 2-quinolinyl | 209.8° C. |
| 393 | B3a | H | H | H | H | H | H | 3-quinolinyl | 163.6° C. |
| 394 | B3a | H | H | H | H | H | H | 2-pyridinyl | 181.° C.; $\alpha_{20}^D = +5.86$ (c = 11.10 mg/5 ml in DMF) |
| 395 | B3a | H | H | H | H | H | H | 2,5-dimethoxyphenyl | 170.8° C. |
| 396 | B3a | H | H | H | H | H | H | 3,4,5-trimethoxyphenyl | 159.6° C. |
| 397 | B3a | H | H | H | H | H | H | 2,6-dimethoxyphenyl | 136.4° C. |
| 398 | B3a | H | H | H | H | H | H | 2,4-difluorophenyl |  |
| 489 | B33a | H | H | H | H | H | H | 2-pyridinyl | (B); mp. 118° C.; $\alpha_{20}^D = +319.70$ (c = 25.43 mg/5 ml in DMF) |
| 490 | B11 | H | H | H | H | H | H | 2-thienyl |  |
| 423 | B13a | H | H | H | H | H | H | 3,4-dimethoxyphenyl | 241.5° C. |

TABLE III

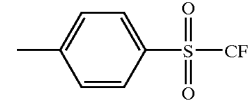

| Co. No. | Ex. No. | R²⁷ | L | Physical Data |
|---|---|---|---|---|
| 33 | B1a | 5-C(=O)-N-piperidine | phenyl | — |
| 34 | B1a | H | 4-methylphenyl-S(=O)₂-CF₃ | — |
| 36 | B1a | H | phenyl | — |
| 37 | B1a | 5Cl | 4-(1-methylethyl)phenyl-Br (CH₃) |  |
| 35 | B3b | 5-CF₃ | 2,4-dichlorophenyl |  |

TABLE IV

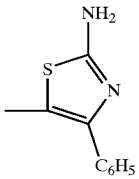

| Co. No. | Ex. No. | R¹ | R⁵ | R⁶ | R²⁷ | R²⁸ | L | Physical Data |
|---|---|---|---|---|---|---|---|---|
| 38 | B1a | H | CH₃ | OH | 5-CH₃ | OH | phenyl | — |
| 39 | B1a | H | CN | CH₃ | 5-F | H | 4F-phenyl | — |
| 40 | B1a | H | CN | H | 3-CH₃ | 5CH₃ | 4Cl-phenyl | — |
| 41 | B1a | H | CN | 4Cl-phenyl | 5-Cl | H | 4Cl-phenyl | — |
| 42 | B1a | H | CN | CH₃ | 2-CH₃ | 5Cl | 4Cl-phenyl | — |
| 43 | B1a | H | H | CH₃ | H | H | 2,4Cl-phenyl | — |
| 44 | B3 | H | H | H | H | H | phenyl | — |
| 45 | B3 | H | CN | CH₃ | H | H | phenyl | — |
| 46 | B1a | H | H | H | 5-phenyl-methoxyoxy | H | 2,4Cl-phenyl | — |
| 47 | B1a | H | H | H | SOCH₃ | H | 4Cl-phenyl | — |
| 48 | B1a | H | CH₃ | (CO)OCH₂CH₃ | H | H | phenyl | — |
| 49 | B1a | H | CN | CH₃ | 5Cl | H | 4Cl-phenyl | — |
| 50 | B13a | H | H | OH | H | H | phenyl | — |
| 51 | B20a | H | OH | CH₃ | H | H | phenyl | — |
| 52 | B13b | H | H | OCH₃ | H | H | phenyl | .HCl (1:1) |
| 53 | B16b | H | H | 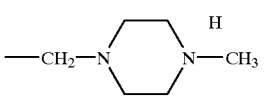 | H | H | phenyl | — |
| 54 | B15 | H | OH | phenyl | H | H | phenyl | — |
| 55 | B4a | H | CN | H | H | H | phenyl | — |
| 56 | B19a | H | H | COOCH₃ | H | H | phenyl | — |
| 57 | B28d | H | H | OH | H | H | phenyl | (S) |
| 58 | B13b | R | H | OCH₃ | H | H | phenyl | — |
| 59 | B13a | 2CH₃ | H | OH | H | H | phenyl | 113.6° C. |
| 60 | B13a | 2OCH₃ | H | OH | H | H | phenyl | 115.9° C. |
| 61 | B13a | 4Cl | H | OH | H | H | phenyl | 146.6° C. |
| 62 | B20a | H | CH₃ | OH | H | H | phenyl | (A1) |
| 63 | B30b | H | CH₃ | CH₂NH₂ | H | H | phenyl | .2HCl.2H₂O |
| 64 | B3 | H | OH | CH₂N(CH₃)₂ | H | H | phenyl | — |
| 65 | B3 | H | OH | 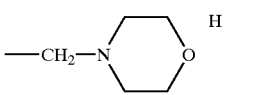 | H | H | phenyl | — |
| 66 | B14 | H | OH | CH(CH₃)₂ | H | H | phenyl | — |
| 67 | B1a | H | OH | 2-pyridinyl methyl | H | H | phenyl | — |
| 68 | B15 | H | OH | 2-pyridinyl | H | H | phenyl | (B) |
| 69 | B21 | H | OH | -C≡CH | H | H | phenyl | [B(R)] + [B(S)] |
| 70 | B1a | H | OH | 2-thiazolyl | H | H | phenyl | — |
| 71 | B1a | H | OH | 1-methyl-2-imidazolyl | H | H | phenyl | — |
| 72 | B3 | H | OH | 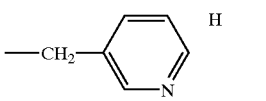 | H | H | phenyl | — |
| 73 | B1a | H | OH |  | H | H | phenyl | — |

TABLE IV-continued

| Co. No. | Ex. No. | R¹ | R⁵ | R⁶ | R²⁷ | R²⁸ | L | Physical Data |
|---|---|---|---|---|---|---|---|---|
| 74 | B1a | H | OH | N-ethyl carbamate of fluorenylmethyl | H | H | phenyl | — |
| 75 | B23c | H | CN | OCONH$_2$ | H | H | phenyl | 187.6° C. |
| 76 | B24b | H | CN | OCH$_3$ | H | H | phenyl | 137.6° C. |
| 77 | B3 | H | OH | 2-pyridinyl | H | H | phenyl | — |
| 78 | B16b | H | H | N-methyl-tetrahydroisoquinolinyl | H | H | phenyl | — |
| 79 | B17b | H | OH | CH$_2$NH$_2$ | H | H | phenyl | — |
| 80 | B3 | H | CN | propyl-morpholinyl | H | H | phenyl | 84° C. |
| 81 | B3 | H | CN | (CH$_2$)$_2$CH$_3$ | H | H | phenyl | 70.9° C. |
| 82 | B3 | H | CN | 2-pyridinyl-methyl | H | H | phenyl | 92.9° C. |
| 83 | B25a | H | CN | O(CO)CH$_3$ | H | H | phenyl | 137.5° C. |
| 84 | B25b | H | CN | N=N$^+$=N | H | H | phenyl | 70.4° C. |
| 85 | B3 | H | OH | C(O)-morpholinyl | H | H | phenyl | 219.8° C. |
| 86 | B3 | H | CN | (CH$_2$)$_2$N(CH$_3$)$_2$ | H | H | phenyl | 103.7° C. |
| 87 | B26 | H | CN | OCH$_2$OCH$_3$ | H | H | phenyl | .HCl |
| 399 | B3a | H | CN | (CH$_2$)$_2$OCH$_3$ | H | H | phenyl | 61.8° C. |
| 400 | B3a | H | OH | COOH | H | H | phenyl | |
| 401 | B3a | H | NH$_2$ | COOCH$_3$ | H | H | phenyl | 66.4° C. |
| 402 | B1a | H | CN | CH$_2$COCH$_3$ | H | H | phenyl | 100.5° C. |
| 403 | B39b | H | OH | CH$_3$ | H | H | phenyl | $\alpha_{20}^D$ = −270.99 (c =5.48 mg/5 ml DMF) |
| 404 | B13b | H | CN | OC$_2$H$_5$ | H | H | phenyl | 81.0° C. |
| 405 | B13b | H | H | cyclopentyloxy | H | H | phenyl | |
| 406 | B19b | H | H | COOH | H | H | phenyl | |
| 407 | B30a | H | H | OH | H | H | 4-pyridinyl | 212° C. |
| 408 | B30a | H | H | OH | H | H | 2,4-difluorophenyl | 189.0° C. |
| 409 | B30a | H | H | OH | H | H | 2-methoxyphenyl | 267.4° C. |
| 410 | B33 | H | H | O-N=C(CH$_3$)CH$_2$CH(CH$_3$)$_2$ oxime | H | H | phenyl | (5S) |
| 411 | B39b | H | CH$_3$ | OH | H | H | phenyl | (A2); $\alpha_{20}^D$ = +258.77 (c = 5.70 mg/5 ml in DMF) |
| 412 | B28c | H | H | OH | H | H | phenyl | [5S(A)]; $\alpha_{20}^D$ = +318.89 (c = 25.15 mg (5 ml in DMF) |

TABLE IV-continued

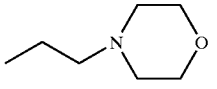

| Co. No. | Ex. No. | R$^1$ | R$^5$ | R$^6$ | R$^{27}$ | R$^{28}$ | L | Physical Data |
|---|---|---|---|---|---|---|---|---|
| 413 | B28a | H | CN | —CH$_2$—O—C(=O)CH$_3$ | H | H | phenyl | 76.5° C. |
| 414 | B28a | H | H | —O—C(=O)CH$_3$ | H | H | phenyl | 139.8° C. |
| 415 | B25a | H | CN | —O—C(=O)phenyl | H | H | phenyl | 103° C. |
| 416 | B13b | H | H | —O—(CH$_2$)$_2$—OCH$_3$ | H | H | phenyl | |
| 417 | B13b | H | H | —O—(CH$_2$)$_3$CH$_3$ | H | H | phenyl | HCl (1:1) |
| 418 | B13b | H | H | —O—CH(CH$_3$)$_2$ | H | H | phenyl | HCl (1:1) |
| 419 | B28b | H | H | =NOH | H | H | phenyl | [B(E)]; 216° C.; $\alpha_{20}^D$ = +259.77 (c = 5.12 mg/ 5 ml in methanol) |
| 420 | B28b | H | H | =NOH | H | H | phenyl | [A(E)]; 217° C.; $\alpha_{20}^D$ = −261.54 (c = 5.20 mg 5 ml in methanol) |
| 421 | B3a | H | H | 1H-tetrazol-5-yl | H | H | phenyl | 165° C. |
| 524 | B34a | H | CN | —O—COOCH$_3$ | H | H | phenyl | — |
| 525 | B28b | H | H | OH | H | H | 2-pyridinyl | (B2), 196° C.; $\alpha_{20}^D$ = −203.96 (c = 24.98/mg 5 ml in methanol) |

TABLE V

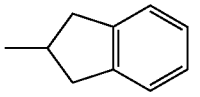

| Co. No. | Ex. No. | R$^6$ | R$^{17}$ | R$^{18}$ | Physical Data |
|---|---|---|---|---|---|
| 88 | B3 | H | H | (CO)CH | — |
| 89 | B16b | H | H | CH$_2$CH$_3$ | — |
| 90 | B16b | H | H | cyclopropyl | — |
| 91 | B16b | H | H | 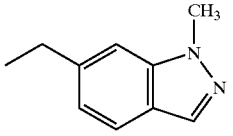 | — |
| 92 | B16b | H | H | phenyl | — |
| 93 | B16b | H | H | 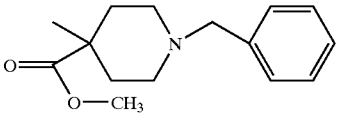 | — |
| 94 | B16b | H | H |  | — |
| 95 | B16b | H | H |  | — |

TABLE V-continued

[Structure: 3-(pyridin-3-yl)-4,5-dihydroisoxazole-5-carboxamide with N-phenyl group bearing CH(R⁶)(phenyl)(NR¹⁷R¹⁸) substituent]

| Co. No. | Ex. No. | R⁶ | R¹⁷ | R¹⁸ | Physical Data |
|---|---|---|---|---|---|
| 96 | B16b | H | H | (methylbenzotriazolyl) | — |
| 97 | B16b | H | H | 4-pyridinylmethyl | — |
| 98 | B16b | H | H | (methyl-phenyl-thiazolyl) | — |
| 99 | B16b | H | H | 2-pyridinyl | — |
| 100 | B16b | H | H | CH(CH₃)₂ | — |
| 101 | B16b | H | H | 1-methyl-5-benzimidazolyl | — |
| 102 | B16b | H | H | 1-methyl-4-piperidinyl | — |
| 103 | B16b | H | H | (1-methyl-4-piperidinyl)methyl | — |
| 104 | B16b | H | H | 1-phenylmethyl-4-piperidinyl | — |
| 105 | B16b | H | H | (4-(diphenylmethyl)-1-propylpiperazinyl) | — |
| 106 | B16b | H | (CH₂)₂OCH₃ | phenyl | — |
| 107 | B16b | H | CH₃ | phenyl | — |
| 108 | B16b | H | CH₃ | 1-methyl-4-piperidinyl | — |
| 109 | B16b | H | CH3 | phenyl | — |
| 110 | B16b | H | H | cyclopropylmethyl | — |
| 111 | B16b | H | H | 1-pyrrolidinylethyl | — |
| 112 | B16b | H | H | (CH₂)₂OCH₂CH₃ | — |
| 113 | B16b | H | H | phenyl | — |
| 114 | B16b | H | H | phenylmethyl | — |
| 115 | B16b | H | H | phenylethyl | — |
| 116 | B16b | H | H | phenylpropyl | — |
| 117 | B16b | H | H | (4-methyl-2-(tosylamino)pyrimidinyl) | — |
| 118 | B16b | H | H | 5-methyl-2-thiazolyl | — |
| 119 | B16b | H | H | (3-methoxy-4-methyl-benzenesulfonamide) | — |
| 120 | B16b | H | CH₂(CO)NH₂ | phenylmethyl | — |
| 121 | B16b | H | CH₃ | (CH₂)₂OCH₃ | — |

TABLE V-continued

[Structure: 3-(pyridin-3-yl)-4,5-dihydroisoxazole-5-carboxamide attached to NH-phenyl-CH(R⁶)(phenyl) with NR¹⁷R¹⁸ substituent]

| Co. No. | Ex. No. | R⁶ | R¹⁷ | R¹⁸ | Physical Data |
|---|---|---|---|---|---|
| 122 | B16b | H | CH₃ | (1,3-dioxolan-2-yl)ethyl | — |
| 123 | B16b | H | CH₃ | —CH₂—C≡CH | — |
| 124 | B16b | H | CH₂CH₃ | phenylmethyl | — |
| 125 | B17a | H | (CO)OC(CH₃)₃ | (CO)OC(CH₃)₃ | — |
| 126 | B17b | H | H | H | — |
| 127 | B18a | H | H | (CO)CH₂Cl | — |
| 128 | B18a | H | H | (CO)C(CH₃)₃ | — |
| 129 | B18a | H | H | phenylcarbonyl | — |
| 130 | B18a | H | H | 4-(trifluoromethyl)phenylcarbonyl | — |
| 131 | B18a | H | H | (CO)OC₂H₅ | — |
| 132 | B18a | H | H | (CO)CH₂(CO)OC₂H₅ | — |
| 133 | B18a | H | H | 1-naphthalenylsulfonyl | — |
| 134 | B18a | H | H | phenylmethylsulfonyl | — |
| 135 | B18a | H | H | (CO)C(CH₃)₂NH(CO)OC(CH₃)₃ | — |
| 136 | B18a | H | H | (CO)CH₂NH(CO)OC(CH₃)₃ | — |
| 137 | B18a | H | H | (CO)C(CH₃)₂NH₂ | — |
| 138 | B18a | H | H | (CO)CH₂NH₂ | — |
| 139 | B18b | H | H | (CO)CH₂NHCH₂CH₃ | — |
| 140 | B18b | H | H | —C(O)CH₂—N(4-methylpiperazin-1-yl) | — |
| 141 | B18b | H | H | —C(O)CH₂—N[4-(pyrimidin-2-yl)piperazin-1-yl] | — |
| 142 | B18b | H | H | 4-morpholinylmethylcarbonyl | — |
| 143 | B18b | H | H | —C(O)CH₂—N(CH₃)(cyclohexyl) | — |
| 144 | B18b | H | H | —C(O)CH₂—N(CH₃)(phenyl) | — |
| 145 | B18b | H | H | —C(O)CH₂—N⁺(CH₃)₂-piperidin-4-yl-NHCH₃ | .Cl⁻ |
| 146 | B18b | H | H | —C(O)CH₂—N(CH₃)-(1-methylpiperidin-4-yl) | — |
| 147 | B18b | H | H | —C(O)CH₂—N⁺(CH₃)-piperidin-4-yl-NH₂ | — |

TABLE V-continued

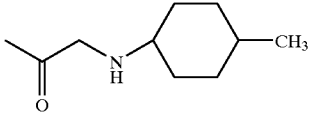

| Co. No. | Ex. No. | R⁶ | R¹⁷ | R¹⁸ | Physical Data |
|---|---|---|---|---|---|
| 148 | B18b | H | H | 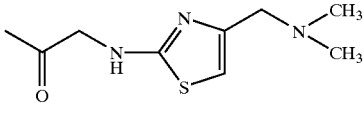 | — |
| 149 | B18b | H | H | 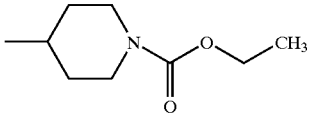 | — |
| 150 | B16b | H | H | 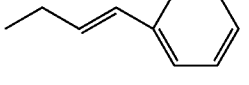 | — |
| 151 | B16b | H | CH₃ | 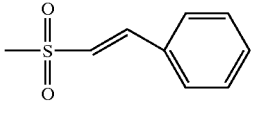 | — |
| 152 | B16b | H | phenyl | phenylmethyl | — |
| 153 | B18a | H | H | 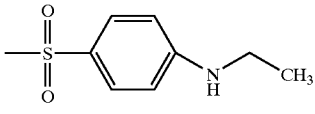 | — |
| 154 | B18a | H | H | 4-fluorophenylsulfonyl | — |
| 155 | B18a | H | H | 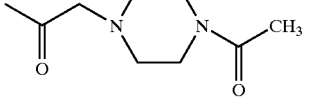 | — |
| 156 | B18a | H | H | (CO)(CH₂)₂CH₃ | — |
| 157 | B18a | H | H | 2-naphtalenylsulfonyl | — |
| 158 | B18a | H | H | 2,6-difluorophenylcarbonyl | — |
| 159 | B16b | H | H | 1H-imidazol-2-ylmethyl | — |
| 160 | B16b | H | H | (1,3-benzodioxole-5-yl)methyl | — |
| 161 | B16b | H | H | 4-chloro-1-naphthalenyl | — |
| 162 | B16b | H | H | 5-methyl-3-isoxazolyl | — |
| 163 | B16b | H | CH₃ | CH₂(CO)NH₂ | — |
| 164 | B16b | H | H | 2-pyrimidinyl | — |
| 165 | B18b | H | H | 3-oxopropen-3-yl | — |
| 166 | B18b | H | H | phenylmethylcarbonyl | — |
| 167 | B18b | H | H | phenoxycarbonyl | — |
| 168 | B18b | H | H | 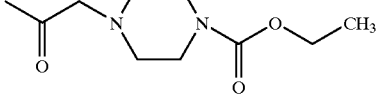 | — |
| 169 | B18b | H | H |  | — |

TABLE V-continued

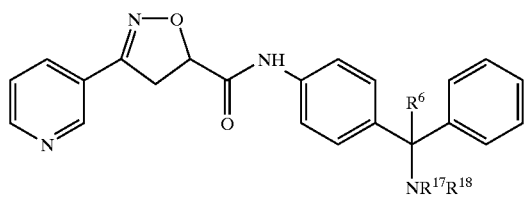

| Co. No. | Ex. No. | R⁶ | R¹⁷ | R¹⁸ | Physical Data |
|---|---|---|---|---|---|
| 170 | B18b | H | H | ![structure: acetonyl-NH-pyrazole] | — |
| 171 | B16b | H | H | 2,5-diethoxyphenyl | — |
| 172 | B16b | H | H | 5-ethoxy-2-methylphenyl | — |
| 173 | B16b | H | H | 4-(1-piperidinyl)phenyl | — |
| 174 | B16b | H | H | 2-(methylcarbonylamino)phenyl | — |
| 175 | B16b | H | H | 2,3-dimethylphenyl | — |
| 176 | B16b | H | H | 3,4-difluorophenyl | — |
| 177 | B16b | H | H | 4-methoxyphenyl | — |
| 178 | B16b | H | H | 3-hydroxyphenyl | — |
| 179 | B16b | H | H | 2-cyanomethyl | — |
| 180 | B16b | H | H | 6-benzothiazolyl | — |
| 181 | B16b | H | H | 3-hydroxy-4-methylphenyl | — |
| 182 | B16b | H | H | 4-chloro-3-methylphenyl | — |
| 183 | B16b | H | H | 4-carboxy-3-hydroxyphenyl | — |
| 184 | B16b | H | H | ![structure: 2-cyano-4-methyl-phenyl ether with 3,4-dichlorophenyl] | — |
| 185 | B16b | H | H | 2,4-difluorophenyl | — |
| 186 | B16b | H | H | 4-methylphenyl | — |
| 187 | B16b | H | H | 3,5-dichlorophenyl | — |
| 188 | B16b | H | H | 3-methoxyphenyl | — |
| 189 | B16b | H | H | 4-fluorophenyl | — |
| 190 | B16b | H | H | 3-methylphenyl | — |
| 191 | B16b | H | H | 3,5-dichloro-4-(methylcarboxyl-amino)phenyl | — |
| 192 | B16b | H | H | 2-aminocarbonylphenyl | — |
| 193 | B16b | H | H | 2-methoxyphenyl | — |
| 194 | B16b | H | H | 2,5-dimethylphenyl | — |
| 195 | B16b | H | H | 3,4-dichlorophenyl | — |
| 196 | B16b | H | H | 2,5-dichlorophenyl | — |
| 197 | B16b | H | H | 3-(trifluoromethyl)phenyl | — |
| 198 | B16b | H | H | 2-methylphenyl | — |
| 199 | B16b | H | H | 2,4-dimethylphenyl | — |
| 200 | B16b | H | H | 4-chloro-2-iodophenyl | — |
| 201 | B16b | H | H | 2,3-dichlorophenyl | — |
| 202 | B16b | H | H | 2-(methoxyoxycarbonyl)phenyl | — |
| 203 | B16b | H | H | 2-hydroxyphenyl | — |
| 204 | B16b | H | H | 2,4-dimethoxyphenyl | — |
| 205 | B17c | H | H | H | [5S-(A)] |
| 206 | B17c | H | H | H | [5S-(B)] |
| 207 | B16b | CN | H | 2-pyridinyl | — |
| 208 | B16b | H | H | 4-chlorophenyl | — |
| 209 | B16b | H | H | 2-chloro-6-methylphenyl | — |
| 210 | B16b | H | H | 3,5-dimethylphenyl | — |
| 211 | B16b | H | H | 2,6-dichlorophenyl | — |
| 212 | B16b | H | H | 3-chloro-4-methylphenyl | — |
| 213 | B16b | H | H | 2-bromo-4,6-difluorophenyl | — |
| 214 | B16b | H | H | 3-fluorophenyl | — |
| 215 | B16b | H | H | 5-chloro-2-methoxyphenyl | — |
| 216 | B16b | H | H | 3-chlorophenyl | — |

TABLE V-continued

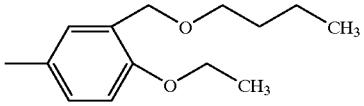

| Co. No. | Ex. No. | R⁶ | R¹⁷ | R¹⁸ | Physical Data |
|---|---|---|---|---|---|
| 217 | B16b | H | H | | — |
| 218 | B16b | H | H | 2-bromo-4-(trifluoromethyl)phenyl | — |
| 219 | B16b | H | H | 2-chloro-6-methylphenyl | (5B) |

TABLE VI

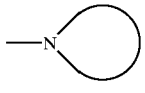

| Co. No | Ex. No. | R⁶ | —N(ring) | Physical Data |
|---|---|---|---|---|
| 220 | B16b | H | (2-imino-1-pyridinyl) | |
| 221 | B16b | | 4-morpholinyl | — |
| 222 | B16b | H | 4-hydroxy-1-piperidinyl | — |
| 223 | B16b | H | (4-(4-oxo-4H-chromen-2-yl)-1-piperidinyl) | — |
| 224 | B16b | H | (4-(2-(methoxycarbonylamino)-1,4,5,6-tetrahydropyrimidin-5-yl)-1-piperidinyl) | — |
| 225 | B16b | H | 4-methyl-1-piperazinyl | — |
| 226 | B16b | H | 4-butyl-1-piperazinyl | — |
| 227 | B16b | H | 4-phenyl-1-piperazinyl | — |
| 228 | B16b | H | 4-(phenylpropyl)-1-piperazinyl | — |
| 229 | B16b | H | 4-(ethoxycarbonyl)-1-piperidinyl | — |

TABLE VI-continued
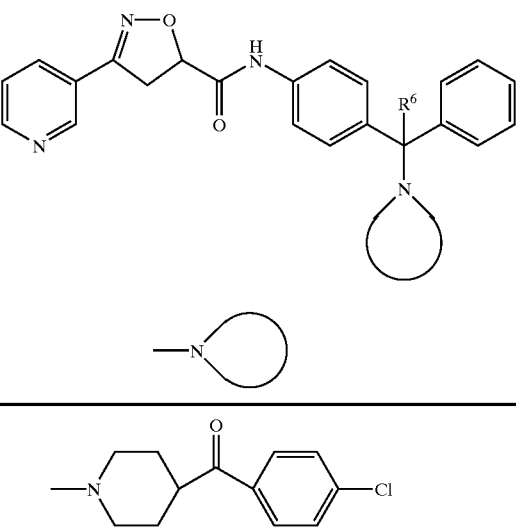
| Co. No | Ex. No. | R[6] | | Physical Data |
|---|---|---|---|---|
| 230 | B16b | H | 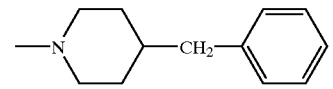 | — |
| 231 | B16b | H | 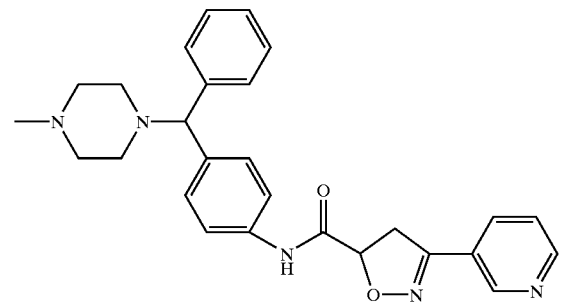 | — |
| 232 | B16b | H | 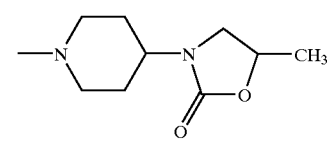 | — |
| 233 | B16b | H | 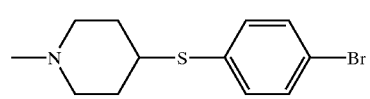 | — |
| 234 | B16b | H | 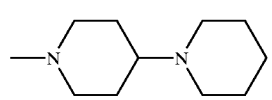 | — |
| 235 | B16b | H | 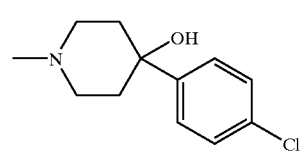 | — |
| 236 | B16b | H | 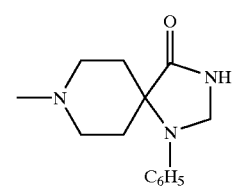 | — |
| 237 | B16b | H | | — |

TABLE VI-continued
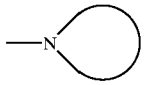
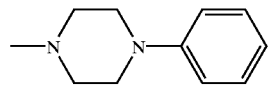
| Co. No | Ex. No | R⁶ | | Physical Data |
|---|---|---|---|---|
| 238 | B16b | H | 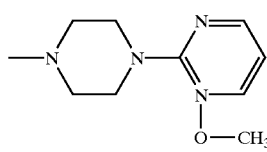 | — |
| 239 | B16b | H | 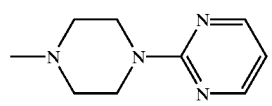 | — |
| 240 | B16b | H | 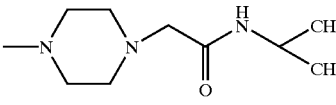 | — |
| 241 | B16b | H | 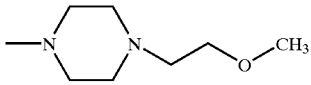 | — |
| 242 | B16b | H | 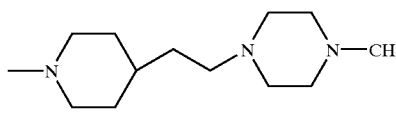 | — |
| 243 | B16b | H | 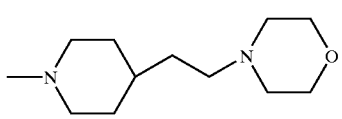 | — |
| 244 | B16b | H | 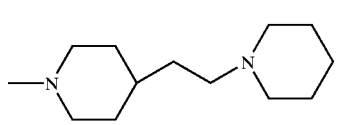 | — |
| 245 | B16b | H | | — |
| 246 | B16b | H | 4-ethoxycarbonyl-1-piperazinyl | — |
| 247 | B16b | H | 4-methylcarbonyl-1-piperazinyl | — |
| 248 | B16b | H | 4-phenylmethyl-1-piperazinyl | — |
| 249 | B16b | H | 5-amino-1-pyrazolyl | — |
| 250 | B16b | H | 3,6-dihydro-4-hydroxy-1(2H)-pyridinyl | — |
| 251 | B16b | H | 4-(hydroxymethyl)-1-piperidinyl | 166–168° C.; 2-butenedioic acid salt (1:1) |
| 252 | B16b | H | 4-(aminocarbonyl)-1-piperidinyl | — |

TABLE VI-continued

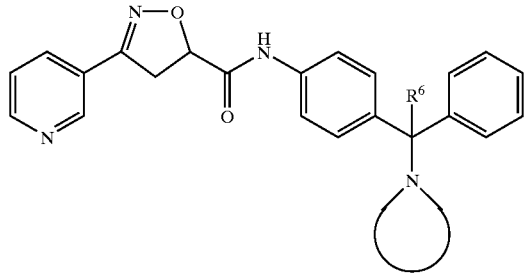

| Co. No | Ex. No | R⁶ | | Physical Data |
|---|---|---|---|---|
| 253 | B16b | 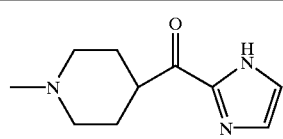 | | — |
| 254 | B16b | H | 4-phenyl-1-piperidinyl | — |
| 422 | B16b | H | 4-(hydroxymethyl)-1-piperidinyl | |

TABLE VII

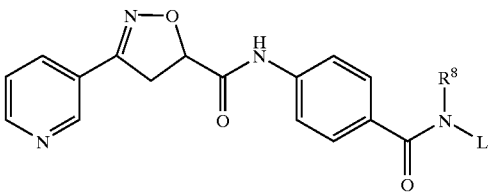

| Co. No. | Ex. No. | R⁸ | L | Stereochemistry; melting point; salt |
|---|---|---|---|---|
| 255 | B12 | H | phenyl | — |
| 256 | B12 | CH₃ | phenyl | — |
| 257 | B12 | H | phenylmethyl | — |
| 258 | B12 | H | phenylethyl | — |
| 259 | B12 | H | 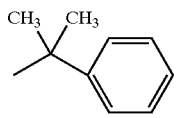 | — |
| 260 | B12 | H | 4-pyridinyl | — |
| 261 | B12 | CH₃ | 1-methyl-4-piperidinyl | — |
| 262 | B12 | H | 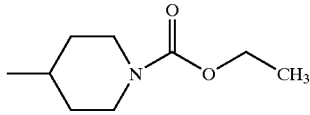 | — |
| 263 | B12 | H | 3-pyridinyl | — |
| 264 | B12 | H | 2-thiazolyl | .2 HCl.H₂O |
| 265 | B12 | H | 2-indanylphenyl | — |
| 266 | B12 | H | 1-naphthalenyl | — |
| 267 | B12 | H | 2-pyrimidinyl | — |
| 268 | B12 | H | 2-furanylethyl | — |
| 269 | B12 | H | (2-bromophenyl)methyl | — |
| 270 | B12 | H | (4-fluorophenyl)methyl | — |
| 271 | B31 | H | 2-pyridinylmethyl | — |
| 272 | B12 | H | (3-methoxyphenyl)methyl | — |
| 273 | B12 | H | (4-methylphenyl)methyl | — |

TABLE VII-continued

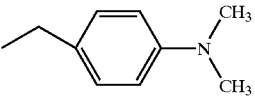

| Co. No. | Ex. No. | R⁸ | L | Stereochemistry; melting point; salt |
|---|---|---|---|---|
| 274 | B12 | H | (2,4-dimethoxyphenyl)methyl | — |
| 275 | B12 | H | 2-pyridinyl | — |
| 276 | B12 | H | 1-methyl-2-benzimidazolyl | — |
| 277 | B12 | H | (1H-imidazole-2-yl)ethyl | — |
| 278 | B12 | H | (4-aminophenyl)methyl | — |
| 279 | B12 | H | (2,6-difluorophenyl)methyl | — |
| 280 | B12 | H | (4-pyridinyl)methyl | — |
| 281 | B12 | H | (3,4,5-dimethoxyphenyl)methyl | — |
| 282 | B12 | H | (1-naphthalenyl)methyl | — |
| 283 | B12 | CH₃ | phenylmethyl | — |
| 284 | B12 | H | 4-pyridinylmethyl | — |
| 285 | B12 | H | (2-methoxyphenyl)methyl | — |
| 286 | B12 | H | 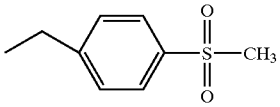 | — |
| 287 | B12 | H | 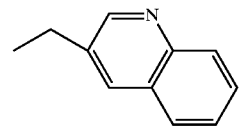 | — |
| 288 | B12 | H | [(3-trifluoromethyl)phenyl]methyl | — |
| 289 | B12 | H | (2-thiophenyl)methyl | — |
| 290 | B12 | H | (4-methoxyphenyl)methyl | — |
| 291 | B12 | H | 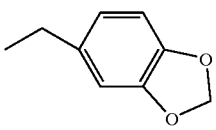 | — |
| 292 | B12 | H | (2-amino-6-fluorophenyl)methyl | — |
| 293 | B12 | H | (3-chloro-4-fluorophenyl)methyl | — |
| 294 | B12 | H | [3,5-(trifluoromethyl)phenyl]methyl | — |
| 295 | B12 | H |  | — |
| 296 | B12 | H | (2,4-dichlorophenyl)ethyl | — |
| 297 | B12 | H | (3,4-dichlorophenyl)methyl | — |
| 298 | B12 | H | (3,4-dimethoxyphenyl)ethyl | — |
| 299 | B12 | H | [4-(aminosulfonyl)phenyl]methyl | — |
| 300 | B12 | H | [4-(aminomethyl)phenyl]methyl | — |
| 424 | B3b | H | (4-carboxyphenyl)methyl | — |
| 425 | B12 | H | [4-aminocarbonyl)phenyl]methyl | — |
| 426 | B12 | H | [4-(dimethylaminocarbonyl)phenyl]methyl | — |
| 427 | B12 | H | [4-(methylaminocarbonyl)phenyl]methyl | — |

TABLE VIII

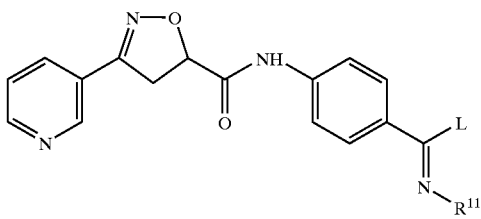

| Co. No. | Ex. No. | $R^{11}$ | L | Physical Data |
|---|---|---|---|---|
| 301 | B2 | OH | phenyl | (E) |
| 302 | B2 | (CH₃)N(cyclohexyl)C(=O)CH₂CH₃ | phenyl | (E + Z) |
| 303 | B3 | —OCH₃ | phenyl | — |
| 428 | B32 | OH | 4-pyridinyl | mp. 154.4° C. |
| 429 | B32 | OH | 1,3-benzodioxole-5-yl | mp. 226.1° C. |
| 430 | B32 | OH | 3-(trifluoromethoxy)phenyl | mp. 222.7° C. |
| 431 | B32 | OH | 2,6-difluorophenyl | mp. 124.3° C. |
| 432 | B32 | OH | 3-quinolinyl | mp. 209.9° C. |
| 434 | B32 | OH | 2-methoxyphenyl | mp. 224.0° C. |
| 435 | B32 | OH | 2,4-difluorophenyl | mp. 178.7° C. |
| 436 | B32 | OH | 3,4,5-trimethoxyphenyl | mp. 206.7° C. |
| 437 | B32 | OH | 3,4-dimethoxyphenyl | mp. 199.0° C. |
| 438 | B32 | OH | 2,4-dimethoxyphenyl | mp. 194.6° C. |
| 439 | B32 | OH | 2-pyridinyl | mp. 186.2° C. |
| 440 | B32 | OH | 2,5-dimethoxyphenyl | mp. 183.8° C. |
| 441 | B3 | —O—CH₂—O—(CH₂)₂—OCH₃ | phenyl | (E) |

TABLE IX

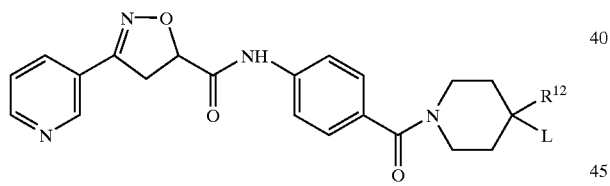

| Co. No. | Ex. No. | $R^{12}$ | L |
|---|---|---|---|
| 304 | B12 | OH | phenylmethyl |
| 305 | B12 | H | phenylmethyl |
| 306 | B12 | H | phenylcarbonyl |
| 307 | B12 | H | phenyl |
| 308 | B12 | H | 1-piperidinyl |

TABLE X

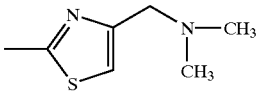

| Co. No. | Ex. No. | X₂ | R¹³ | R¹⁴ | R¹⁵ | R²⁷ | L | Physical Data |
|---|---|---|---|---|---|---|---|---|
| 309 | B1a | O | H | H | H | 3-Cl | 4-chlorophenyl | — |
| 310 | B1a | O | H | H | H | 5-Cl | 2,4-dichlorophenyl | — |
| 311 | B1a | O | CH₃ | H | H | 5-Cl | 4-fluorophenyl | — |
| 312 | B3 | O | H | H | H | H | phenyl | — |
| 313 | B4b | S | H | H | H | H | phenyl | — |
| 314 | B19d | O | H | H | 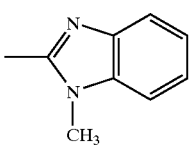 | H | phenyl | |
| 315 | B19d | O | H | H | 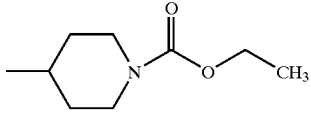 | H | phenyl | — |
| 316 | B19d | O | H | H | CH(CH₃)₂ | H | phenyl | — |
| 317 | B19d | O | H | H | (CH₂)₂OC₂H₅ | H | phenyl | — |
| 318 | B19d | O | H | H | 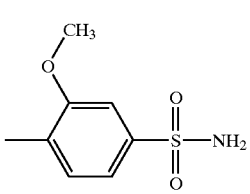 | H | phenyl | |
| 319 | B19d | O | H | H | 1H-imidazol-2-yl)-methyl | H | phenyl | |
| 320 | B19d | O | H | H | 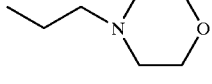 | H | phenyl | |
| 321 | B19d | O | H | H | phenyl | H | phenyl | — |
| 322 | B19d | O | H | H | phenylmethyl | H | phenyl | — |
| 323 | B7 | O | CH₃ | H | H | H | phenyl | 109.6° C. |
| 324 | B19d | O | CH₃ | H | OCH₃ | H | phenyl | — |
| 325 | B19d | O | H | H | 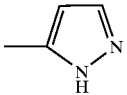 | H | phenyl | |
| 326 | B19d | O | H | H |  | H | phenyl | |
| 327 | B19d | O | H | CH₃ | (CH₂)₂OCH₃ | H | phenyl | — |
| 328 | B19d | O | H | CH₃ | phenyl | H | phenyl | — |
| 329 | B3 | O | OH | CH₃ | CH₃ | H | phenyl | 121° C. |
| 330 | B3 | O | OH | H | H | H | phenyl | 151.8° C. |
| 442 | B3b | O | OCH₃ | H | H | H | phenyl | 108.6° C. |
| 443 | B38 | O | OH | H | —(CH₂)₂—OH | H | phenyl | 80.7° C.; H₂O (1:1) |

TABLE XI

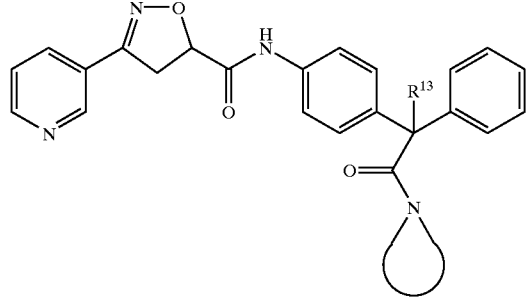

| Co. No. | Ex. No. | [N-ring] | R13 | Physical Data |
|---|---|---|---|---|
| 331 | B19d | 4-(tert-butoxycarbonyl)-1-piperazinyl | H | |
| 332 | B19d | 4-(aminocarbonyl)-1-piperidinyl | H | |
| 333 | B19d | 4-morpholinyl | H | |
| 334 | B19d | 4-hydroxy-1-piperidinyl | H | |
| 335 | B19d | [1,4'-bipiperidin]-1'-yl | H | |
| 336 | B19d | 4-methyl-1-piperazinyl | H | |
| 337 | B19d | 4-(2-pyrimidinyl)-1-piperazinyl | H | |
| 337 | B19d | 4-phenyl-1-piperazinyl | H | |
| 339 | B19d | 4-(phenylmethyl)-1-piperazinyl | H | |
| 340 | B19d | 4-(ethoxycarbonyl)-1-piperazinyl | H | |
| 341 | B19d | 4-(1H-imidazol-2-ylcarbonyl)-1-piperidinyl | H | |
| 342 | B3 | 4-methyl-1-piperazinyl | OH | |
| 444 | B3a | 4-morpholinyl | NH2 | mp. 140.2° C. |

TABLE XII

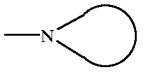

| Co. No. | Ex. No. | n | B | Physical Data |
|---|---|---|---|---|
| 343 | B6 | 1 | N-methylacetamide | 175.3° C. |
| 344 | B1a | 1 | N-methylacetamide | 153.7° C. |
| 445 | B8 | 0 | 3-methyl-1,2,4-oxadiazol-5-yl | — |
| 446 | B8 | 0 | 3-methyl-1,2,4-oxadiazol-5-yl | 99.1° C. |
| 447 | B9 | 0 | 5-methyl-1,3,4-oxadiazol-2-yl | 138.9° C. |

TABLE XIII

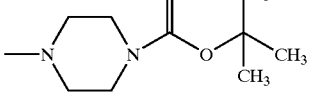

| Co. No. | Ex. No. | A | —R29 | Physical Data |
|---|---|---|---|---|
| 345 | B3 | 2-pyridinyl | =O | — |
| 346 | B13a | 2-pyridinyl | —OH | — |
| 347 | B3 | 4-pyridinyl | =O | — |
| 348 | B13a | 4-pyridinyl | —OH | — |
| 349 | B29 | 5-pyrimidinyl | =O | — |
| 350 | B13a | 5-pyrimidinyl | —OH | 162.6° C. |
| 351 | B29 | 2-pyrazinyl | =O | 156.0° C. |
| 352 | B1a | phenyl | =O | — |
| 353 | B13a | phenyl | —OH | 113.7° C. |
| 354 | B1a | 3-(cyclopentyloxy)-4-methoxyphenyl | =O | — |

TABLE XIII-continued

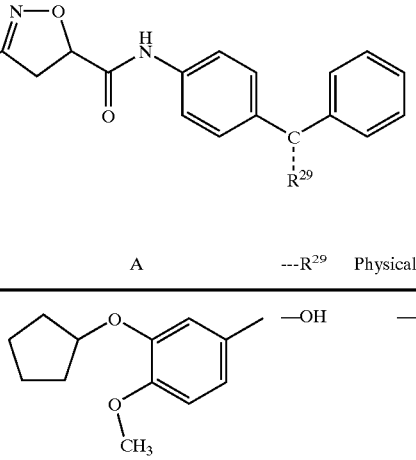

| Co. No. | Ex. No. | A | ---R²⁹ | Physical Data |
|---|---|---|---|---|
| 355 | B13a | 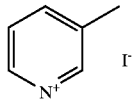 | —OH | — |
| 356 | B1a | 3-nitrophenyl | =O | — |
| 357 | B13a | 3-nitrophenyl | —OH | 136.4° C. |
| 358 | B1a | 3-trifluoromethylphenyl | =O | 154.1° C. |
| 359 | B13a | 3-trifluoromethylphenyl | —OH | 162.4° C. |
| 360 | B29 | 3-chlorophenyl | =O | 214.2° C. |
| 361 | B13a | 3-chlorophenyl | —OH | 151.4° C. |
| 362 | B29 | 4-cyanophenyl | =O | 188.9° C. |
| 363 | B29 | 2-chloro-5-methoxyphenyl | =O | — |
| 364 | B29 | 3-methoxyphenyl | =O | 159.5° C. |
| 365 | B29 | 3-methylphenyl | =O | 169.1° C. |
| 366 | B29 | 4-trifluoromethylphenyl | =O | 173.4° C. |
| 367 | B1a | 3-methylphenyl | —OH | 153.3° C. |

TABLE XIII-continued

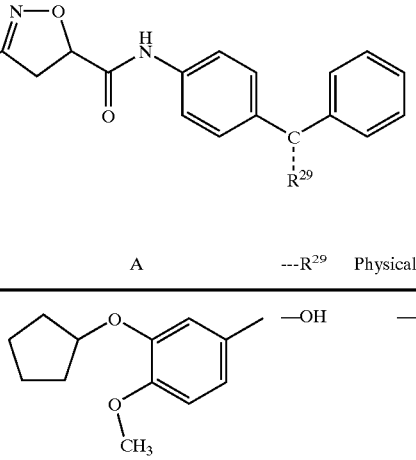

| Co. No. | Ex. No. | A | ---R²⁹ | Physical Data |
|---|---|---|---|---|
| 368 | B29 | 3,5-bis(dimethylethyl)-4-hydroxyphenyl | =O | 162.9° C. |
| 369 | B29 | 3,4-dichlorophenyl | =O | 173.2° C. |
| 370 | B13a | 3-cyanophenyl | —OH | 123.5° C. |
| 448 | B27 | 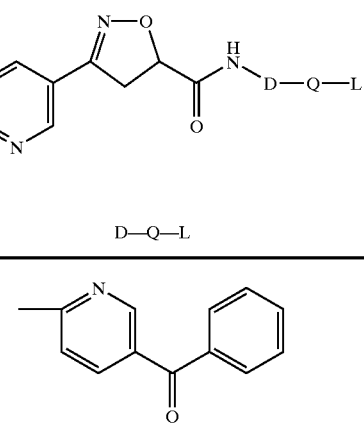 I⁻ | =O | — |
| 449 | B45 | 1-oxido-3-pyridinyl | =O | 233.5° C. |
| 450 | B13a | 3-quinolinyl | —OH | 177.0° C. |

TABLE XIV

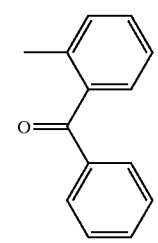

| Co. No. | Ex. No. | D—Q—L | Physical Data |
|---|---|---|---|
| 371 | B3 | | — |
| 372 | B3 | | — |

TABLE XIV-continued
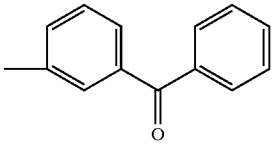
| Co. No. | Ex. No. | D—Q—L | Physical Data |
|---|---|---|---|
| 373 | B3 | 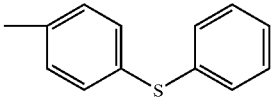 | — |
| 374 | B1a | 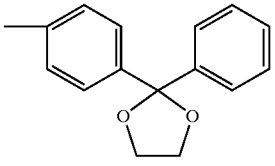 | — |
| 375 | B22 | 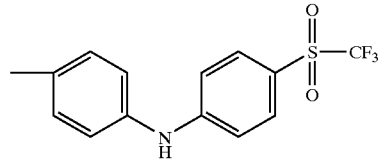 | (B) |
| 376 | B1a | 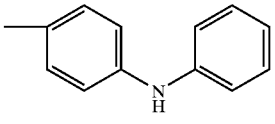 | — |
| 377 | B3 | 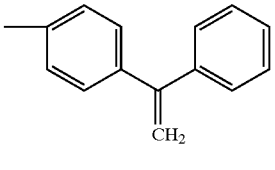 | — |
| 378 | B20b | 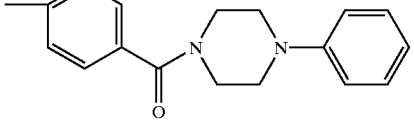 | — |
| 379 | B12 | 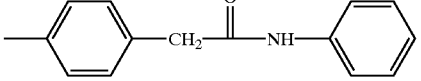 | — |
| 451 | B3b | 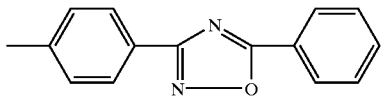 | |
| 452 | B48 | | |

TABLE XIV-continued
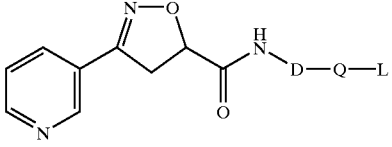
| Co. No. | Ex. No. | D—Q—L | Physical Data |
|---|---|---|---|
| 453 | B48 | 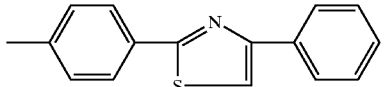 | |
| 454 | B48 | 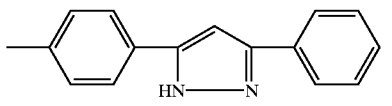 | |
| 455 | B48 | 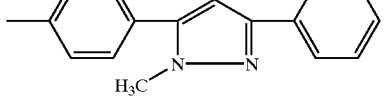 | |
| 456 | B48 | 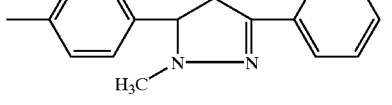 | |
| 457 | B48 | 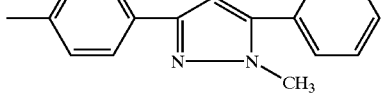 | |
| 458 | B48 | 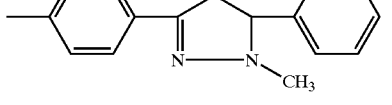 | |
| 459 | B48 | 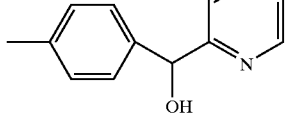 | |
| 460 | B19 | 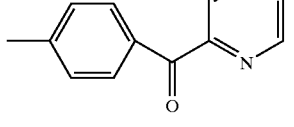 | 193.1° C. |
| 461 | B28b | 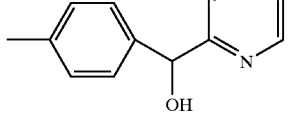 | (A), 177° C.; $\alpha_{20}^D = -346.03°$ (c = 24.81 mg/5 ml) |
| 462 | B13a |  | (5B) |

TABLE XIV-continued

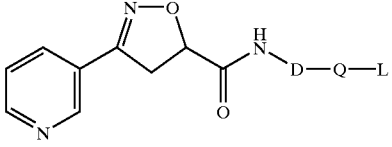

| Co. No. | Ex. No. | D—Q—L | Physical Data |
|---|---|---|---|
| 463 | B47 | (4-fluoro-1H-indazol-3-yl)-p-tolyl | |
| 464 | B47 | (1H-benzimidazol-1-yl)-p-tolyl | |
| 465 | B48 | (6-fluoro-1-methyl-1H-indazol-3-yl)-p-tolyl | |
| 466 | B48 | (6-fluoro-1,2-benzisoxazol-3-yl)-p-tolyl | |
| 467 | B47 | (2-methyl-1H-benzimidazol-1-yl)-p-tolyl | |

TABLE XV

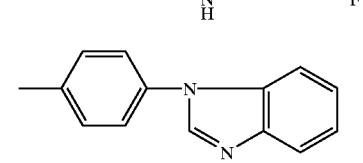

| Co. No. | Ex. No. | L | Physical Data |
|---|---|---|---|
| 468 | B46 | 2,6-difluorophenyl | (E) |
| 469 | B46 | 1,3-benzodioxol-5-yl | (E) |
| 470 | B46 | 2-(2-propenyloxy)phenyl | (E) |
| 471 | B46 | 2-(trifluoromethyl)phenyl | (E) |
| 472 | B46 | 2-thienyl | (E) |
| 473 | B46 | 2-fluorophenyl | (E) |
| 474 | B46 | 4-(dimethylamino)phenyl | (E) |
| 475 | B46 | 2-methylphenyl | (E) |
| 476 | B46 | 2-chloro-6-fluorophenyl | (E) |
| 477 | B46 | 2-methoxyphenyl | (E) |
| 478 | B46 | phenyl | (E) |
| 479 | B46 | 2,3-dimethyl-4-methoxyphenyl | (E) |

TABLE XVI

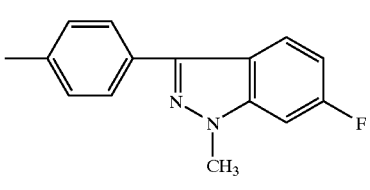

| Co. No. | Ex. No. | X | Q—L | Physical Data |
|---|---|---|---|---|
| 480 | B43 | CH | 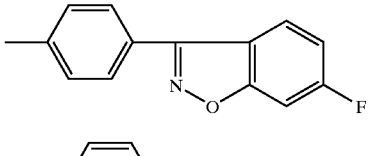 | |
| 481 | B43 | CH | 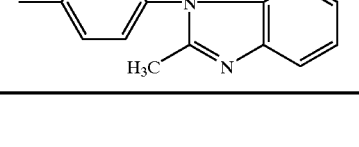 | |

TABLE XVI-continued

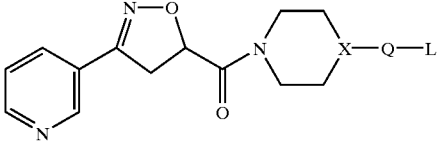

| Co. No. | Ex. No. | X | Q—L | Physical Data |
|---|---|---|---|---|
| 482 | B43 | CH | 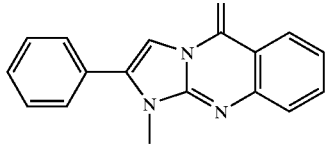 | |
| 483 | B43 | CH | 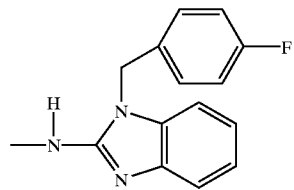 | |
| 484 | B39 | CH | diphenylcyanomethyl | |
| 485 | B19 | CH | 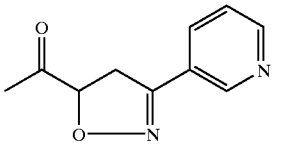 | |
| 486 | B41 | N | 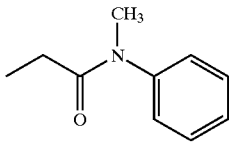 | 228.0° C. |
| 487 | B19 | N |  | |
| 488 | B19 | N | diphenylmethyl | |

C. PHARMACOLOGICAL EXAMPLE

EXAMPLE C.1

In Vitro Inhibition of T Cell Blast Formation in Human Blood

Human whole blood blast formation

Peripheral blood from healthy consenting donors is collected into sterile plastic syringes containing pyrogen-free heparin at a final concentration of 12.5 U/ml. Blood samples are three-fold diluted in RPMI 1640 medium supplemented with 2 mM L-glutamine, 100 U/ml penicillin and 100 mg/ml streptomycin, and 300 ml fractions are distributed into 24-well multidish plates. Blood samples are preincubated (60 minutes at 37° C.) in a humidified 6% $CO_2$-atmosphere with 100 ml of drug solvent (1% DMSO in RPMI 1640) or with 100 ml of appropriate concentrations of test compounds before being stimulated by the addition of 100 ml of PHA at a final concentration of 2 mg/ml. Cells are collected after a 72 hours culture period at 37° C., supernatant is removed by centrifugation and red blood cells are lysed by a hypotonic buffer. The remaining white blood cells are collected in PBS containing propidium iodide. The blast formation is analyzed using a benchtop flow cytometer (Cytoron, Ortho) equipped with an argon-ion laser.

Table XV lists the percentage inhibition of T cell blast formation (column "% Inhibition") at a certain test dose (column "Test Dose") for the preferred embodiments of the present invention. When multiple measurements were performed, a mean value was calculated for the percentage inhibition of T cell blast formation.

TABLE XV

| Co. No. | Test Dose | % Inhibition |
|---|---|---|
| 1 | $1 \times 10^{-6}$ | 81 |
| 3 | $1 \times 10^{-6}$ | 76 |
| 8 | $1 \times 10^{-6}$ | 55 |
| 9 | $1 \times 10^{-6}$ | 71 |
| 10 | $1 \times 10^{-6}$ | 75 |
| 12 | $1 \times 10^{-6}$ | 83 |
| 13 | $1 \times 10^{-6}$ | 78 |
| 14 | $1 \times 10^{-6}$ | 78 |
| 15 | $1 \times 10^{-6}$ | 85 |
| 16 | $1 \times 10^{-6}$ | 76 |
| 17 | $3 \times 10^{-7}$ | 53 |
| 20 | $1 \times 10^{-6}$ | 73 |
| 36 | $1 \times 10^{-5}$ | 85 |
| 39 | $1 \times 10^{-6}$ | 67 |
| 44 | $1 \times 10^{-6}$ | 84 |
| 45 | $1 \times 10^{-6}$ | 78 |
| 50 | $1 \times 10^{-6}$ | 91 |
| 51 | $1 \times 10^{-6}$ | 92 |
| 52 | $1 \times 10^{-6}$ | 89 |
| 53 | $1 \times 10^{-6}$ | 39 |
| 54 | $1 \times 10^{-6}$ | 75 |
| 55 | $1 \times 10^{-6}$ | 94 |
| 56 | $1 \times 10^{-5}$ | 87 |
| 57 | $1 \times 10^{-6}$ | 92 |
| 68 | $1 \times 10^{-6}$ | 61 |
| 69 | $1 \times 10^{-6}$ | 73 |
| 73 | $3 \times 10^{-7}$ | 67 |
| 75 | $3 \times 10^{-7}$ | 67 |
| 78 | $1 \times 10^{-6}$ | 51 |
| 83 | $1 \times 10^{-6}$ | 68 |
| 84 | $1 \times 10^{-6}$ | 53 |
| 88 | $3 \times 10^{-7}$ | 35 |
| 90 | $1 \times 10^{-6}$ | 33 |
| 91 | $1 \times 10^{-6}$ | 36 |
| 174 | $1 \times 10^{-6}$ | 42 |
| 175 | $1 \times 10^{-6}$ | 42 |
| 191 | $1 \times 10^{-6}$ | 62 |
| 192 | $1 \times 10^{-6}$ | 172 |
| 203 | $1 \times 10^{-6}$ | 62 |
| 205 | $1 \times 10^{-6}$ | 73 |
| 206 | $1 \times 10^{-6}$ | 66 |
| 214 | $1 \times 10^{-6}$ | 62 |
| 216 | $1 \times 10^{-6}$ | 70 |
| 218 | $3 \times 10^{-7}$ | 33 |
| 220 | $1 \times 10^{-6}$ | 59 |
| 221 | $1 \times 10^{-6}$ | 63 |
| 235 | $3 \times 10^{-7}$ | 64 |
| 243 | $3 \times 10^{-7}$ | 48 |
| 257 | $1 \times 10^{-6}$ | 63 |
| 258 | $1 \times 10^{-6}$ | 59 |
| 259 | $1 \times 10^{-6}$ | 51 |
| 263 | $1 \times 10^{-6}$ | 59 |
| 266 | $1 \times 10^{-5}$ | 85 |
| 268 | $1 \times 10^{-6}$ | 58 |
| 269 | $1 \times 10^{-6}$ | 67 |
| 270 | $1 \times 10^{-6}$ | 71 |
| 271 | $1 \times 10^{-5}$ | 71 |
| 272 | $1 \times 10^{-6}$ | 67 |
| 273 | $1 \times 10^{-6}$ | 62 |
| 274 | $1 \times 10^{-6}$ | 71 |
| 279 | $3 \times 10^{-7}$ | 74 |

TABLE XV-continued

| Co. No. | Test Dose | % Inhibition |
|---|---|---|
| 281 | $3 \times 10^{-7}$ | 74 |
| 285 | $1 \times 10^{-6}$ | 72 |
| 286 | $3 \times 10^{-7}$ | 49 |
| 288 | $1 \times 10^{-6}$ | 53 |
| 289 | $3 \times 10^{-7}$ | 64 |
| 290 | $1 \times 10^{-6}$ | 67 |
| 291 | $1 \times 10^{-6}$ | 78 |
| 94 | $1 \times 10^{-6}$ | 44 |
| 96 | $1 \times 10^{-6}$ | 39 |
| 97 | $1 \times 10^{-6}$ | 58 |
| 99 | $1 \times 10^{-6}$ | 83 |
| 100 | $1 \times 10^{-6}$ | 35 |
| 101 | $1 \times 10^{-6}$ | 70 |
| 102 | $1 \times 10^{-6}$ | 66 |
| 103 | $1 \times 10^{-6}$ | 82 |
| 104 | $1 \times 10^{-6}$ | 60 |
| 113 | $3 \times 10^{-7}$ | 37 |
| 119 | $1 \times 10^{-6}$ | 54 |
| 122 | $3 \times 10^{-7}$ | 36 |
| 131 | $1 \times 10^{-6}$ | 95 |
| 146 | $1 \times 10^{-6}$ | 95 |
| 156 | $1 \times 10^{-6}$ | 56 |
| 158 | $3 \times 10^{-7}$ | 64 |
| 162 | $3 \times 10^{-7}$ | 46 |
| 163 | $3 \times 10^{-7}$ | 56 |
| 166 | $1 \times 10^{-6}$ | 66 |
| 172 | $1 \times 10^{-6}$ | 35 |
| 414 | $1 \times 10^{-6}$ | 77 |
| 510 | $1 \times 10^{-6}$ | 76 |
| 491 | $1 \times 10^{-7}$ | 70 |
| 490 | $1 \times 10^{-6}$ | 58 |
| 442 | $1 \times 10^{-6}$ | 75 |
| 427 | $1 \times 10^{-6}$ | 80 |
| 426 | $1 \times 10^{-6}$ | 82 |
| 417 | $1 \times 10^{-6}$ | 42 |
| 416 | $1 \times 10^{-6}$ | 87 |
| 415 | $1 \times 10^{-6}$ | 65 |
| 418 | $1 \times 10^{-6}$ | 75 |
| 505 | $1 \times 10^{-6}$ | 73 |
| 497 | $1 \times 10^{-6}$ | 81 |
| 524 | $1 \times 10^{-6}$ | 81 |
| 506 | $1 \times 10^{-6}$ | 88 |
| 292 | $3 \times 10^{-7}$ | 40 |
| 295 | $3 \times 10^{-7}$ | 35 |
| 301 | $1 \times 10^{-6}$ | 80 |
| 302 | $1 \times 10^{-6}$ | 69 |
| 303 | $1 \times 10^{-6}$ | 78 |
| 304 | $3 \times 10^{-7}$ | 36 |
| 307 | $9 \times 10^{-7}$ | 41 |
| 309 | $1 \times 10^{-6}$ | 92 |
| 310 | $3 \times 10^{-7}$ | 64 |
| 312 | $1 \times 10^{-6}$ | 93 |
| 313 | $1 \times 10^{-6}$ | 88 |
| 314 | $3 \times 10^{-7}$ | 58 |
| 316 | $3 \times 10^{-7}$ | 81 |
| 325 | $3 \times 10^{-7}$ | 43 |
| 374 | $1 \times 10^{-5}$ | 85 |
| 376 | $3 \times 10^{-7}$ | 69 |
| 377 | $1 \times 10^{-6}$ | 85 |
| 378 | $1 \times 10^{-6}$ | 75 |
| 379 | $3 \times 10^{-7}$ | 51 |
| 371 | $1 \times 10^{-6}$ | 62 |
| 412 | $3 \times 10^{-7}$ | 79 |
| 411 | $1 \times 10^{-6}$ | 77 |
| 504 | $3 \times 10^{-7}$ | 75 |
| 380 | $1 \times 10^{-6}$ | 67 |
| 409 | $3 \times 10^{-7}$ | 88 |
| 508 | $3 \times 10^{-7}$ | 70 |
| 408 | $3 \times 10^{-7}$ | 71 |
| 507 | $3 \times 10^{-7}$ | 58 |
| 410 | $3 \times 10^{-7}$ | 39 |
| 509 | $3 \times 10^{-7}$ | 68 |
| 454 | $3 \times 10^{-7}$ | 59 |
| 451 | $3 \times 10^{-7}$ | 80 |
| 386 | $3 \times 10^{-7}$ | 38 |
| 385 | $3 \times 10^{-7}$ | 69 |
| 384 | $3 \times 10^{-7}$ | 68 |
| 413 | $1 \times 10^{-6}$ | 85 |
| 426 | $3 \times 10^{-7}$ | 65 |
| 387 | $3 \times 10^{-7}$ | 78 |
| 388 | $1 \times 10^{-7}$ | 74 |
| 390 | $1 \times 10^{-6}$ | 85 |
| 437 | $3 \times 10^{-7}$ | 75 |
| 391 | $1 \times 10^{-6}$ | 85 |
| 503 | $1 \times 10^{-6}$ | 89 |
| 394 | $1 \times 10^{-6}$ | 84 |
| 398 | $1 \times 10^{-6}$ | 87 |
| 435 | $1 \times 10^{-7}$ | 81 |
| 434 | $1 \times 10^{-7}$ | 83 |
| 395 | $1 \times 10^{-6}$ | 77 |
| 428 | $1 \times 10^{-7}$ | 57 |
| 440 | $1 \times 10^{-7}$ | 77 |
| 439 | $1 \times 10^{-6}$ | 79 |
| 396 | $1 \times 10^{-6}$ | 65 |
| 438 | $1 \times 10^{-7}$ | 82 |
| 420 | $1 \times 10^{-6}$ | 39 |
| 419 | $1 \times 10^{-6}$ | 86 |
| 436 | $3 \times 10^{-7}$ | 78 |
| 389 | $3 \times 10^{-7}$ | 59 |
| 397 | $1 \times 10^{-6}$ | 82 |
| 429 | $1 \times 10^{-6}$ | 86 |
| 392 | $1 \times 10^{-6}$ | 80 |
| 393 | $1 \times 10^{-6}$ | 69 |
| 407 | $3 \times 10^{-7}$ | 63 |
| 525 | $1 \times 10^{-6}$ | 74 |
| 430 | $3 \times 10^{-7}$ | 67 |
| 431 | $3 \times 10^{-7}$ | 71 |
| 489 | $1 \times 10^{-7}$ | 80 |
| 464 | $1 \times 10^{-6}$ | 85 |
| 478 | $3 \times 10^{-7}$ | 70 |
| 467 | $1 \times 10^{-6}$ | 82 |
| 466 | $1 \times 10^{-5}$ | 82 |
| 465 | $1 \times 10^{-5}$ | 83 |
| 522 | $1 \times 10^{-5}$ | 85 |
| 463 | $3 \times 10^{-7}$ | 33 |
| 520 | $1 \times 10^{-6}$ | 77 |
| 477 | $3 \times 10^{-7}$ | 63 |
| 476 | $3 \times 10^{-7}$ | 67 |
| 475 | $3 \times 10^{-7}$ | 56 |
| 473 | $3 \times 10^{-7}$ | 72 |
| 457 | $3 \times 10^{-7}$ | 67 |
| 432 | $1 \times 10^{-6}$ | 65 |
| 471 | $3 \times 10^{-7}$ | 54 |
| 469 | $3 \times 10^{-7}$ | 65 |
| 468 | $3 \times 10^{-7}$ | 61 |
| 521 | $3 \times 10^{-7}$ | 64 |
| 470 | $1 \times 10^{-6}$ | 87 |
| 523 | $1 \times 10^{-6}$ | 80 |
| 479 | $1 \times 10^{-6}$ | 85 |
| 459 | $1 \times 10^{-6}$ | 77 |
| 453 | $1 \times 10^{-6}$ | 61 |
| 452 | $1 \times 10^{-6}$ | 79 |

D. COMPOSITION EXAMPLES

The following formulations exemplify typical pharmaceutical compositions suitable for systemic or topical administration to animal and human subjects in accordance with the present invention.

"Active ingredient" (A.I.) as used throughout these examples relates to a compound of formula (I) or a pharmaceutically acceptable addition salt thereof.

EXAMPLE D.1

Film-Coated Tablets

Preparation of tablet core

A mixture of A.I. (100 g), lactose (570 g) and starch (200 g) was mixed well and thereafter humidified with a solution of sodium dodecyl sulfate (5 g) and polyvinylpyrrolidone (10 g) in about 200 ml of water. The wet powder mixture was sieved, dried and sieved again. Then there was added microcrystalline cellulose (100 g) and hydrogenated vegetable oil (15 g). The whole was mixed well and compressed into tablets, giving 10.000 tablets, each comprising 10 mg of the active ingredient.

Coating

To a solution of methyl cellulose (10 g) in denaturated ethanol (75 ml) there was added a solution of ethyl cellulose (5 g) in $CH_2Cl_2$ (150 ml). Then there were added $CH_2Cl_2$ (75 ml) and 1,2,3-propanetriol (2.5 ml). Polyethylene glycol (10 g) was molten and dissolved in dichloromethane (75 ml). The latter solution was added to the former and then there were added magnesium octadecanoate (2.5 g), polyvinylpyrrolidone (5 g) and concentrated color suspension (30 ml) and the whole was homogenated. The tablet cores were coated with the thus obtained mixture in a coating apparatus.

EXAMPLE D.2

2% Topical Cream

To a solution of hydroxypropyl β-cyclodextrin (200 mg) in purified water is added A.I. (20 mg) while stirring. Hydrochloric acid is added until complete dissolution and next sodium hydroxide is added until pH 6.0. While stirring, glycerol (50 mg) and polysorbate 60 (35 mg) are added and the mixture is heated to 70° C. The resulting mixture is added to a mixture of mineral oil (100 mg), stearyl alcohol (20 mg), cetyl alcohol (20 mg), glycerol monostearate (20 mg) and sorbate 60 (15 mg) having a temperature of 70° C. while mixing slowly. After cooling down to below 25° C., the rest of the purified water q.s. ad 1 g is added and the mixture is mixed to homogenous.

What is claimed is:

1. A compound of formula

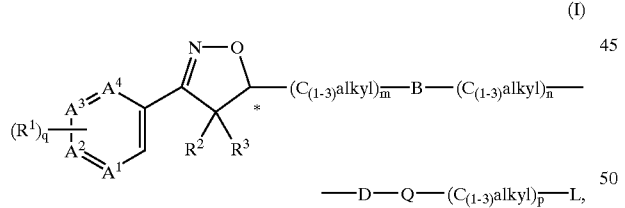

(I)

wherein m, n and p are each independently 0 or 1 and q is 0, 1, 2, 3, 4 or 5;

* indicates an asymmetric carbon atom which can be R or S;

—$A^1$═$A^2$—$A^3$═$A^4$— is a bivalent radical of formula

—N═CH—CH═CH— (a-1)

—CH═N—CH═CH— (a-2)

—CH═CH—CH═N— (a-3)

—CH═CH—N═N— (a-4)

—N═CH—N═CH— (a-5)

—N═CH—CH═N— (a-6);

B is a bivalent radical of formula

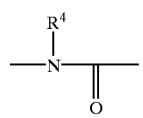 (b-1)

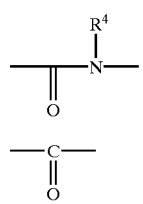 (b-2)

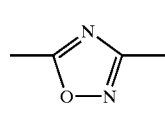 (b-3)

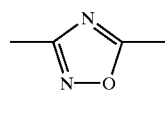 (b-4)

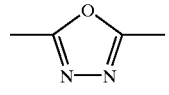 (b-5)

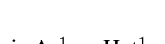 (b-6)

D is $Ar^1$ or $Het^1$;

Q is a direct covalent bond or a bivalent radical of formula

 (c-1)

 (c-2)

(c-3)

 (c-4)

 (c-5)

 (c-6)

 (c-7)

 (c-8)

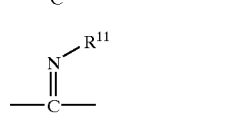 (c-9)

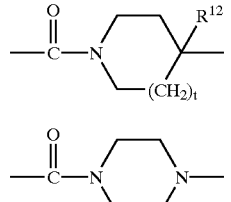

-continued

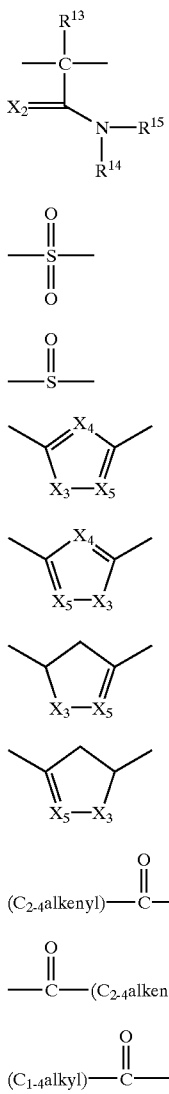

wherein $X_1$ and $X_2$ are each independently S or O, t is 0, 1 or 2;

$X_3$ is independently S, O or $NR^{26}$; $X_4$ and $X_5$ are each independently N or CH, L is $Ar^1$ or $Het^1$;

$R^1$ is selected from hydrogen, halo, hydroxy, $C_{(1-6)}$alkyl, $C_{(2-6)}$alkenyl, $C_{(2-6)}$alkynyl, $C_{(3-6)}$cycloalkyl, $C_{(3-6)}$cycloalkenyl, $C_{(1-6)}$alkyloxy, $C_{(3-6)}$cycloalkyl$C_{(1-6)}$alkyl, $C_{(3-6)}$cycloalkyloxy, halo$C_{(1-6)}$alkyl, cyano, guanidine, nitro and $NR^{17}R^{18}$; p1 $R^2$ and $R^3$ are each independently selected from hydrogen, halo, $C_{(1-6)}$alkyloxy and $C_{(1-6)}$alkyl where the alkyl moiety may be optionally substituted by one or more hydroxy;

$R^4$ is selected from hydrogen, $C_{(1-6)}$alkyl, $C_{(2-6)}$alkenyl, $C_{(2-6)}$alkynyl, $C_{(3-6)}$cycloalkyl and $C_{(3-6)}$cycloalkenyl;

$R^5$, $R^6$, $R^9$ and $R^{10}$ are each independently selected from hydrogen, hydroxy, halo, $C_{(1-6)}$alkyl, $C_{(2-6)}$alkenyl, $C_{(2-6)}$alkynyl, $C_{(3-6)}$cycloalkyl, $C_{(3-6)}$cycloalkenyl, $C_{(1-6)}$alkyloxy, cyano, $(C=O)R^{25}$, $(C=O)OR^{16}$, $(SO_2)R^{16}$, aminocarbonyloxy, amino$C_{(1-6)}$alkyl, $NR^{17}R^{18}$, $N_3$, $Ar^1$ and $Het^1$;

or $R^5$ and $R^6$ or $R^9$ and $R^{10}$ together with the carbon atom to which they are attached, form a $Het^1$ or a $C_{(2-14)}$ carbocyclic radical optionally substituted by 1, 2 or 3 substituents independently selected from halo, hydroxy, $C_{(1-6)}$alkyl, $C_{(2-6)}$alkenyl, $C_{(2-6)}$alkynyl, $C_{(3-6)}$cycloalkyl, $C_{(3-6)}$cycloalkenyl, $C_{(1-6)}$alkyloxy, cyano, (=O), (=NH), $(C=O)R^{22}$, $(SO_2)R^{22}$, $NH(C=O)R^{22}$, $NR^{23}R^{24}$, $C_{(6-14)}$aryl, $C_{(6-14)}$arylthio, $C_{(6-14)}$aryloxy and heterocycle selected from the group consisting of indanyl, pyridinyl, tetrahydropyridinyl isothiazolyl, pyrrolyl, triazolylphenyl, piperidinyl, thiazolyl, piperazinyl, isoxazolyl, pyrazolyl, morpholinyl, imidazolyl, oxadiazolyl, dioxolanyl, pyrimidinyl, dihydropyrimidinyl, oxazolidinyl, benzimidazolyl, benzothiazolyl, benzodioxolanyl, benzopyridinyl, benzopyranyl, furanyl, thionyl, triazospirodecanyl, isoquinolinyl and tetrazolyl;

$R^7$ and $R^8$ are each independently selected from hydrogen, hydroxy, $C_{(1-6)}$alkyl, $C_{(2-6)}$alkenyl, $C_{(2-6)}$alkynyl, $C_{(3-6)}$cycloalkyl, $C_{(3-6)}$cycloalkenyl, hydroxy$C_{(1-6)}$alkyl and $C_{(1-6)}$alkyloxy;

$R^{11}$ is selected from hydrogen, hydroxy and $C_{(1-6)}$alkyloxy;

$R^{12}$ is selected from hydrogen and hydroxy;

$R^{13}$ is selected from hydrogen, hydroxy, halo, $C_{(1-6)}$alkyl, $C_{(2-6)}$alkenyl, $C_{(2-6)}$alkynyl, $C_{(3-6)}$cycloalkyl, $C_{(3-6)}$cycloalkenyl, $C_{(1-6)}$alkyloxy, aminocarbonyloxy, amino$C_{(1-6)}$alkyl, $NR^{17}R^{18}$, $N_3$, $Ar^1$ and $Het^1$;

$R^{14}$ and $R^{15}$ are each independently selected from hydrogen, $C_{(1-6)}$alkyl, $C_{(2-6)}$alkenyl, $C_{(2-6)}$alkynyl, $C_{(3-6)}$cycloalkyl, $C_{(3-6)}$cycloalkenyl, $C_{(1-6)}$alkyloxy, $C_{(6-14)}$aryl$C_{(1-6)}$alkyl, $(C=O)R^{16}$, $(C=O)OR^{16}$, $(C=S)R^{16}$, $(SO_2)R^{16}$, $Ar^1$ and $Het^1$;

or $R^{14}$ and $R^{15}$ together with the N atom to which they are attached, form a heterocycle selected from the group consisting of indanyl, pyridinyl, tetrahydropyridinyl isothiazolyl, pyrrolyl, triazolylphenyl, piperidinyl, thiazolyl, piperazinyl, isoxazolyl, pyrazolyl, morpholinyl, imidazolyl, oxadiazolyl, dioxolanyl, pyrimidinyl, dihydropyrimidinyl, oxazolidinyl, benzimidazolyl, benzothiazolyl, benzodioxolanyl, benzopyridinyl, benzopyranyl, furanyl, thionyl, triazospirodecanyl, isoquinolinyl and tetrazolyl optionally substituted by 1, 2 or 3 substituents independently selected from halo, hydroxy, $C_{(1-6)}$alkyl, $C_{(2-6)}$alkenyl, $C_{(2-6)}$alkynyl, $C_{(3-6)}$cycloalkyl, $C_{(3-6)}$cycloalkenyl and $C_{(1-6)}$alkyloxy, $C_{(6-14)}$arylthio, $C_{(6-14)}$aryloxy, cyano, $(C=O)R^{16}$, $(C=O)OR^{16}$, $(SO_2)R^{16}$, $NR^{17}R^{18}$, $Ar^1$ and $Het^1$;

$R^{16}$ is selected from hydrogen, hydroxy, $C_{(1-6)}$alkyl, $C_{(2-6)}$alkenyl, $C_{(2-6)}$alkynyl, $C_{(3-6)}$cycloalkyl, $C_{(3-6)}$cycloalkenyl, $C_{(1-6)}$alkyloxy, $NR^{17}R^{18}$, $C_{(6-14)}$aryloxy, $Ar^1$ or $Het^1$;

$R^{17}$ and $R^{18}$ are each independently selected from hydrogen, hydroxy, $C_{(1-6)}$alkyl, $C_{(2-6)}$alkenyl, $C_{(2-6)}$alkynyl, $C_{(3-6)}$cycloalkyl, $C_{(3-6)}$cycloalkenyl, $C_{(1-6)}$alkyloxy, $(C=O)R^{19}$, $(SO_2)R^{19}$, $Ar^1$ and $Het^1$;

or $R^{17}$ and $R^{18}$ together with the N atom to which they are attached, form a heterocycle selected from the group consisting of indanyl, pyridinyl, tetrahydropyridinyl isothiazolyl, pyrrolyl, triazolylphenyl, piperidinyl, thiazolyl, piperazinyl, isoxazolyl, pyrazolyl, morpholinyl, imidazolyl, oxadiazolyl, dioxolanyl, pyrimidinyl, dihydropyrimidinyl, oxazolidinyl, benzimidazolyl, benzothiazolyl, benzodioxolanyl, benzopyridinyl, benzopyranyl, furanyl, thionyl, triazospirodecanyl, isoquinolinyl and tetrazolyl optionally substituted by 1, 2 or 3 substituents independently selected from hydroxy, $C_{(1-6)}$alkyl, $C_{(2-6)}$alkenyl, $C_{(2-6)}$alkynyl, $C_{(3-6)}$cycloalkyl, $C_{(3-6)}$cycloalkenyl, $C_{(1-6)}$alkyloxy, $NR^{20}R^{21}$, $(C=O)R^{19}$, $(=NH)$, $S—Ar^1$, $Ar^1$ and $Het^1$;

$R^{19}$ is selected from $C_{(1-6)}$alkyl, $C_{(2-6)}$alkenyl, $C_{(2-6)}$alkynyl, $C_{(3-6)}$cycloalkyl, $C_{(3-6)}$cycloalkenyl, $C_{(1-6)}$alkyloxy, phenyloxy, $NR^{20}R^{21}$, $Ar^1$ and $Het^1$;

$R^{20}$ is selected from hydrogen, $C_{(1-6)}$alkyl, $C_{(2-6)}$alkenyl, $C_{(2-6)}$alkynyl, $C_{(3-6)}$cycloalkyl, $C_{(3-6)}$cycloalkenyl, $NH(C=O)R^{22}$ and $C_{(1-6)}$alkyloxy;

$R^{21}$ is selected from hydrogen, $C_{(1-6)}$alkyl, $C_{(2-6)}$alkenyl, $C_{(2-6)}$alkynyl, $C_{(3-6)}$cycloalkyl, $C_{(3-6)}$cycloalkenyl, $C_{(1-6)}$alkyloxy, $C_{(1-6)}$alkyloxycarbonyl, $Ar^1$ and $Het^1$;

$Ar^1$ is a $C_{(6-14)}$aryl (or $C_{(6-14)}$arylidene when D is $Ar^1$) optionally substituted by one or more substituents independently selected from halo, hydroxy, $C_{(1-6)}$alkyl, $C_{(2-6)}$alkenyl, $C_{(2-6)}$alkynyl, $C_{(3-6)}$cycloalkyl, $C_{(3-6)}$cycloalkenyl, $C_{(1-6)}$alkyloxy, cyano, $(=O)$, $(=NH)$, $(C=O)R^{22}$, $(SO_2)R^{22}$, $NH(C=O)R^{22}$, $NR^{23}R^{24}$, $C_{(6-14)}$aryl, $C_{(6-14)}$arylthio, $C_{(6-14)}$aryloxy and heterocycle selected from the group consisting of indanyl, pyridinyl, tetrahydropyridinyl, isothiazolyl, pyrrolyl, triazolylphenyl, piperidinyl, thiazolyl, piperazinyl, isoxazolyl, pyrazolyl, morpholinyl, imidazolyl, oxadiazolyl, dioxolanyl, pyrimidinyl, dihydropyrimidinyl, oxazolidinyl, benzimidazolyl, benzothiazolyl, benzodioxolanyl, benzopyridinyl, benzopyranyl, furanyl, thionyl, triazospirodecanyl, isoquinolinyl and tetrazolyl;

$Het^1$ is a heterocycle selected from the group consisting of indanyl, pyridinyl, tetrahydropyridinyl isothiazolyl, pyrrolyl, triazolylphenyl, piperidinyl, thiazolyl, piperazinyl, isoxazolyl, pyrazolyl, morpholinyl, imidazolyl, oxadiazolyl, dioxolanyl, pyrimidinyl, dihydropyrimidinyl, oxazolidinyl, benzimidazolyl, benzothiazolyl, benzodioxolanyl, benzopyridinyl, benzopyranyl, furanyl, thionyl, triazospirodecanyl, isoquinolinyl and tetrazolyl (or heterocyclidene selected from the group consisting of a bivalent radical of indanyl, pyridinyl, tetrahydropyridinyl isothiazolyl, pyrrolyl, triazolylphenyl, piperidinyl, thiazolyl, piperazinyl, isoxazolyl, pyrazolyl, morpholinyl, imidazolyl, oxadiazolyl, dioxolanyl, pyrimidinyl, dihydropyrimidinyl, oxazolidinyl, benzimidazolyl, benzothiazolyl, benzodioxolanyl, benzopyridinyl, benzopyranyl, furanyl, thionyl, triazospirodecanyl, isoquinolinyl and tetrazolyl when D is $Het^1$) optionally substituted by one or more substituents independently selected from halo, hydroxy, $C_{(1-6)}$alkyl, $C_{(2-6)}$alkenyl, $C_{(2-6)}$alkynyl, $C_{(3-6)}$cycloalkyl, $C_{(3-6)}$cycloalkenyl, $C_{(1-6)}$alkyloxy, cyano, $(=O)$, $(=NH)$, $(C=O)R^{22}$, $(SO_2)R^{22}$, $NH(C=O)R^{22}$, $NR^{23}R^{24}$, $C_{(6-14)}$aryl, $C_{(6-14)}$arylthio, $C_{(6-14)}$aryloxy and heterocycle selected from the group consisting of indanyl, pyridinyl, tetrahydropyridinyl isothiazolyl, pyrrolyl, triazolylphenyl, piperidinyl, thiazolyl, piperazinyl, isoxazolyl, pyrazolyl, morpholinyl, imidazolyl, oxadiazolyl, dioxolanyl, pyrimidinyl, dihydropyrimidinyl, oxazolidinyl, benzimidazolyl, benzothiazolyl, benzodioxolanyl, benzopyridinyl, benzopyranyl, furanyl, thionyl, triazospirodecanyl, isoquinolinyl and tetrazolyl;

$R^{22}$ is selected from hydrogen, hydroxy, $C_{(1-6)}$alkyl, $C_{(1-6)}$alkyloxy, halo$C_{(1-6)}$alkyl, $NR^{23}R^{24}$ and

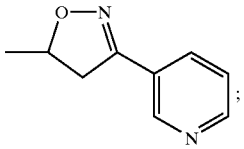

;

$R^{23}$ and $R^{24}$ are each independently selected from hydrogen, $C_{(1-6)}$alkyl and

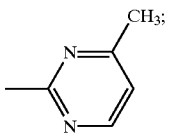

;

$R^{25}$ is selected from hydrogen, hydroxy, $C_{(1-6)}$alkyl, $C_{(2-6)}$alkenyl, $C_{(2-6)}$alkynyl, $C_{(3-6)}$cycloalkyl, $C_{(3-6)}$cycloalkenyl, $C_{(1-6)}$alkyloxy, $C_{(6-14)}$aryloxy, $Ar^1$ and $Het^1$;

$R^{26}$ is selected from hydrogen, $C_{(1-6)}$alkyl and phenyl;

or a N-oxide, addition salt, quaternary amine or stereochemically isomeric form thereof.

2. A compound according to claim 1 wherein Q is a bivalent radical of formula (c-1), (c-2), (c-3), (c-4), (c-5), (c-6), (c-7), (c-8), (c-9), (c-10), (c-11) or (c-12).

3. A compound according to claim 1 wherein B is a group of formula (b-2).

4. A compound according to claim 1 wherein $—A^1=A^2—A^3=A^4—$ is a radical of formula (a-1).

5. A compound according to claim 1 wherein groups $R^1$, $R^2$, $R^3$ and $R^4$ are hydrogen.

6. A compound according to claim 1 wherein m and n are 0 and p is 0 or 1.

7. A compound according to claim 1 wherein D is a phenylidene moiety, optionally substituted with halo or pyridinylidene.

8. A compound according to claim 1 wherein L is a phenyl, optionally substituted with one or more substituents independently selected from halo, $C_{(1-3)}$alkyloxy, $C_{(1-3)}$alkyl (wherein the alkyl moiety may be optionally substituted with one or more halo substituents), $NR^{23}R^{24}$ (wherein $R^{23}$ and $R^{24}$ are independently selected from hydrogen and $C_{(1-3)}$alkyl), $(C=O)R^{22}$ (wherein $R^{22}$ is $NR^{23}R^{24}$ (wherein $R^{23}$ and $R^{24}$ are independently selected from hydrogen and $C_{(1-3)}$alkyl)), $(SO_2)R^{22}$ (wherein $R^{22}$ is $C_{(1-6)}$alkyl or halo $C_{(1-6)}$alkyl) and $NH(C=O)R^{22}$ (wherein $R^{22}$ is

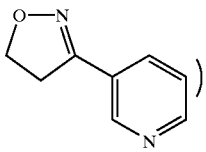

)

or naphtalenyl or $Het^1$.

9. A compound according to claim 1 wherein Q is a bivalent radical of formula (c-1), (c-2), (c-3), (c-4), (c-5), (c-6), (c-7), (c-8), (c-9) or (c-10).

10. A compound according to claim 1 wherein
B is a group of formula (b-2);

—A$^1$=A$^2$—A$^3$=A$^4$— is a radical of formula (a-1);
groups R$^1$, R$^2$, R$^3$ and R$^4$ are hydrogen;
m and n are 0 and p is 0 or 1;
D is phenylidene (wherein the phenylidene moiety may be optionally substituted with halo);
L is phenyl (wherein the phenyl moiety may be optionally substituted with one or more substituents independently selected from halo, C$_{(1-3)}$alkyloxy, C$_{(1-3)}$alkyl, (SO$_2$)R$^{22}$ (wherein R$^{22}$ is C$_{(1-3)}$alkyl (wherein the alkyl moiety may be optionally substituted with one or more halo), R$^{22}$ is trifluoromethyl), NH(C=O)R$^{22}$ (wherein R$^{22}$ is

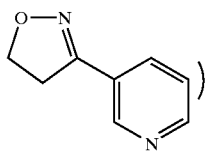

)

and Het$^1$;

Q is a bivalent radical of formula (c-1), (c-3), (c-4), (c-5), (c-7) or (c-10).

11. A compound according to claim 1 selected from
N-(4-benzoylphenyl)-4,5-dihydro-3-(3-pyridinyl)-5-isoxazolecarboxamide;
(B)-N-(4-benzoylphenyl)-4,5-dihydro-3-(3-pyridinyl)-5-isoxazolecarboxamide;
(E)-4,5-dihydro-N-[4-[(hydroxyimino)phenylmethyl]phenyl]-3-(3-pyridinyl)-5-isoxazolecarboxamide;
4,5-dihydro-N-[4-(hydroxyphenylmethyl)phenyl]-3-(3-pyridinyl)-5-isoxazolecarboxamide;
[5S(B)]-4,5-dihydro-N-[4-(hydroxyphenylmethyl)phenyl]-3-(3-pyridinyl)-5-isoxazolecarboxamide;
4,5-dihydro-N-[4-(phenylmethyl)phenyl]-3-(3-pyridinyl)-5-isoxazolecarboxamide;
N-[4-(aminophenylmethyl)phenyl]-4,5-dihydro-3-(3-pyridinyl)-5-isoxazolecarboxamide;
[5S(A)]-N-[4-(aminophenylmethyl)phenyl]-4,5-dihydro-3-(3-pyridinyl)-5-isoxazolecarboxamide;
N-[4-(cyanophenylmethyl)phenyl]-4,5-dihydro-3-(3-pyridinyl)-5-isoxazolecarboxamide;
4,5-dihydro-N-[(4-(4-methoxybenzoyl)phenyl]-3-(3-pyridinyl)-5-isoxazolecarboxamide;
4,5-dihydro-N-[((4-methoxyphenylmethyl)phenyl]-3-(3-pyridinyl)-5-isoxazolecarboxamide;
4,5-dihydro-3-(3-pyridinyl)-N-[4-[[2-pyridinylmethyl)amino]carbonyl]phenyl]-5-isoxazolecarboxamide
(±)-[cyano-[4-[[[4,5-dihydro-3-(3-pyridinyl)-5-isoxazolyl]carbonyl]amino]-phenyl]phenylmethyl]acetate
(±)-(E)-4,5-dihydro-N-[4-(1-oxo-3-phenyl-2-propenyl)phenyl]-3-(3-pyridinyl)-5-isoxazolecarboxamide
(±)-N-[4-(3,4-dimethoxybenzoyl)phenyl]-4,5-dihydro-3-(3-pyridinyl)-5-isoxazolecarboxamide;
(±)-N-[4-(2,4-difluorobenzoyl)phenyl]-4,5-dihydro-3-(3-pyridinyl)-5-isoxazolecarboxamide;
(±)-N-[4-(4,5-dihydro-1-methyl-3-phenyl-1H-pyrazol-5-yl)phenyl-4,5-dihydro-3-(3-pyridinyl)-5-isoxazolecarboxamide;
(±)-N-[4-[(2,4-difluorophenyl)hydroxymethyl]phenyl]-4,5-dihydro-3-(3-pyridinyl)-5-isoxazolecarboxamide;
(B)-4,5-dihydro-3-(3-pyridinyl)-N-[4-(2-pyridinylcarbonyl)phenyl]-5-isoxazolecarboxamide;
(B2)-4,5-dihydro-N-[4-(hydroxy-2-pyridinylmethyl)phenyl]-3-(3-pyridinyl)-5-isoxazolecarboxamide.

12. A composition comprising a pharmaceutically acceptable carrier and, as active ingredient, a therapeutically effective amount of a compound as claimed in claim 1.

13. A process for preparing a compound of formula (I) or a N-oxide, pharmaceutically acceptable addition salt, quaternary amine or stereochemically isomeric form thereof as claimed in claim 1, characterized by, a.) reacting an intermediate of formula (II) wherein W$^1$ is C$_{(1-3)}$alkyloxy, hydroxy or a halogen atom, with an appropriate reagent of formula (III), in a reaction inert solvent and optionally in the presence of a suitable base;

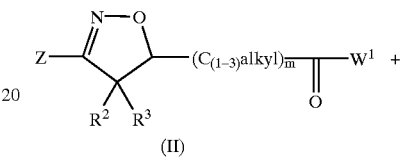

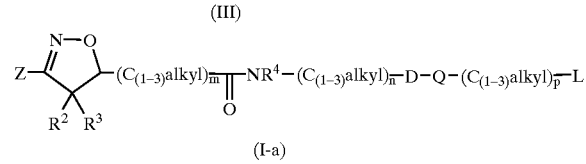

wherein R$^2$, R$^3$, R$^4$, D, Q, L, m, n and p are as defined in claim 1, and Z represents

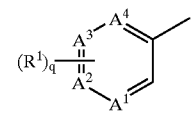

wherein —A$^1$=A$^2$—A$^3$=A$^4$—, q and R$^1$ are as defined in claim 1;

b.) a 1,3-dipolar addition between a compound of formula

wherein Z is as defined in part a.) above, and a compound of formula

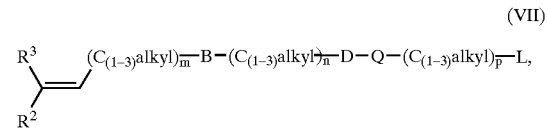

wherein B is (b-1), (b-2) or (b-3) and (b-1), (b-2), (b-3), D, Q, L, R$^2$, R$^3$, m, n and p are as defined in claim 1, in a reaction inert solvent and in the presence of a base;

c.) a cyclization of a compound of formula

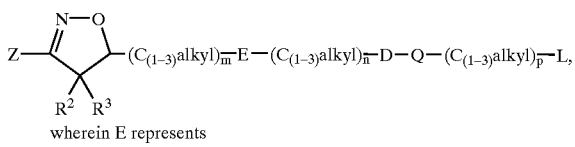
(XII)

wherein E represents

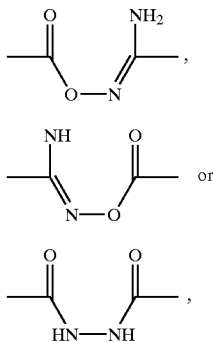
(e-1)
(e-2)
(e-3)

and D, Q, L, $R^2$, $R^3$, m, n and p are as defined in claim 1 and Z is as defined in part a.) above, in a reaction inert solvent;

d.) reacting an intermediate of formula (XVII) wherein $W^4$ is a suitable leaving group with a compound of formula (XVIII), in a reaction-inert solvent in the presence of a catalyst;

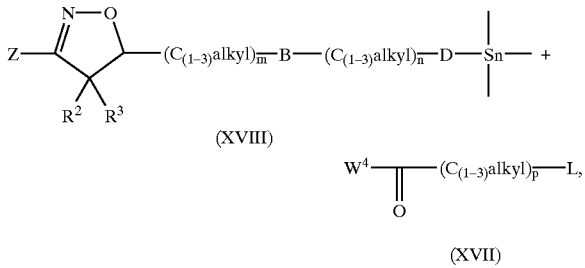
(XVIII)

(XVII)

wherein B, D, L, $R^2$, $R^3$, m, n and p are as defined in claim 1 and Z is as defined in part a.) above;

e.) reacting an intermediate of formula

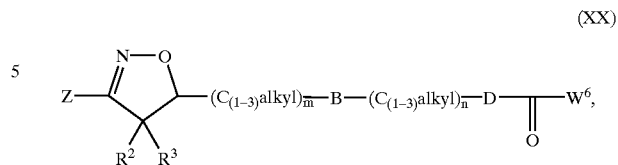
(XX)

wherein $W^6$ is hydroxy or a halogen atom, and B, D, L, $R^2$, $R^3$, m and n are as defined in claim 1 and Z is as defined in part a.) above, with an appropriate functional primary or secondary amine derivative in a reaction inert solvent and in the presence of a suitable base;

and where necessary or desired, any one or more of the following further steps in any order may be performed:
  (i) removing any remaining protecting group(s);
  (ii) converting a compound of formula (I) or a protected form thereof into a further compound of formula (I) or a protected form thereof;
  (iii) converting a compound of formula (I) or a protected form thereof into a N-oxide, a salt, a quaternary amine or a solvate of a compound of formula (I) or a protected form thereof;
  (iv) converting a N-oxide, a salt, a quaternary amine or a solvate of a compound of formula (I) or a protected form thereof into a compound of formula (I) or a protected form thereof;
  (v) converting a N-oxide, a salt, a quaternary amine or a solvate of a compound of formula (I) or a protected form thereof into another N-oxide, a pharmaceutically acceptable addition salt a quaternary amine or a solvate of a compound of formula (I) or a protected form thereof;

where the compound of formula (I) is obtained as a mixture of (R) and (S) enantiomers resolving the mixture to obtain the desired enantiomer.

14. A new method for the treatment of T cell mediated diseases comprising administering an effective amount of a compound of formula (I) or a N-oxide, pharmaceutically acceptable addition salt, quaternary amine or stereochemically isomeric form thereof as defined in claim 1.

15. A method for the treatment of conditions selected from rheumatic diseases, systemic inflammatory diseases, T cell leukemia, transplant rejection and graft versus host disease comprising administering to a host in need thereof an effective amount of a compound of formula I or a N-oxide, pharmaceutically acceptable addition salt, quarternary amine or stereochemically isomeric form thereof as defined in claim 1.

* * * * *